US012690967B2

(12) United States Patent
Dang et al.

(10) Patent No.: US 12,690,967 B2
(45) Date of Patent: Jul. 28, 2026

(54) SUTURE TENSION DISTRIBUTION

(71) Applicant: Edwards Lifesciences Corporation, Irvine, CA (US)

(72) Inventors: Lynn T. Dang, Huntington Beach, CA (US); Emily Cheng Zhou, Aliso Viejo, CA (US); Javier A. Sanguinetti, Irvine, CA (US); Hao-Chung Yang, Tustin, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 870 days.

(21) Appl. No.: 17/935,546

(22) Filed: Sep. 26, 2022

(65) Prior Publication Data

US 2023/0016821 A1     Jan. 19, 2023

Related U.S. Application Data

(63) Continuation of application No. PCT/US2021/024285, filed on Mar. 26, 2021.

(Continued)

(51) Int. Cl.
*A61B 17/04* (2006.01)
*A61F 2/08* (2006.01)
*A61F 2/24* (2006.01)

(52) U.S. Cl.
CPC .......... *A61F 2/2466* (2013.01); *A61F 2/2457* (2013.01); *A61B 17/0401* (2013.01); *A61B 2017/0406* (2013.01); *A61B 2017/0409* (2013.01); *A61B 2017/0414* (2013.01); *A61B 2017/0438* (2013.01); *A61B 2017/0446*

(2013.01); *A61B 2017/0454* (2013.01); *A61B 2017/0458* (2013.01); *A61B 2017/0462* (2013.01); *A61B 2017/0464* (2013.01);

(Continued)

(58) Field of Classification Search
CPC .............................................. A61B 2017/0406
See application file for complete search history.

(56) References Cited

U.S. PATENT DOCUMENTS

| 3,131,957 A | 5/1964 | Musto |
| 3,752,516 A | 8/1973 | Mumma |

(Continued)

FOREIGN PATENT DOCUMENTS

| EP | 0791330 A3 | 11/1997 |
| EP | 3505077 A1 | 7/2019 |

(Continued)

OTHER PUBLICATIONS

Alfieri, 0. el al., "The double-orifice technique in mitral valve repair: a +A198:A225simple solution for complex problems," (2001) J. Thorne. Cardiovasc. Surg., 122(4):674-681.

(Continued)

*Primary Examiner* — Jacqueline Woznicki
(74) *Attorney, Agent, or Firm* — Chang and Hale LLP

(57)     ABSTRACT

A tension-distribution device includes a rotationally-symmetric structure and two or more suture-engagement features associated with the rotationally-symmetric structure, the suture-engagement features being configured to receive one or more suture portions therein. The two or more suture-engagement features are evenly spaced rotationally about an axial center of the rotationally-symmetric structure.

9 Claims, 40 Drawing Sheets

Related U.S. Application Data

(60) Provisional application No. 63/001,076, filed on Mar. 27, 2020.

(52) U.S. Cl.
CPC ................. *A61B 2017/0496* (2013.01); *A61F 2002/0817* (2013.01); *A61F 2220/0075* (2013.01); *A61F 2230/0023* (2013.01)

(56) References Cited

U.S. PATENT DOCUMENTS

| | | | |
|---|---|---|---|
| 4,403,797 A | 9/1983 | Ragland, Jr. | |
| 4,662,376 A | 5/1987 | Belanger | |
| 4,807,625 A | 2/1989 | Singleton | |
| 4,969,892 A | 11/1990 | Burton et al. | |
| 5,144,961 A | 9/1992 | Chen et al. | |
| 5,147,316 A | 9/1992 | Castillenti | |
| 5,203,787 A * | 4/1993 | Noblitt | A61B 17/0401 |
| | | | 411/460 |
| 5,312,423 A | 5/1994 | Rosenbluth et al. | |
| 5,391,176 A | 2/1995 | de la Torre | |
| 5,403,348 A * | 4/1995 | Bonutti | A61B 17/0401 |
| | | | 606/232 |
| 5,405,352 A | 4/1995 | Weston | |
| 5,454,821 A | 10/1995 | Harm et al. | |
| 5,472,446 A | 12/1995 | de la Torre | |
| 5,507,754 A | 4/1996 | Green et al. | |
| 5,527,323 A | 6/1996 | Jervis et al. | |
| 5,554,184 A | 9/1996 | Machiraju | |
| 5,626,614 A | 5/1997 | Hart | |
| 5,643,293 A | 7/1997 | Kogasaka et al. | |
| 5,681,331 A | 10/1997 | de la Torre et al. | |
| 5,716,368 A | 2/1998 | de la Torre et al. | |
| 5,718,717 A * | 2/1998 | Bonutti | A61B 17/0401 |
| | | | 606/232 |
| 5,727,569 A | 3/1998 | Benetti et al. | |
| 5,728,109 A | 3/1998 | Schulze et al. | |
| 5,746,752 A | 5/1998 | Burkhart | |
| 5,769,862 A | 6/1998 | Kammerer et al. | |
| 5,797,928 A | 8/1998 | Kogasaka | |
| 5,824,065 A | 10/1998 | Gross | |
| 5,931,868 A | 8/1999 | Gross | |
| 5,957,936 A | 9/1999 | Yoon et al. | |
| 5,971,447 A | 10/1999 | Steck, III | |
| 5,993,459 A | 11/1999 | Larsen et al. | |
| 6,010,531 A | 1/2000 | Donlon et al. | |
| 6,074,417 A | 6/2000 | Peredo | |
| 6,099,568 A * | 8/2000 | Simonian | A61F 2/0811 |
| | | | 623/13.11 |
| 6,269,819 B1 | 8/2001 | Oz et al. | |
| 6,332,893 B1 | 12/2001 | Mortier et al. | |
| 6,562,051 B1 | 5/2003 | Bolduc et al. | |
| 6,592,609 B1 * | 7/2003 | Bonutti | A61B 17/0487 |
| | | | 606/232 |
| 6,626,930 B1 | 9/2003 | Allen et al. | |
| 6,629,534 B1 | 10/2003 | St. Goar et al. | |
| 6,752,810 B1 | 6/2004 | Gao et al. | |
| 6,840,246 B2 | 1/2005 | Downing | |
| 6,921,408 B2 | 7/2005 | Sauer | |
| 6,940,246 B2 | 9/2005 | Mochizuki et al. | |
| 6,978,176 B2 | 12/2005 | Lattouf | |
| 6,991,635 B2 | 1/2006 | Takamoto et al. | |
| 6,997,950 B2 | 2/2006 | Chawla | |
| 7,112,207 B2 | 9/2006 | Allen et al. | |
| 7,291,168 B2 | 11/2007 | Macoviak et al. | |
| 7,294,148 B2 | 11/2007 | McCarthy | |
| 7,309,086 B2 | 12/2007 | Carrier | |
| 7,316,706 B2 | 1/2008 | Bloom et al. | |
| 7,373,207 B2 | 5/2008 | Lattouf | |
| 7,431,692 B2 | 10/2008 | Zollinger et al. | |
| 7,513,908 B2 | 4/2009 | Lattouf | |
| 7,534,260 B2 | 5/2009 | Lattouf | |
| 7,608,091 B2 | 10/2009 | Goldfarb et al. | |
| 7,618,449 B2 | 11/2009 | Tremulis et al. | |
| 7,632,308 B2 | 12/2009 | Loulmet | |
| 7,635,386 B1 | 12/2009 | Gammie | |
| 7,666,196 B1 | 2/2010 | Miles | |
| 7,744,609 B2 | 6/2010 | Allen et al. | |
| 7,837,727 B2 | 11/2010 | Goetz et al. | |
| 7,871,368 B2 | 1/2011 | Zollinger et al. | |
| 7,871,433 B2 | 1/2011 | Lattouf | |
| 7,959,650 B2 | 6/2011 | Kaiser et al. | |
| 8,029,518 B2 | 10/2011 | Goldfarb et al. | |
| 8,029,565 B2 | 10/2011 | Lattouf | |
| 8,043,368 B2 | 10/2011 | Crabtree | |
| 8,147,542 B2 | 4/2012 | Maisano et al. | |
| 8,187,323 B2 | 5/2012 | Mortier et al. | |
| 8,226,711 B2 | 7/2012 | Mortier et al. | |
| 8,241,304 B2 | 8/2012 | Bachman | |
| 8,252,050 B2 | 8/2012 | Maisano et al. | |
| 8,292,884 B2 | 10/2012 | Levine et al. | |
| 8,303,622 B2 | 11/2012 | Alkhatib | |
| 8,333,788 B2 | 12/2012 | Maiorino | |
| 8,382,829 B1 | 2/2013 | Call et al. | |
| 8,439,969 B2 | 5/2013 | Gillinov et al. | |
| 8,454,656 B2 | 6/2013 | Tuval | |
| 8,465,500 B2 | 6/2013 | Speziali | |
| 8,475,525 B2 | 7/2013 | Maisano et al. | |
| 8,500,800 B2 | 8/2013 | Maisano et al. | |
| 8,608,758 B2 | 12/2013 | Singhatat et al. | |
| 8,663,278 B2 | 3/2014 | Mabuchi et al. | |
| 8,771,296 B2 | 7/2014 | Nobles et al. | |
| 8,828,053 B2 | 9/2014 | Sengun et al. | |
| 8,845,686 B2 | 9/2014 | Bennett | |
| 8,852,213 B2 | 10/2014 | Gammie et al. | |
| 8,888,791 B2 | 11/2014 | Jaramillo et al. | |
| 8,926,662 B2 | 1/2015 | Perriello et al. | |
| 8,940,008 B2 | 1/2015 | Kunis | |
| 9,131,884 B2 | 9/2015 | Holmes et al. | |
| 9,192,287 B2 | 11/2015 | Saadat et al. | |
| 9,636,100 B2 | 5/2017 | Wyman et al. | |
| 2001/0041916 A1 * | 11/2001 | Bonutti | A61B 17/0401 |
| | | | 606/232 |
| 2002/0013571 A1 | 1/2002 | Goldfarb et al. | |
| 2003/0023254 A1 | 1/2003 | Chiu | |
| 2003/0094180 A1 | 5/2003 | Benetti | |
| 2003/0105519 A1 | 6/2003 | Fasol et al. | |
| 2003/0120264 A1 | 6/2003 | Lattouf | |
| 2003/0120341 A1 | 6/2003 | Shennib et al. | |
| 2003/0176920 A1 * | 9/2003 | Sklar | A61F 2/08 |
| | | | 606/1 |
| 2004/0044365 A1 | 3/2004 | Bachman | |
| 2004/0093023 A1 | 5/2004 | Allen et al. | |
| 2004/0199183 A1 | 10/2004 | Oz et al. | |
| 2005/0004667 A1 | 1/2005 | Swinford et al. | |
| 2005/0019735 A1 | 1/2005 | Demas | |
| 2005/0075654 A1 | 4/2005 | Kelleher | |
| 2005/0119735 A1 | 6/2005 | Spence et al. | |
| 2005/0149067 A1 | 7/2005 | Takemoto et al. | |
| 2005/0149093 A1 | 7/2005 | Pokorney | |
| 2005/0154402 A1 | 7/2005 | Sauer et al. | |
| 2005/0216036 A1 | 9/2005 | Nakao | |
| 2005/0216077 A1 | 9/2005 | Mathis et al. | |
| 2005/0261710 A1 | 11/2005 | Sakamoto et al. | |
| 2005/0267493 A1 | 12/2005 | Schreck et al. | |
| 2006/0030866 A1 | 2/2006 | Schreck | |
| 2006/0100698 A1 | 5/2006 | Lattouf | |
| 2006/0111739 A1 | 5/2006 | Staufer et al. | |
| 2006/0167541 A1 | 7/2006 | Lattouf | |
| 2006/0190030 A1 | 8/2006 | To et al. | |
| 2006/0229671 A1 * | 10/2006 | Steiner | A61B 17/0401 |
| | | | 606/232 |
| 2006/0282088 A1 | 12/2006 | Ryan | |
| 2007/0001857 A1 | 1/2007 | Hartmann et al. | |
| 2007/0016208 A1 | 1/2007 | Thornes | |
| 2007/0049952 A1 | 3/2007 | Weiss | |
| 2007/0055292 A1 | 3/2007 | Ortiz et al. | |
| 2007/0073342 A1 | 3/2007 | Stone et al. | |
| 2007/0112422 A1 | 5/2007 | Dehdashtian | |
| 2007/0112425 A1 | 5/2007 | Schaller et al. | |
| 2007/0118151 A1 | 5/2007 | Davidson | |
| 2007/0118154 A1 | 5/2007 | Crabtree | |
| 2007/0149995 A1 | 6/2007 | Quinn et al. | |

(56) References Cited

U.S. PATENT DOCUMENTS

| | | | |
|---|---|---|---|
| 2007/0197858 A1 | 8/2007 | Goldfarb et al. | |
| 2007/0213582 A1 | 9/2007 | Zollinger et al. | |
| 2007/0270793 A1 | 11/2007 | Lattouf | |
| 2008/0004597 A1 | 1/2008 | Lattouf et al. | |
| 2008/0009888 A1 | 1/2008 | Ewers et al. | |
| 2008/0065203 A1 | 3/2008 | Khalapyan | |
| 2008/0140093 A1 | 6/2008 | Stone et al. | |
| 2008/0167714 A1 | 7/2008 | St. Goar et al. | |
| 2008/0177302 A1 | 7/2008 | Shurnas | |
| 2008/0188893 A1 | 8/2008 | Selvitelli et al. | |
| 2008/0195126 A1 | 8/2008 | Solem | |
| 2008/0228223 A1 | 9/2008 | Alkhatib | |
| 2008/0228266 A1* | 9/2008 | McNamara | A61F 2/2445 |
| | | | 623/2.36 |
| 2008/0249504 A1 | 10/2008 | Lattouf et al. | |
| 2008/0269781 A1 | 10/2008 | Funamura et al. | |
| 2009/0005863 A1 | 1/2009 | Goetz et al. | |
| 2009/0043153 A1 | 2/2009 | Zollinger et al. | |
| 2009/0105729 A1 | 4/2009 | Zentgraf | |
| 2009/0105751 A1 | 4/2009 | Zentgraf | |
| 2009/0276038 A1 | 11/2009 | Tremulis et al. | |
| 2010/0023056 A1 | 1/2010 | Johansson et al. | |
| 2010/0023117 A1 | 1/2010 | Yoganathan et al. | |
| 2010/0023118 A1 | 1/2010 | Medlock et al. | |
| 2010/0042147 A1 | 2/2010 | Janovsky et al. | |
| 2010/0063586 A1* | 3/2010 | Hasenkam | A61B 17/0401 |
| | | | 623/2.37 |
| 2010/0174297 A1 | 7/2010 | Speziali | |
| 2010/0179574 A1 | 7/2010 | Longoria et al. | |
| 2010/0210899 A1 | 8/2010 | Schankereli | |
| 2010/0298930 A1 | 11/2010 | Orlov | |
| 2010/0305609 A1* | 12/2010 | Cartledge | A61B 17/0487 |
| | | | 606/232 |
| 2011/0015476 A1 | 1/2011 | Franco | |
| 2011/0022083 A1 | 1/2011 | DiMatteo et al. | |
| 2011/0022084 A1 | 1/2011 | Sengun et al. | |
| 2011/0028995 A1 | 2/2011 | Miraki et al. | |
| 2011/0029071 A1 | 2/2011 | Zlotnick et al. | |
| 2011/0060407 A1 | 3/2011 | Ketai et al. | |
| 2011/0106106 A1 | 5/2011 | Meier et al. | |
| 2011/0144743 A1 | 6/2011 | Lattouf | |
| 2011/0264208 A1 | 10/2011 | Duffy et al. | |
| 2011/0270278 A1 | 11/2011 | Overes et al. | |
| 2011/0288637 A1 | 11/2011 | De Marchena | |
| 2011/0307055 A1 | 12/2011 | Goldfarb et al. | |
| 2012/0004669 A1 | 1/2012 | Overes et al. | |
| 2012/0143215 A1 | 6/2012 | Corrao et al. | |
| 2012/0150223 A1 | 6/2012 | Manos et al. | |
| 2012/0179184 A1 | 7/2012 | Orlov | |
| 2012/0184971 A1 | 7/2012 | Zentgraf et al. | |
| 2012/0203072 A1 | 8/2012 | Lattouf et al. | |
| 2012/0226294 A1 | 9/2012 | Tuval | |
| 2012/0226349 A1 | 9/2012 | Tuval et al. | |
| 2013/0018459 A1 | 1/2013 | Maisano et al. | |
| 2013/0035757 A1 | 2/2013 | Zentgraf et al. | |
| 2013/0253641 A1 | 9/2013 | Lattouf | |
| 2013/0282059 A1 | 10/2013 | Ketai et al. | |
| 2013/0345749 A1 | 12/2013 | Sullivan et al. | |
| 2014/0031926 A1 | 1/2014 | Kudlik et al. | |
| 2014/0039607 A1 | 2/2014 | Kovach | |
| 2014/0067052 A1 | 3/2014 | Chau et al. | |
| 2014/0114404 A1 | 4/2014 | Gammie et al. | |
| 2014/0214152 A1 | 7/2014 | Bielefeld | |
| 2014/0243968 A1 | 8/2014 | Padala | |
| 2014/0364938 A1 | 12/2014 | Longoria et al. | |
| 2015/0032127 A1 | 1/2015 | Gammie et al. | |
| 2015/0045879 A1 | 2/2015 | Longoria et al. | |
| 2019/0117401 A1* | 4/2019 | Cortez, Jr. | A61B 17/0469 |
| 2019/0175346 A1 | 6/2019 | Schaffner et al. | |
| 2019/0343633 A1* | 11/2019 | Garvin | A61B 17/0401 |
| 2020/0155315 A1 | 5/2020 | Zhang et al. | |
| 2023/0016821 A1* | 1/2023 | Dang | A61F 2/2457 |

FOREIGN PATENT DOCUMENTS

| | | | |
|---|---|---|---|
| JP | 2013517110 A | 5/2013 | |
| WO | 2004037463 A1 | 5/2004 | |
| WO | 2006127509 A2 | 11/2006 | |
| WO | 2007100268 A2 | 9/2007 | |
| WO | 2007119057 A1 | 10/2007 | |
| WO | 2008013869 A2 | 1/2008 | |
| WO | 2008124110 A3 | 12/2008 | |
| WO | 2008143740 A3 | 2/2009 | |
| WO | 2006078694 A3 | 4/2009 | |
| WO | 2009081396 A2 | 7/2009 | |
| WO | 2010070649 A1 | 6/2010 | |
| WO | 2010105046 A1 | 9/2010 | |
| WO | 2012137208 A1 | 10/2012 | |
| WO | 2013003228 A1 | 1/2013 | |
| WO | WO-2014055678 A1 | 4/2014 | |
| WO | 2014093861 A1 | 6/2014 | |
| WO | 2015020816 A1 | 2/2015 | |
| WO | 2016192481 A1 | 12/2016 | |
| WO | WO-2020051147 A1 | 3/2020 | |

OTHER PUBLICATIONS

Barbero-Marcial, M. et al., "Transxiphoid Approach Without Median Sternotomy for the Repair of Atrial Septa! Defects," (1998) Ann. Thorne. Surg., 65(3):771-774.

Braunberger, E. et al., "Very long-term results (more than 20 years) of valve repair with Carpentier's echniques in honheumatic mitral valve insufficiency," (2001) Circulation, I 04:1-8-1-11.

Carpentier, Alain, "Cardiac valve surgery—the 'French coffection'," The Journal of Thoracic and Cardiovascular Surgery, vol. 86, No. 3, Sep. 1983, 15 pages.

David, T. E. et al., "Mitra! valve repair by replacement of chordae tendineae with polytetrafluoroethylene sutures," (1991) J. Thorne. Cardiovasc. Surg., 101 (3 ):495-50 I.

David, T. E. et al., "Replacement of chordae tendineae with Gore-Tex sutures: a ten-year experience," (1996) J. Heart Valve Dis., 5( 4 ):352-355.

Doty, D. B. et al., "Full-Spectrum Cardiac Surgery Through a Minimal Incision: Mini-Sternotomy (Lower Half) Technique," (1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitral valve prolapse," (1997) J. Heall Valve Dis., 6(6):594-598.

Frater, R. W. M. ct al., "Chordal replacement in mitral valve repair," (1990) Circulation, 82(suppl. IV):IV-125-IV-130.

Frater, R. W. M., "Anatomical rules for the plastic repair of a diseased mitral valve," (1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricular Dysfunction and Functional Mitral Regurgitation," (2003) Ann. Thorne. Surg., 75:809-811.

Kasegawa, H. ct al., "Simple method for detennining proper length of allificial chordae in mitral valve repair," (1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylcnc suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe rnyxomatous disease: surgical technique," (2000) European Journal of Cardiothorncic Surgery, 17(3):201-205.

(56) References Cited

OTHER PUBLICATIONS

Merendino, K. A. et al., "The open con-ection of rheumatic mitral regurgitation and/or stenosis with special reference to regurgitation treated by posteromedial annuloplasty utilizing a pump-oxygenator," (1959) Annals of Surgery, 150(1 ):5-22.

Minatoya, K. et al., "Pathologic aspects of polytetrafluoroethylene sutures in human heart," ( 1996) Ann. Thorac. Surg., 61 (3 ):883-887.

Mohty, D. ct al., "Very long-term survival and durability ofmitral valve repair for mitral valve prolapse," (2001) Circulation, 104:1-1-1-7.

*Neochord, Inc.* v. *University of Maryland, Bal tim ore*, Case No. JPR2016-00208, Decision on Institution of Inter Faries Review, 37 CFR §42. 108, Paper 6, Entered May 24, 2016, 28 pages.

*Neochord, Inc.* v. *University of Maryland, Baltimore*, Case No. IPR2016-00208, Declaration of Dr. Lishan Aklog, dated Nov. 17, 2015, 91 pages.

*Neochord, Inc.* v. *University of Maryland, Baltimore*, Case No. IPR2016-00208, Petition for inter ParlesReview of U.S. Pat. No. 7,635,386, dated Nov. 18, 2015, 65 pages.

Nigro, J. J. et al., "Neochordal repair of the posterior mitral leaflet," (2004) J. Thorne. Cardiovasc. Surg., 127 (2):440-447.

Phillips, M. R. et al., "Repair of anterior leaflet mitral valve prolapse: chordal replacement versus chordal shrntening," (2000) Ann. Thorac. Surg., 69(1 ):25-29.

Russo, M. J. ct al.—Transapical Approach for Mitral Valve Repair during Insertion of a Left Ventricular Assist Device, Hindawi Publishing Corporation, The Scientific World Journal, vol. 2013, Article ID 925310, [ online], Retrieved from the internet: <URL: http://dx.doi.org/J 0.1155/2013/92531 O> Apr. 11, 2013, 4 pages.

Sarsam, M.A. I., "Simplified technique for determining the length of artificial cl1ordae in milral valve repair," (2002) Ann. Thorac. Surg., 73(5): 1659-1660.

Savage, E. B. et al., Use of mitral valve repair: analysis of contemporary United States experience reported to the society of thoracic surgeons national cardiac database, . . . (2003) Ann. Thorne. Surg., 75:820-825.

Speziali, G. et al., "Co!l'ection of Mitral Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heaii surgery without cardiopulmonary bypass: Atrial septa! defect closure in a swine model," (2005) J. Thorne. Cardiovasc. Surg., 130: 1348-1357.

Von Oppell, U. 0. et al., "Chordal replacement for both minimally invasive and conventional mitral valve surgery using promcasurcd Gore-Tex loops," (2000) Ann. Thorne. Surg., 70(6):2166-2168.

Zussa, C. et al., Artificial mitral valve chordae: experimental and clinical experience;—( 1990) Ann. Thorne. Surg., 50 (3):367-373.

Zussa, C. et al., "Seven-year experience with chordal replacement with expanded polytetrafluoroethylene in floppymitral valve," (1994)1. Thorac. Cardiovasc. Surg., 108(1):37-41.

Zussa, C. et al., "Surgical technique for artificial mitral chordae implantation," ( 1991) Journal of Cardiac Surgery, 6 (4):432-438.

Zussa, C., "Artificial chordae," (1995) J. Heart Valve Dis., 4(2):S249-S256.

* cited by examiner

*360*

| |
|---|
| IMPLANT TISSUE ANCHORS |

*362*

| |
|---|
| ENGAGE SUTURES WITH SUTURE-ENGAGEMENT FEATURES OF A TENSION-DISTRIBUTION DEVICE |

*364*

| |
|---|
| COUPLE SUTURES ON/IN TENSION-DISTRIBUTION DEVICE |

*366*

| |
|---|
| PERMIT SUTURE COUPLING TO MIGRATE TO DISTRIBUTE TENSION OF SUTURES |

*368*

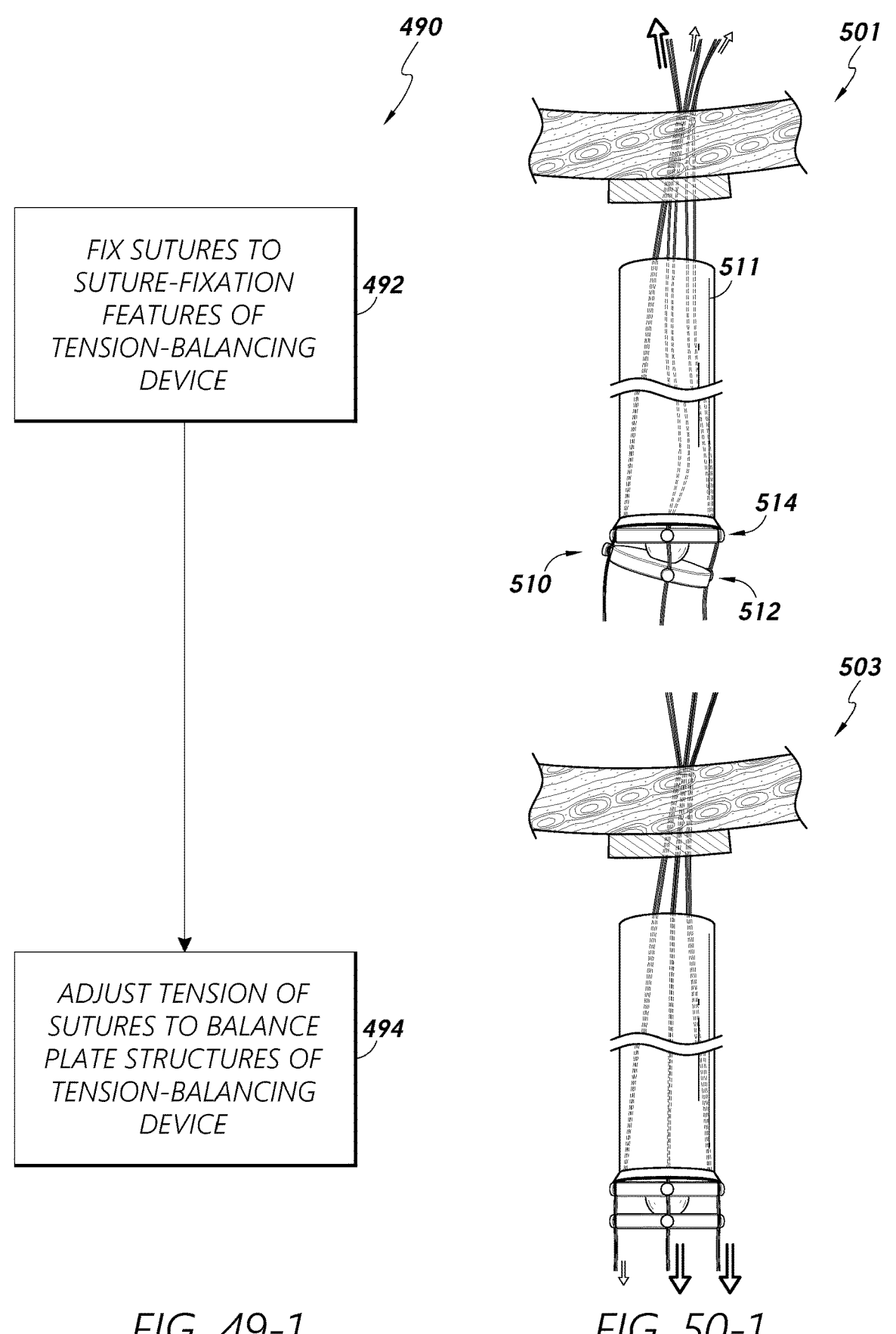
FIG. 49-1                    FIG. 50-1

CLAMP SUTURES AT BALANCED TENSIONS

REMOVE TOURNIQUET

TIE KNOTS TO SECURE SUTURES AT BALANCED TENSIONS

SUTURE TENSION DISTRIBUTION

RELATED APPLICATION

This application is a continuation of International Patent Application No. PCT/US2021/024285, filed Mar. 26, 2021, which claims the benefit of U.S. Patent Application No. 63/001,076, filed on Mar. 27, 2020, the entire disclosures all of which are incorporated by reference for all purposes.

BACKGROUND

Technical Field

The present disclosure generally relates to the field of suture tensioning.

Description of Related Art

Certain medical and other procedures involve the use of sutures or other similar devices. The respective tension of such suture(s) can affect the behavior of the sutures over time.

SUMMARY

Described herein are methods and devices that facilitate the even distribution and/or rebalancing of sutures, such as sutures used in connection with cardiac leaflet tissue anchors.

In some implementations, the present disclosure relates to a tension-distribution device comprising a rotationally-symmetric structure and two or more suture-engagement features associated with the rotationally-symmetric structure, the suture-engagement features being configured to receive one or more suture portions therein. The two or more suture-engagement features are evenly spaced rotationally about an axial center of the rotationally-symmetric structure.

The rotationally-symmetric structure can be at least partially disk-shaped.

In some examples, the rotationally-symmetric structure comprises a topside face and a bottom-side face. For example, the topside face of the rotationally-symmetric structure can have one or more suture channels associated therewith. In some examples, the two or more suture-engagement features comprise apertures that axially traverse the rotationally-symmetric structure from the topside face to the bottom-side face.

The two or more suture-engagement features can comprise four suture-engagement features.

In some examples, the two or more suture-engagement features consists of three suture-engagement features. For example, the rotationally-symmetric structure can be at least partially triangular in shape.

The two or more suture-engagement features can be associated with a radial side portion of the tension-distribution device.

In some examples, the tension-distribution device further comprises an axial cover. For example, the cover can have a central aperture therein. In some examples, the cover forms an enclosure with the rotationally-symmetric structure that is configured to have sutures disposed therein.

In some implementations, the present disclosure relates to a method for tensioning sutures. The method comprises engaging one or more first suture portions with first suture-engagement feature of a rotationally-symmetric tension-distribution device, engaging one or more second suture portions with a second suture-engagement feature of the tension-distribution device, forming a coupling of the one or more first suture portions and the one or more second suture portions on a proximal side of the tension-distribution device, and adjusting tension of the one or more first suture portions and tension of the one or more second suture portions at least in part by permitting the coupling to migrate toward the first suture-engagement feature.

Forming the coupling can comprise tying the one or more first suture portions and the one or more second suture portions together to form one or more knots.

In some examples, the coupling comprises a clamp device.

Migration of the coupling towards the first suture-engagement feature can balance the tension of the one or more first suture portions and the tension of the one or more second suture portions.

In some examples, adjusting tension of the one or more first suture portions and tension of the one or more second suture portions involves decreasing the tension of the one or more first suture portions and decreasing increasing the tension of the one or more second suture portions.

In some examples, adjusting tension of the one or more first suture portions and tension of the one or more second suture portions is performed postoperatively within a closed chest cavity of a patient.

The method can further comprise pulling slack out of at least one of the one or more first suture portions and the one or more second suture portions prior to said forming the coupling.

In some examples, the first suture-engagement feature and the second suture-engagement feature are positioned on a common radial axis of the tension-distribution device and on opposite sides of the suture-tensioning device.

In some examples, the one or more first suture portions are associated with a first implanted tissue anchor and the one or more second suture portions are associated with a second implanted tissue anchor.

In some implementations, the present disclosure relates to a tension-balancing device comprising a first plate structure, a second plate structure, a fulcrum fixed to the second plate structure, a first suture-fixation feature associated with one of the first plate structure and the second plate structure, and a second suture-fixation feature associated with the one of the first plate structure and the second plate structure.

The first plate structure can have a recess configured to receive an apex portion of the fulcrum.

In some examples, the fulcrum is semi-spherical in shape.

In some examples, the fulcrum is cone-shaped.

Each of the first and second suture-fixation features can comprise a bar and an end flange.

In some implementations, the present disclosure relates to a method for balancing tension in sutures. The method comprises fixing one or more first suture portions to a first suture-engagement feature associated with a first rotationally-symmetric plate structure of a tension-balancing device, fixing one or more second suture portions to a second suture-engagement feature associated with the first plate structure, and adjusting tension of the one or more first suture portions to bring the first plate structure into a more parallel orientation with respect to a second plate structure, wherein a fulcrum is disposed between the first plate structure and the second plate structure.

The method can further comprise placing the first plate structure on the fulcrum, wherein the fulcrum is fixed to the second plate structure.

The method can further comprise attaching the tension-balancing device to a tourniquet.

The method can further comprise clamping the one or more first suture portions and the one or more second suture portions after said adjusting.

In some examples, fixing the one or more first suture portions involves wrapping the one or more first suture portions around an axially-projecting bar associated with the first plate structure.

Each method disclosed herein also encompass simulations of the method, which are useful, for example, for teaching, demonstration, testing, device development, and procedure development. For example, methods for treating or diagnosing a patient include corresponding simulated methods performed on simulated patients. Suitable simulated patients or anthropogenic ghosts can include any combination of physical and virtual elements. Examples of physical elements include whole human or animal cadavers, or any portion thereof, including, organ systems, individual organs, or tissue; and manufactured cadaver, organ system, organ, or tissue simulations. Examples of virtual elements include visual simulations, which can be displayed on a screen; projected on a screen, surface, or volume; and holographic images. The simulation can also include one or more of another type of sensory input, for example, auditory, tactile, and olfactory stimuli.

For purposes of summarizing the disclosure, certain aspects, advantages and novel features have been described. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

BRIEF DESCRIPTION OF THE DRAWINGS

Various examples are depicted in the accompanying drawings for illustrative purposes and should in no way be interpreted as limiting the scope of the disclosure. In addition, various features of different disclosed examples can be combined to form additional examples, which are part of this disclosure. Throughout the drawings, reference numbers may be reused to indicate correspondence between reference elements. However, it should be understood that the use of similar reference numbers in connection with multiple drawings does not necessarily imply similarity between respective examples associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some instances or configurations.

4 anchor sutureform projected therefrom through a target heart valve leaflet in accordance with one or more examples.

Figure 6:
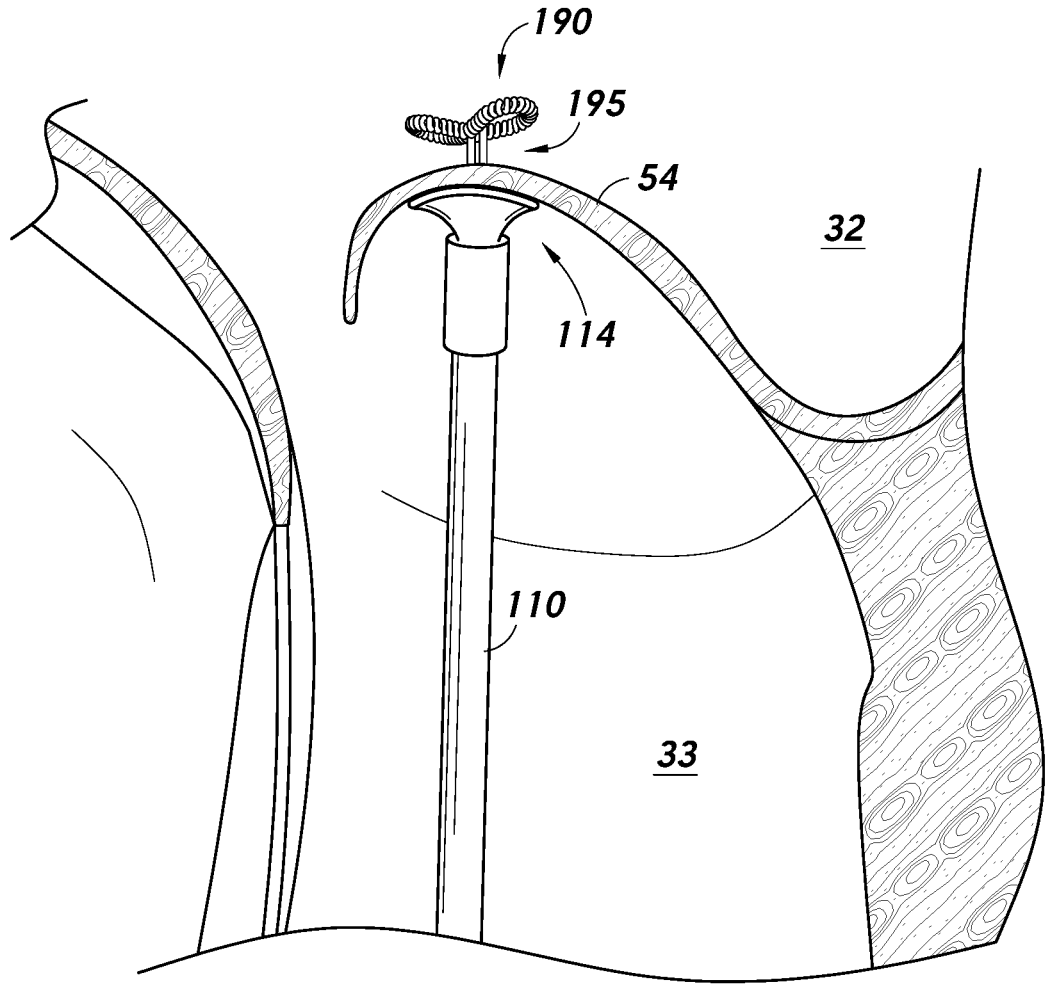

FIG. 6 is a close-up view of a distal portion of a tissue anchor delivery device shaft assembly positioned against a target heart valve leaflet and an associated tissue anchor deployed on a distal side of the leaflet in accordance with one or more examples.

Figure 7:
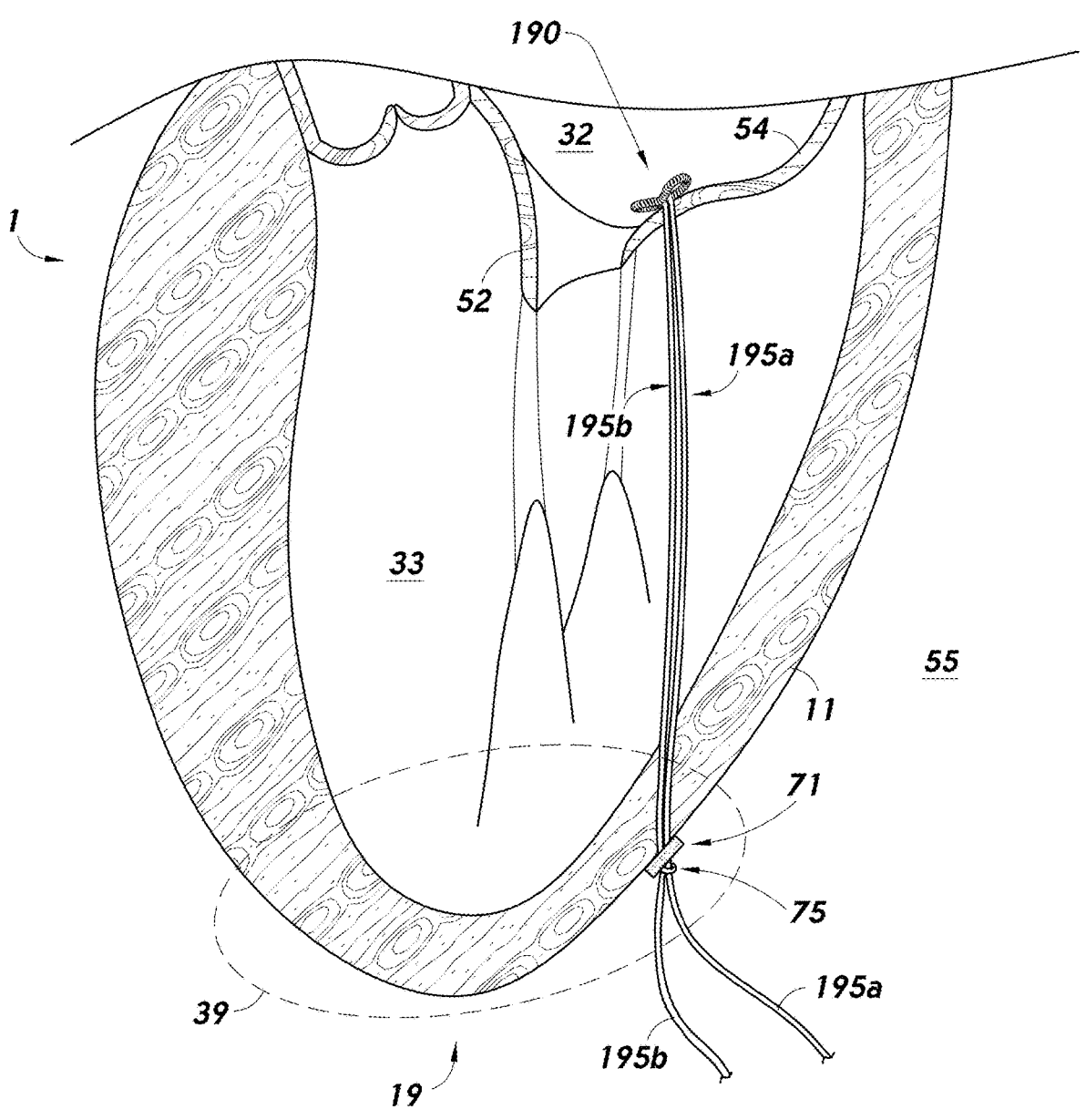

FIG. 7 shows a cutaway view of a deployed leaflet anchor in a heart in accordance with one or more examples.

Figure 8:
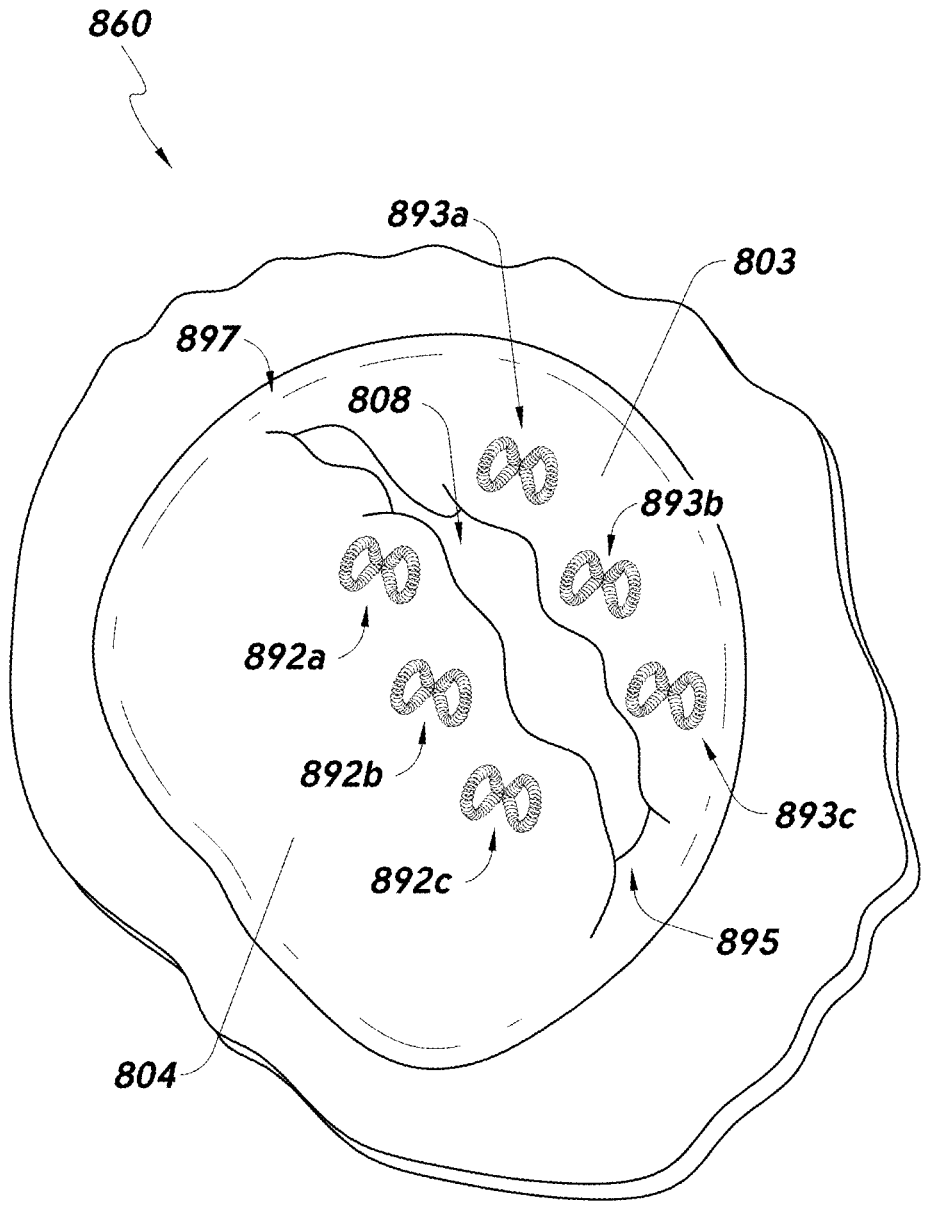

FIG. 8 shows a top view of a heart valve with leaflets having a plurality of tissue anchors implanted therein in accordance with one or more examples.

Figure 9:
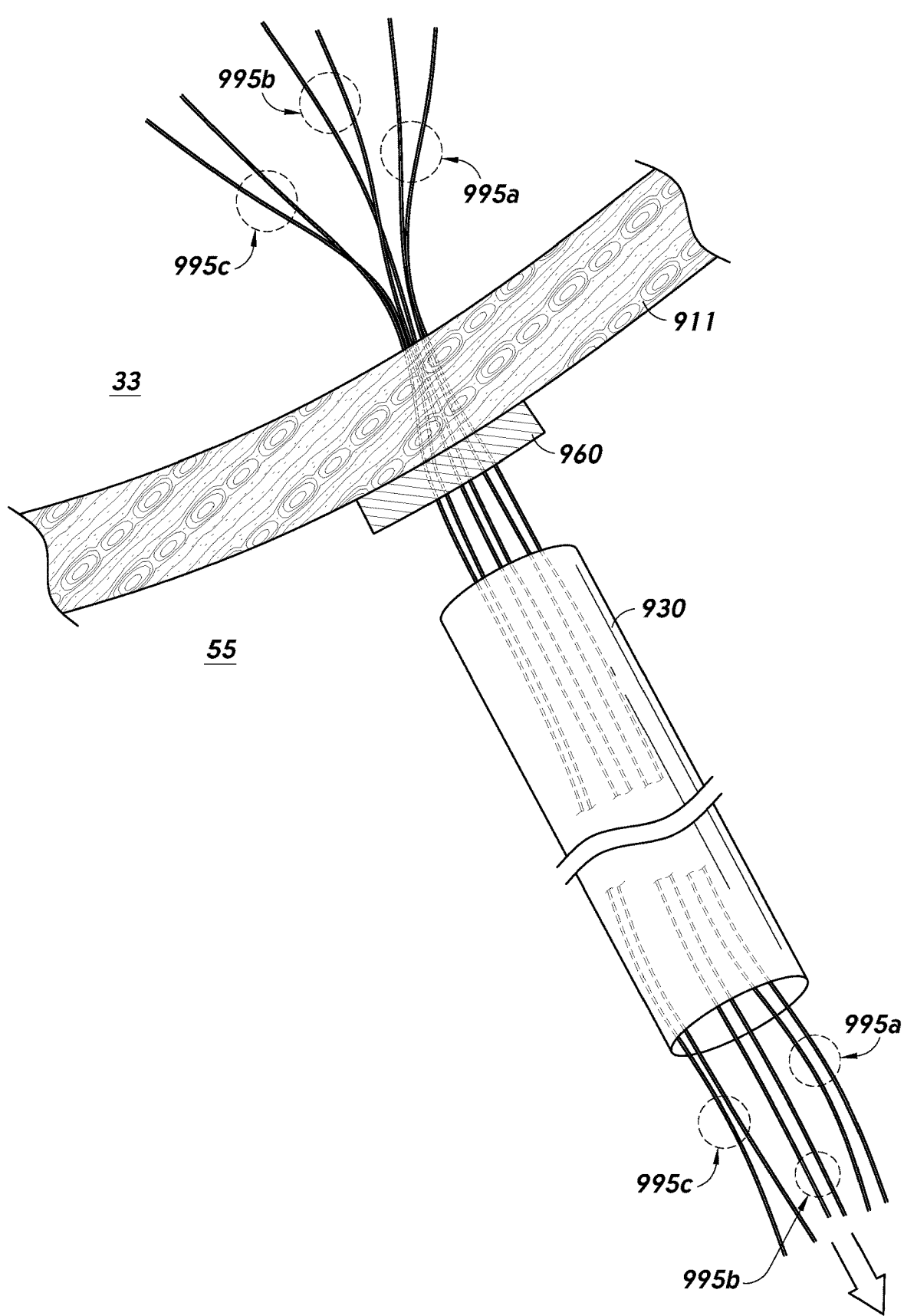

FIG. 9 shows a plurality of suture pairs passing through a cardiac tissue wall and through a tourniquet in accordance with one or more examples.

Figure 10:
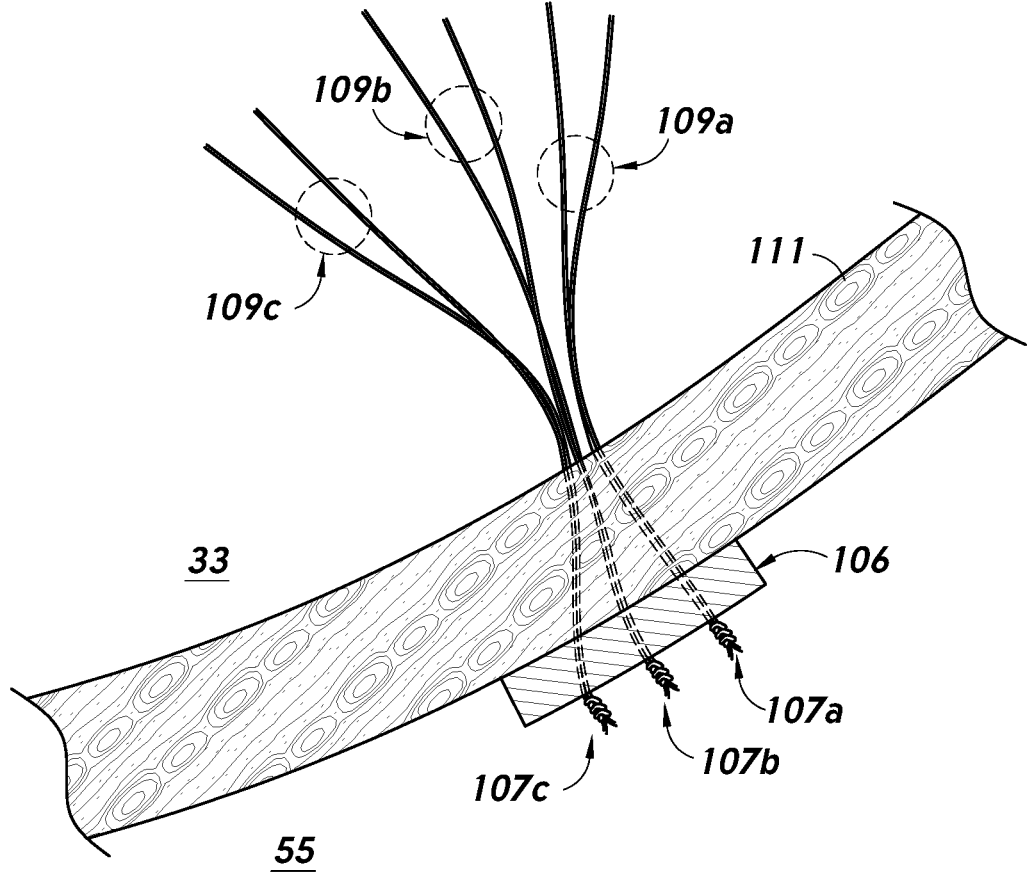

FIG. 10 shows a plurality of suture pairs passing through a cardiac tissue wall and knotted on a pledget in accordance with one or more examples.

Figure 11:
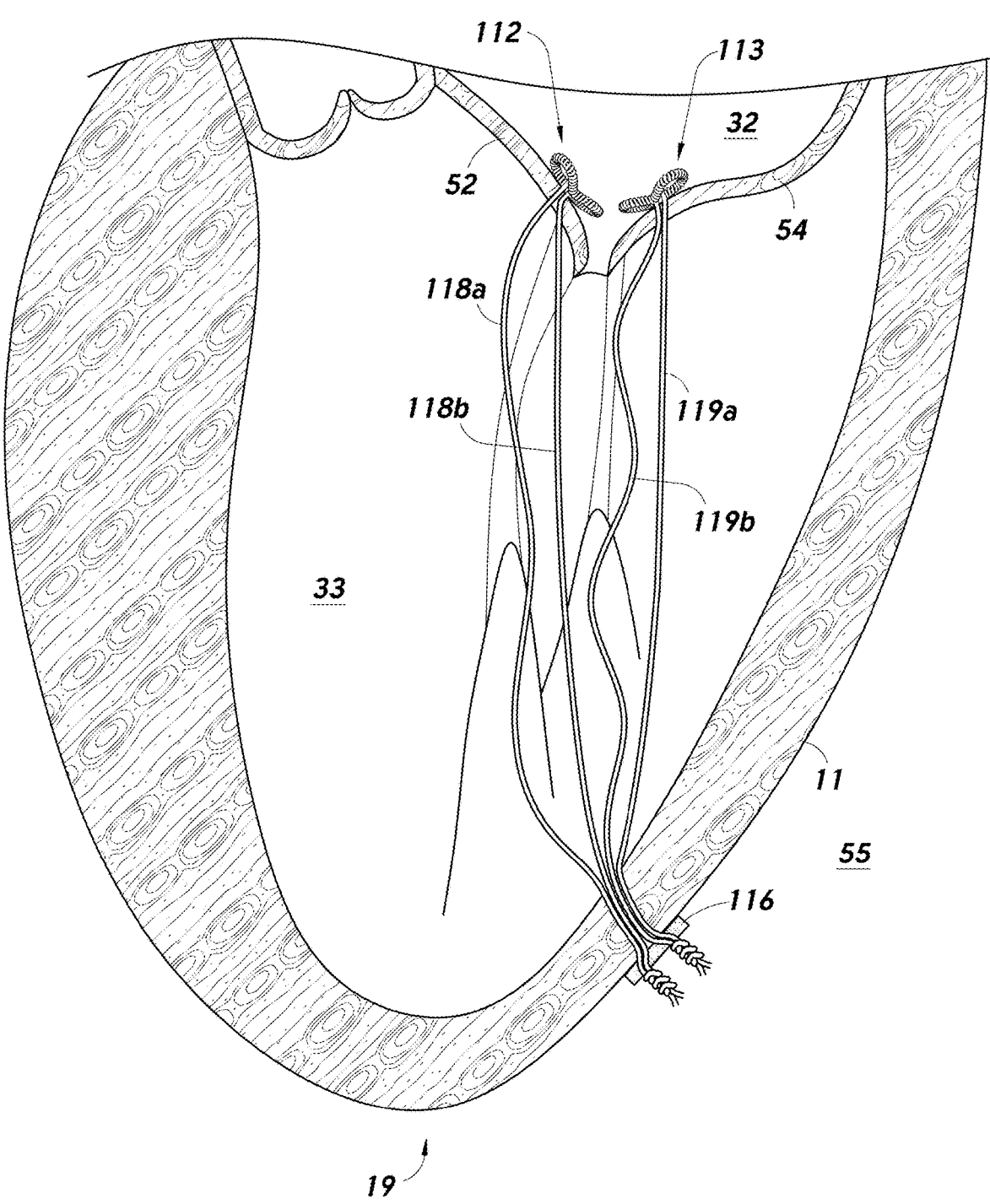

FIG. 11 shows a cutaway view of a heart including a plurality of leaflet anchors implanted therein in accordance with one or more examples.

Figure 12:
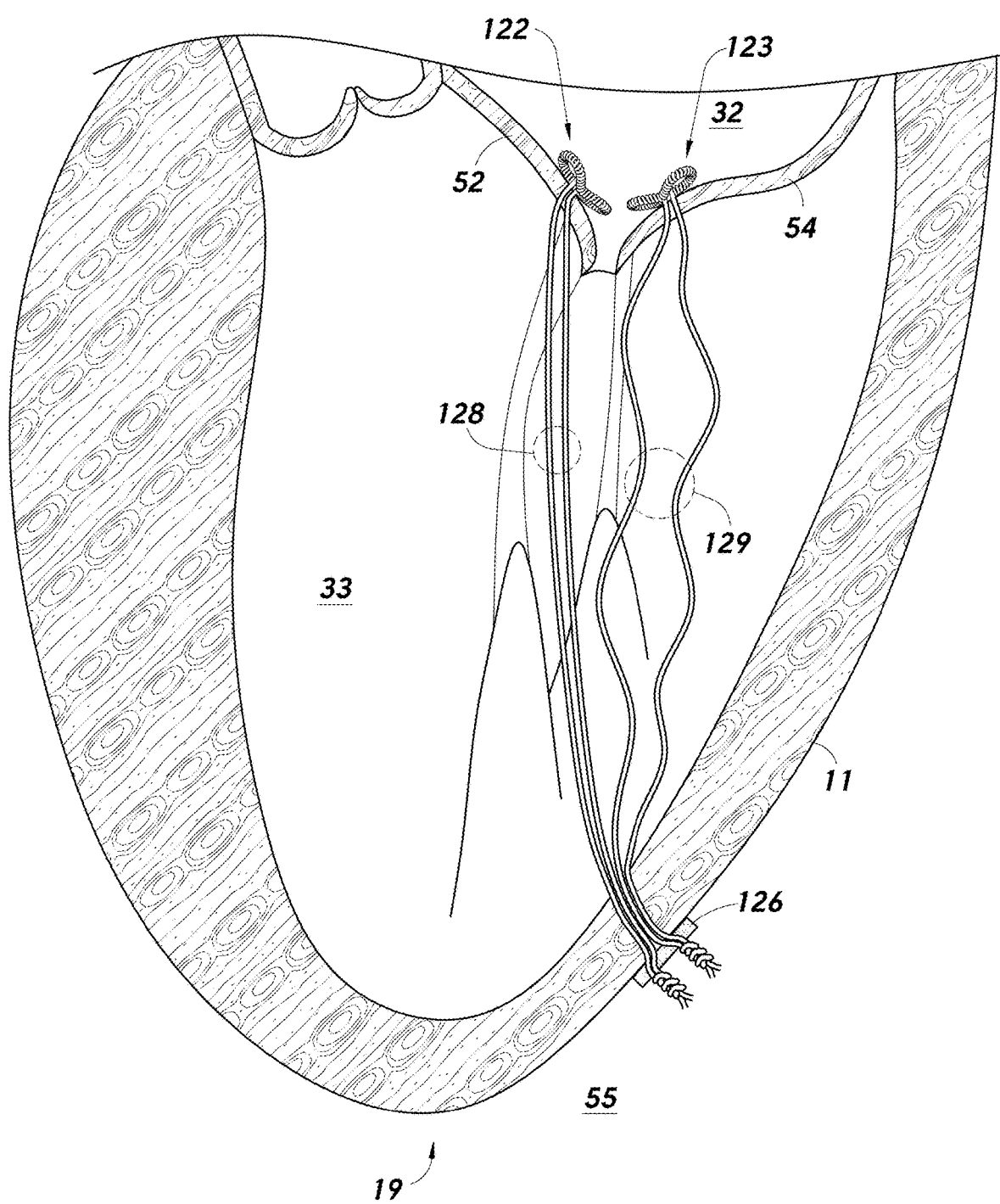

FIG. 12 shows a cutaway view of a heart including a plurality of leaflet anchors implanted therein in accordance with one or more examples.

Figure 13:
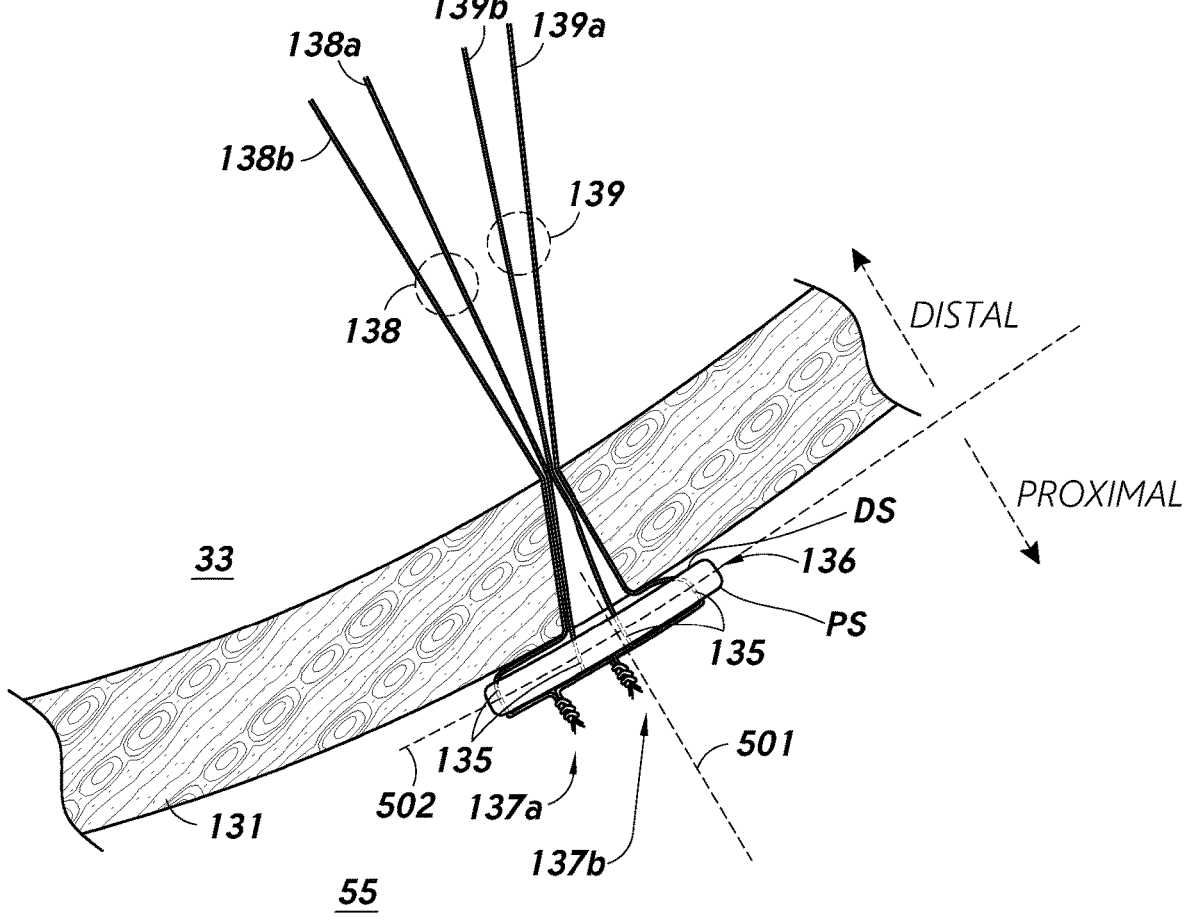

FIG. 13 shows a cutaway side view of a tension-distribution device having sutures engaged therewith in accordance with one or more examples.

Figure 14:
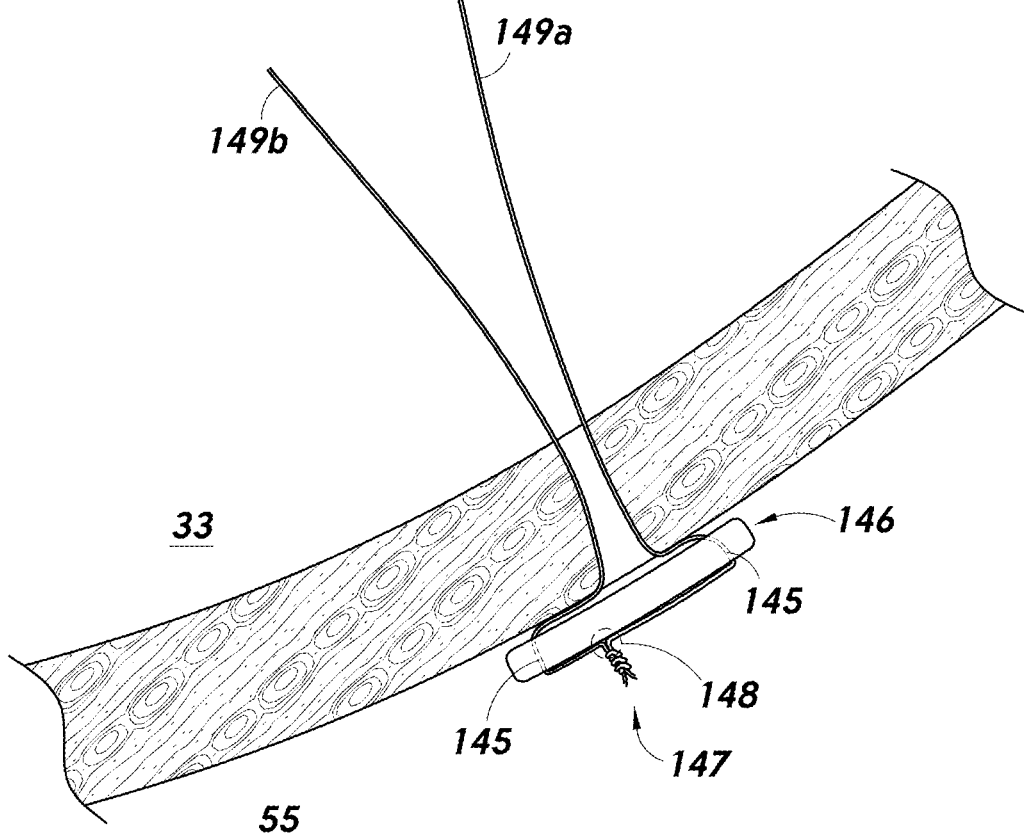

FIG. 14 shows a cutaway side view of a tension-distribution device having sutures engaged therewith in accordance with one or more examples.

Figure 15:
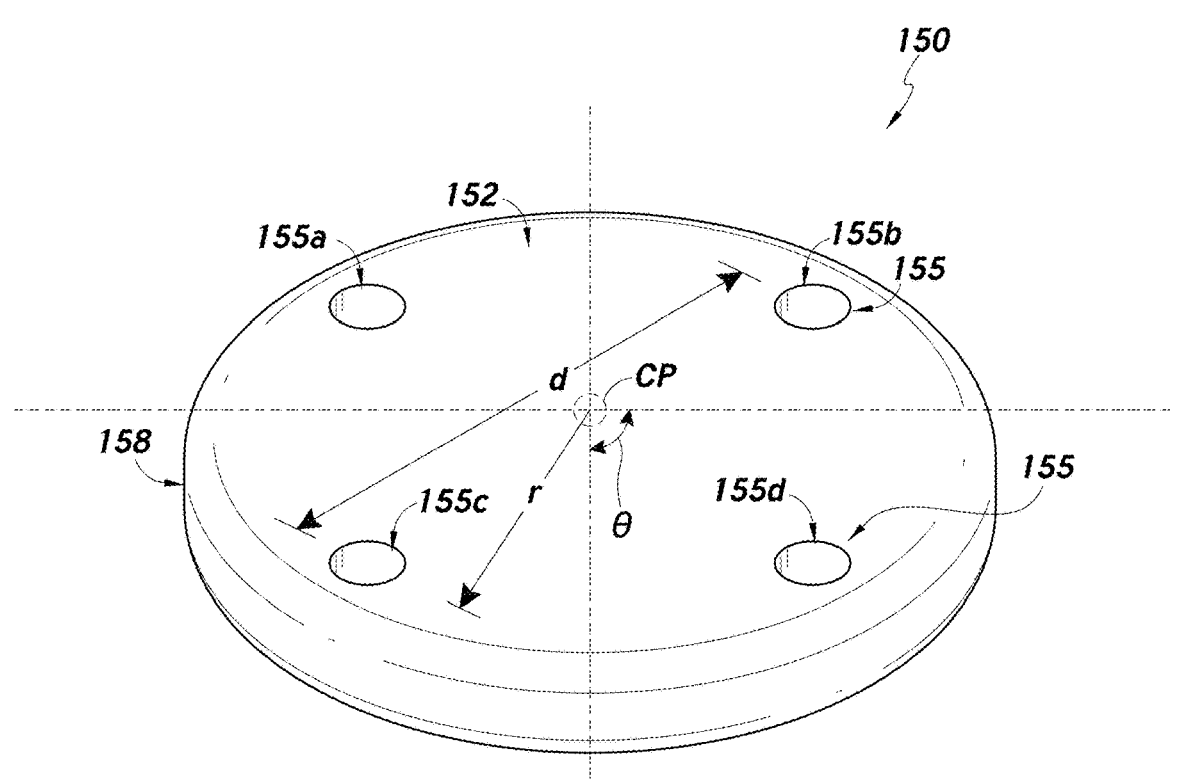

FIG. 15 shows a top and side perspective view of a tension-distribution device in accordance with one or more examples.

Figure 16:
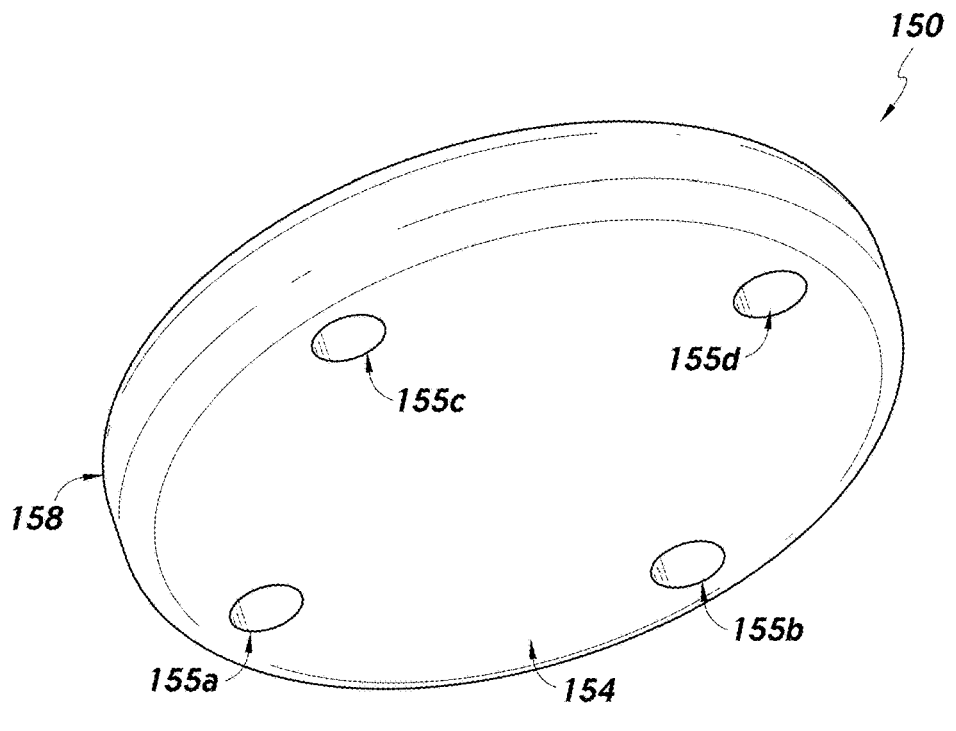

FIG. 16 shows a bottom and side perspective view of a tension-distribution device in accordance with one or more examples.

Figure 17:
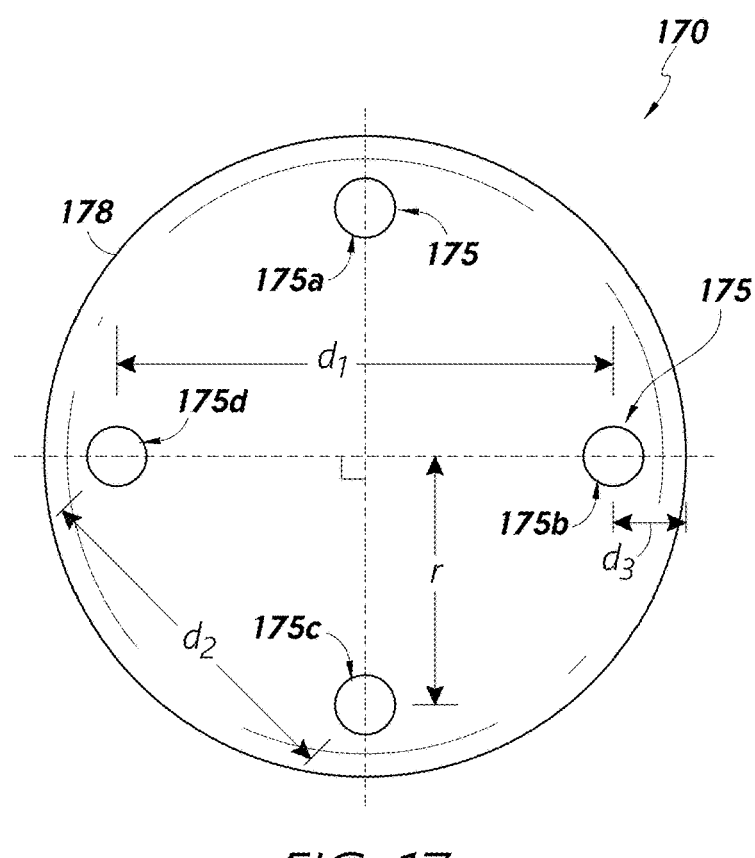

FIG. 17 shows a top or bottom view of a tension-distribution device including four suture-engagement features in accordance with one or more examples.

Figure 18:
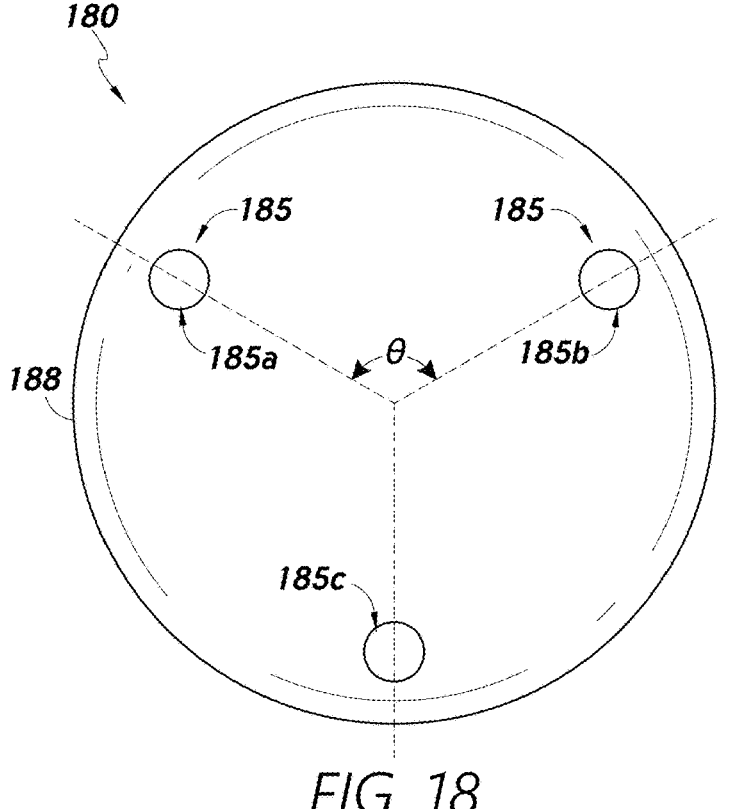

FIG. 18 shows a top or bottom view of a tension-distribution device including three suture-engagement features in accordance with one or more examples.

Figure 19:
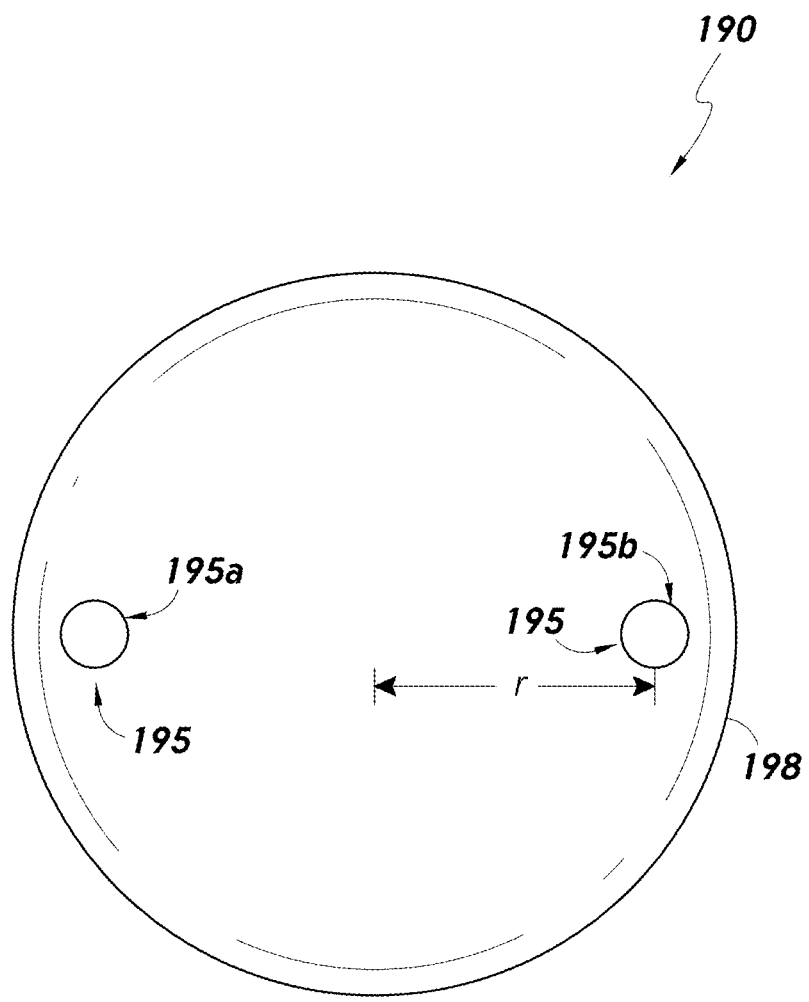

FIG. 19 shows a top or bottom view of a tension-distribution device including two suture-engagement features in accordance with one or more examples.

Figure 20:
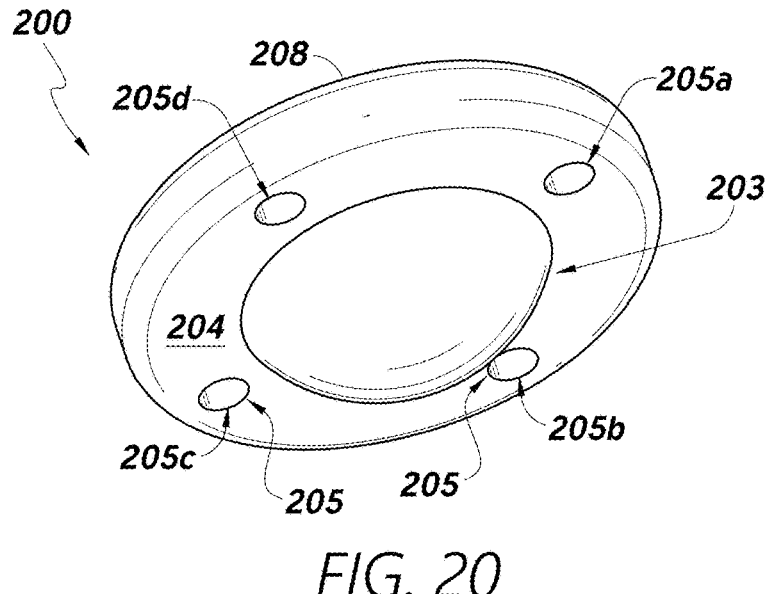

FIG. 20 shows a bottom and side perspective view of a tension-distribution device including a convex projection in accordance with one or more examples.

Figure 1:
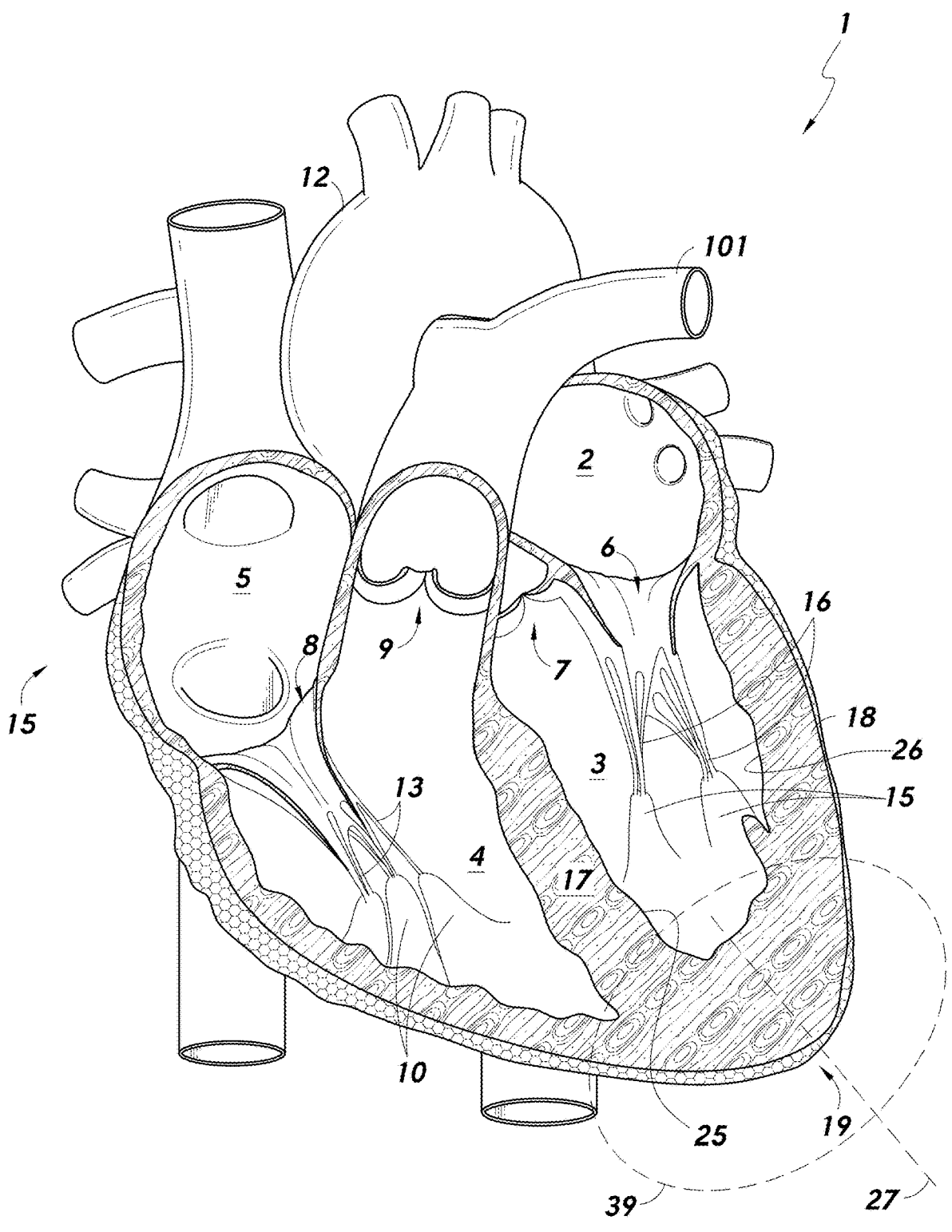
FIG. 1 is a cutaway view of the human heart.
Figure 2:
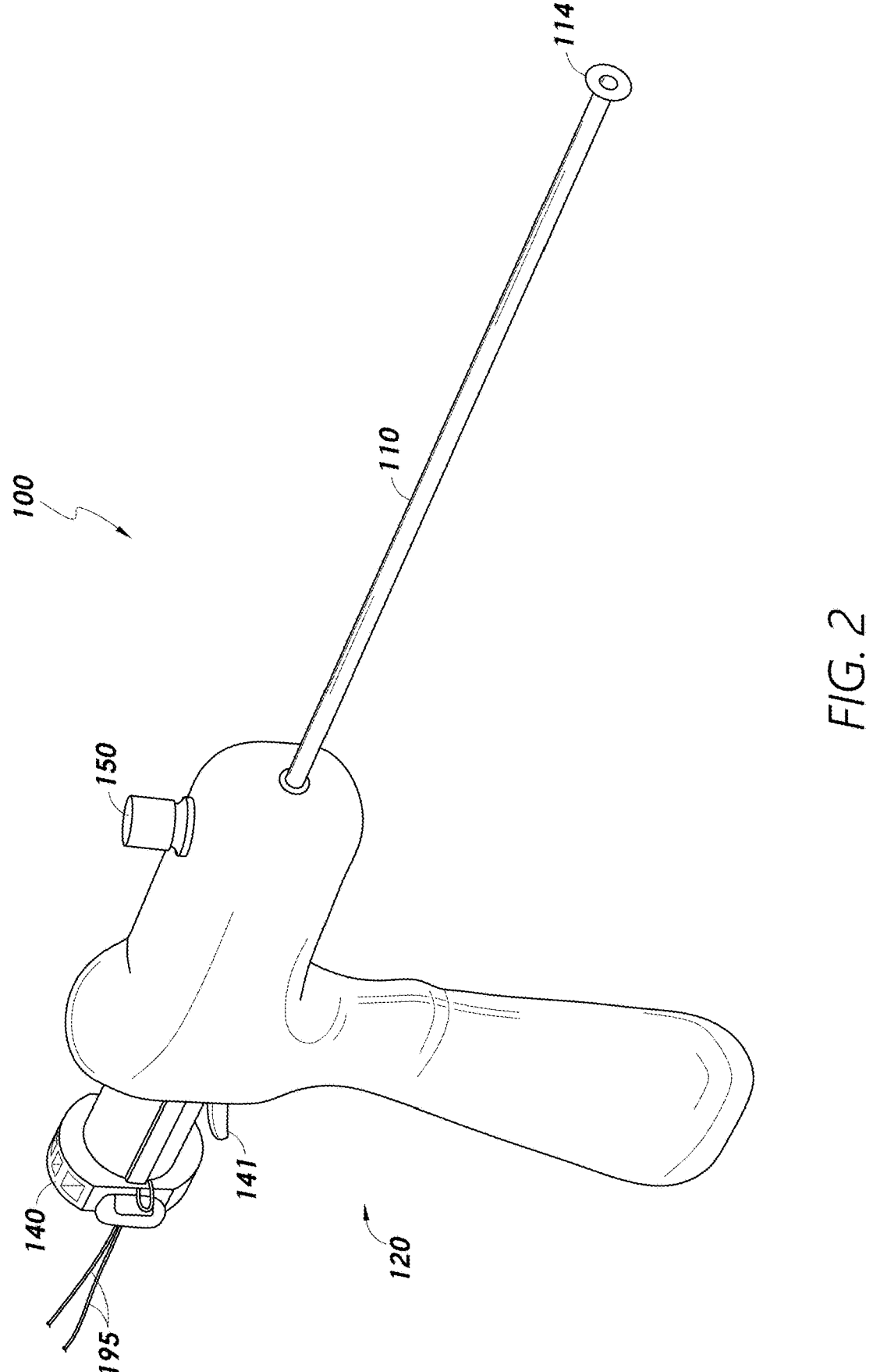
FIG. 2 is a perspective view of a tissue anchor delivery device in accordance with one or more examples.
Figures 1, 21:
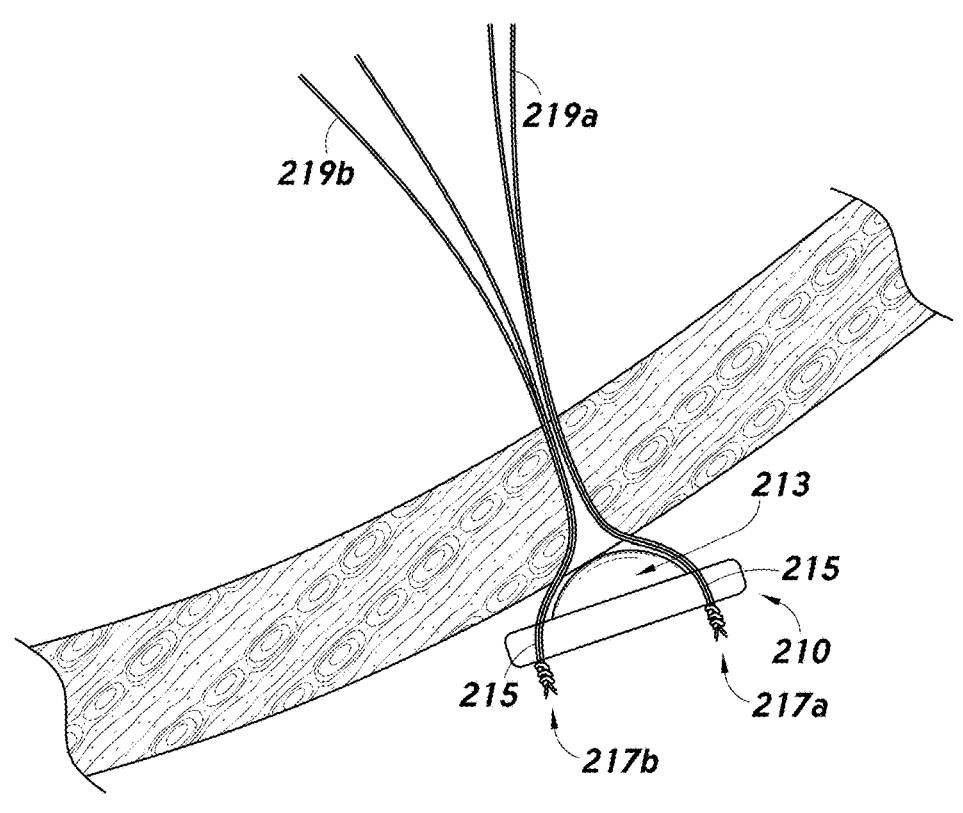
Figures 2, 21:
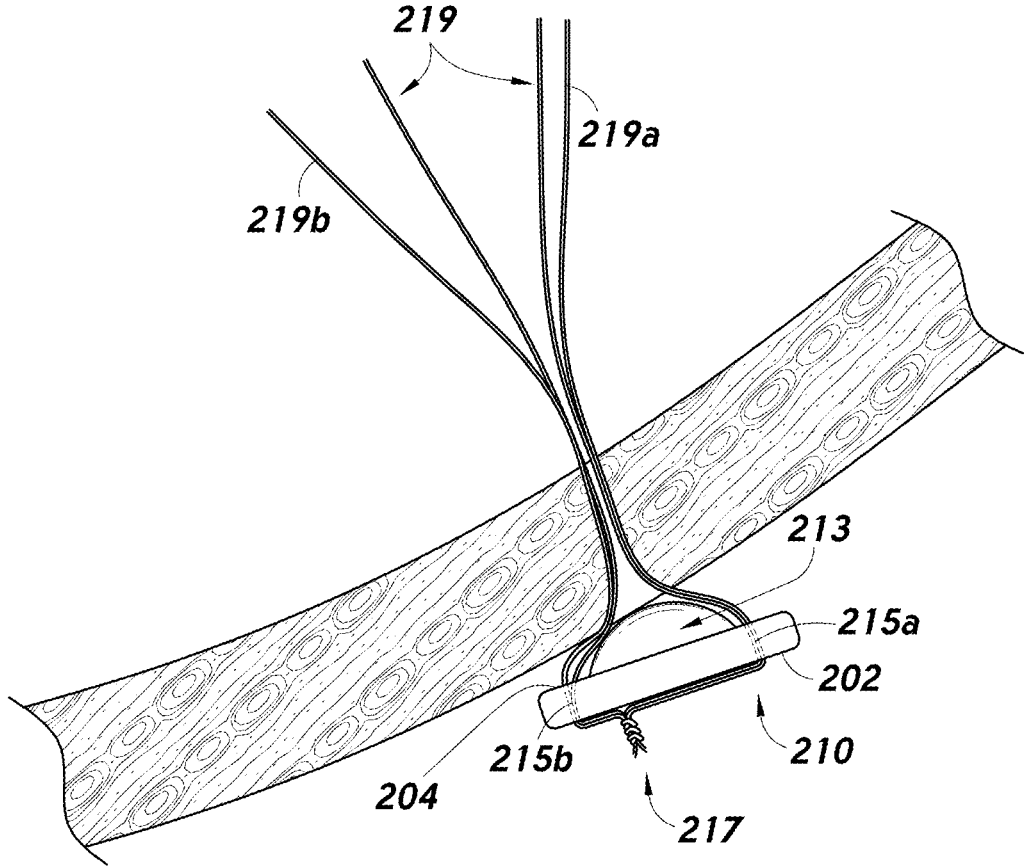

FIGS. 21-1 and 21-2 show side views of tension-distribution devices having a convex projection as implanted in accordance with one or more examples.

Figure 22:
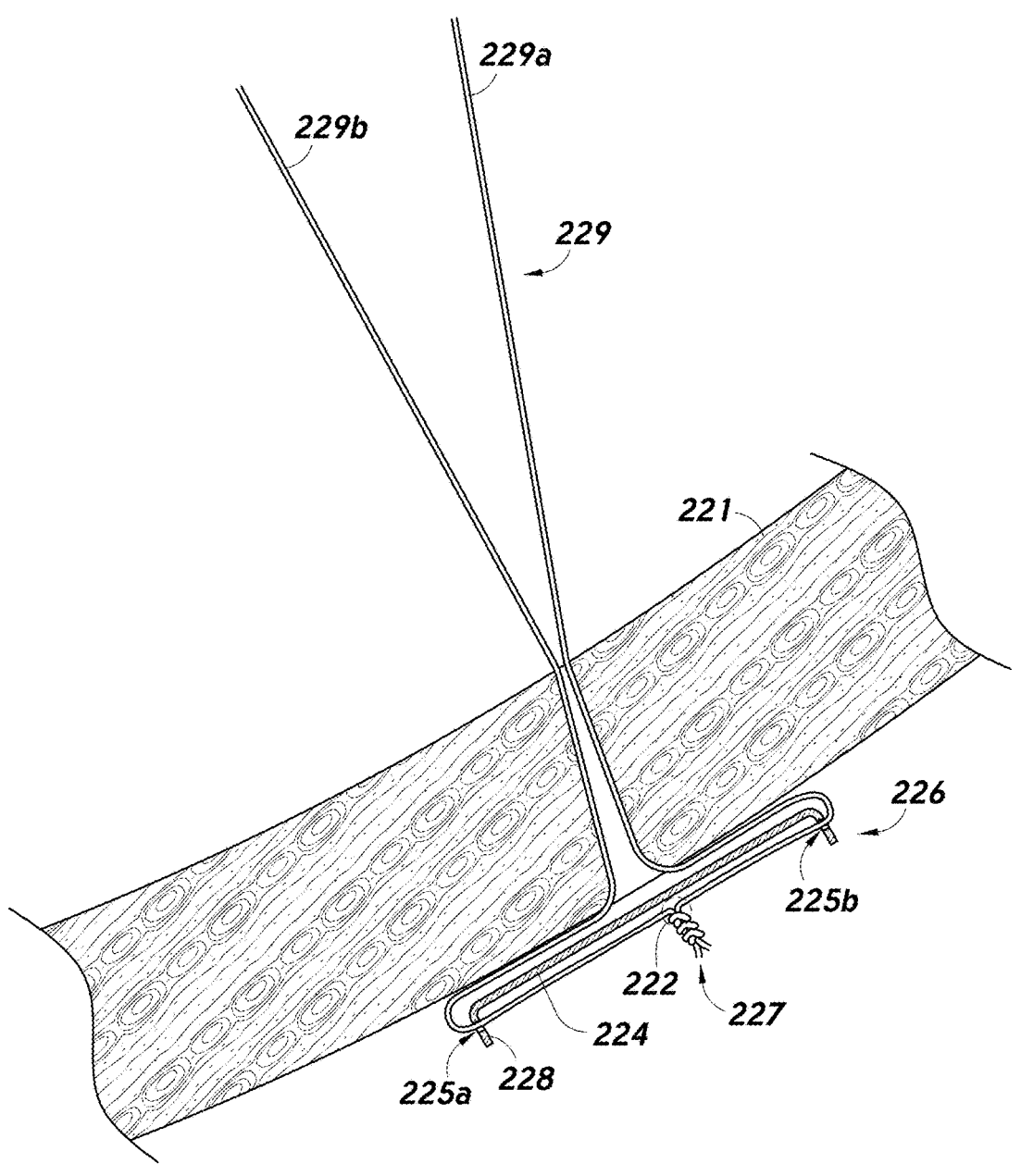

FIG. 22 shows a side view of a tension-distribution device having side suture-engagement features in accordance with one or more examples.

Figure 23:
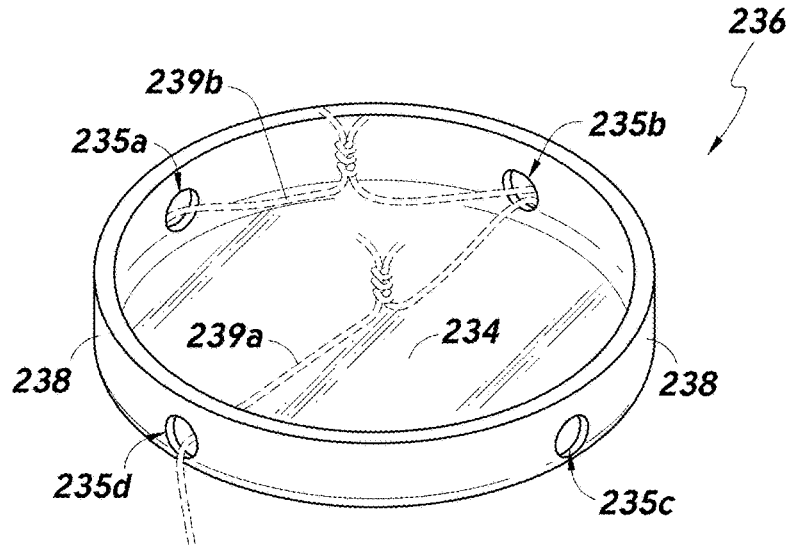

FIG. 23 shows a top and side perspective view of a tension-distribution device having side suture-engagement features in accordance with one or more examples.

Figure 24:
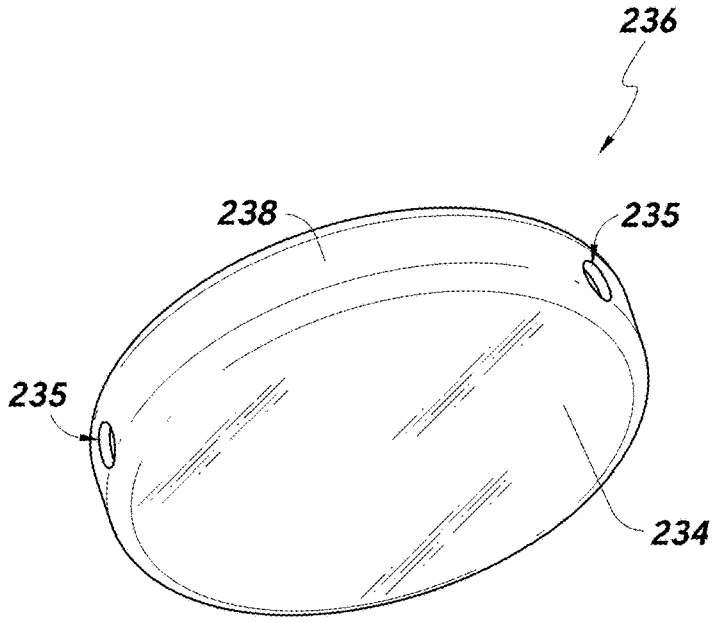

FIG. 24 shows a bottom and side perspective view of the tension-distribution device of FIG. 23 in accordance with one or more examples.

Figure 25:
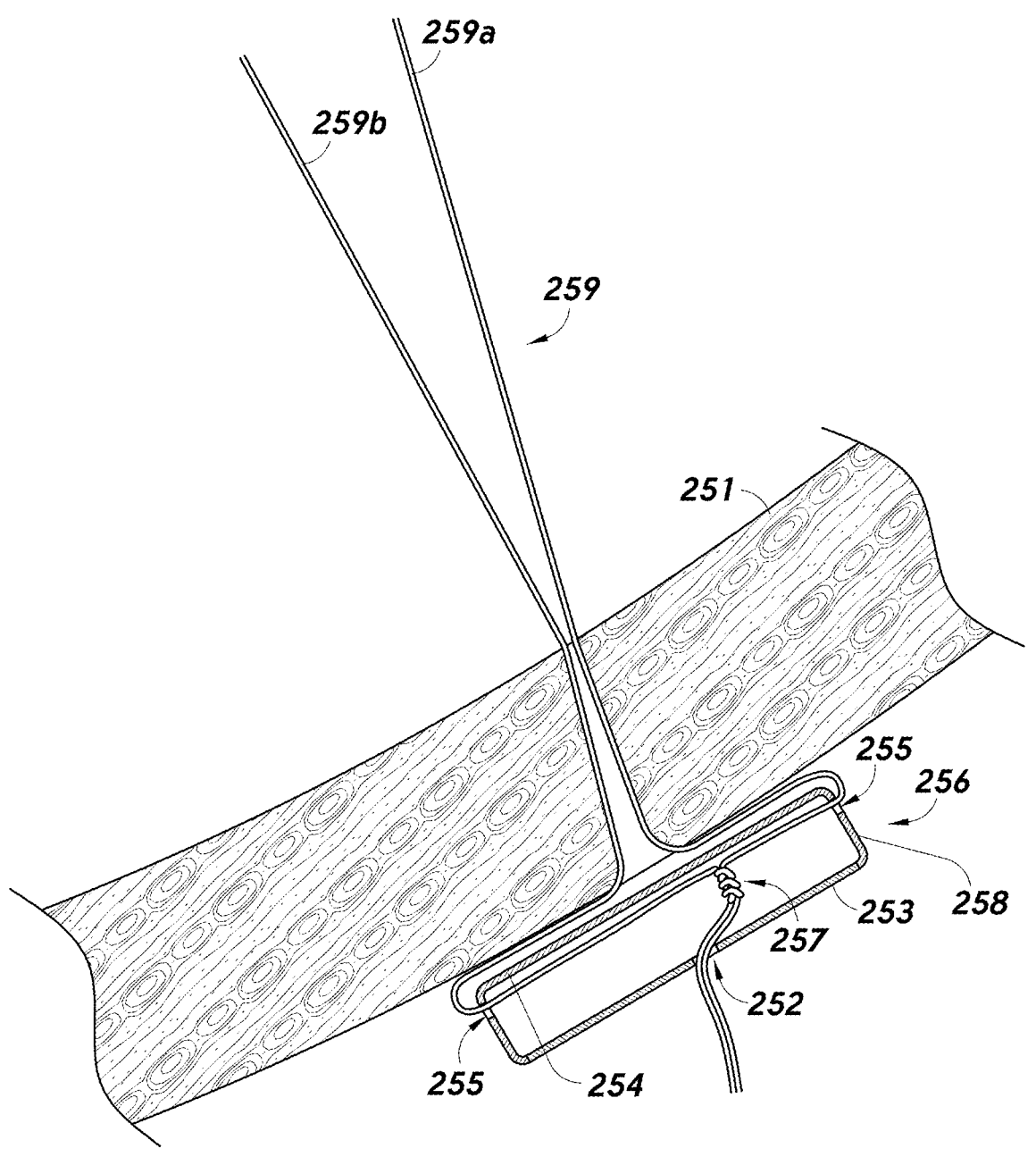

FIG. 25 shows a side view of a tension-distribution device having a cover feature in accordance with one or more examples.

Figure 26:
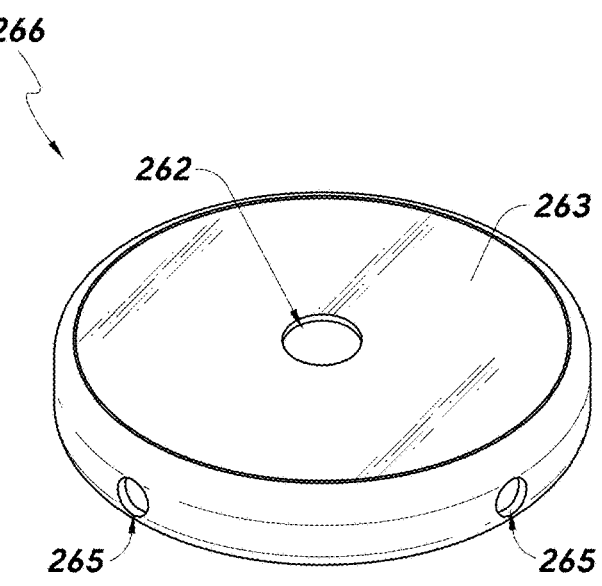

FIG. 26 shows a top and side perspective view of a tension-distribution device having a cover feature in accordance with one or more examples.

5

Figure 27:
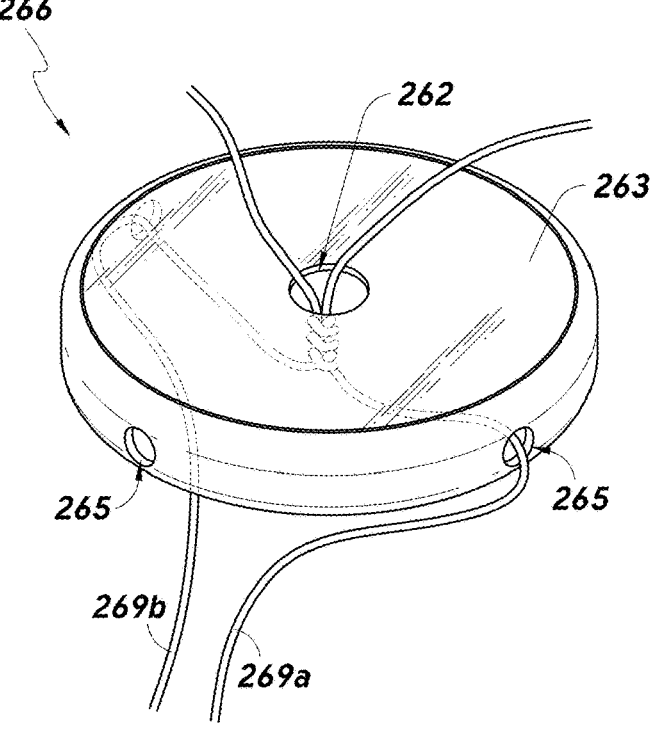

FIG. 27 shows a top and side perspective view of the tension-distribution device of FIG. 26 in accordance with one or more examples.

Figure 28:
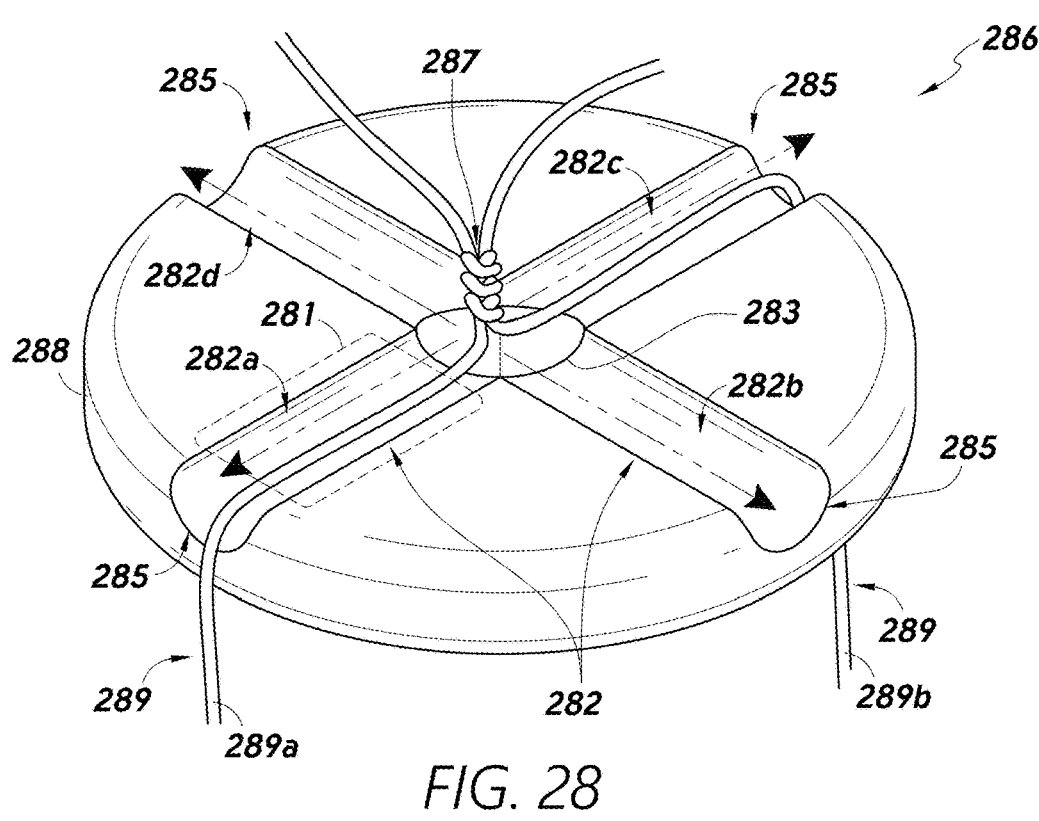

FIG. 28 shows a top and side perspective view of a tension-distribution device having one or more proximal suture channels in accordance with one or more examples.

Figure 29:
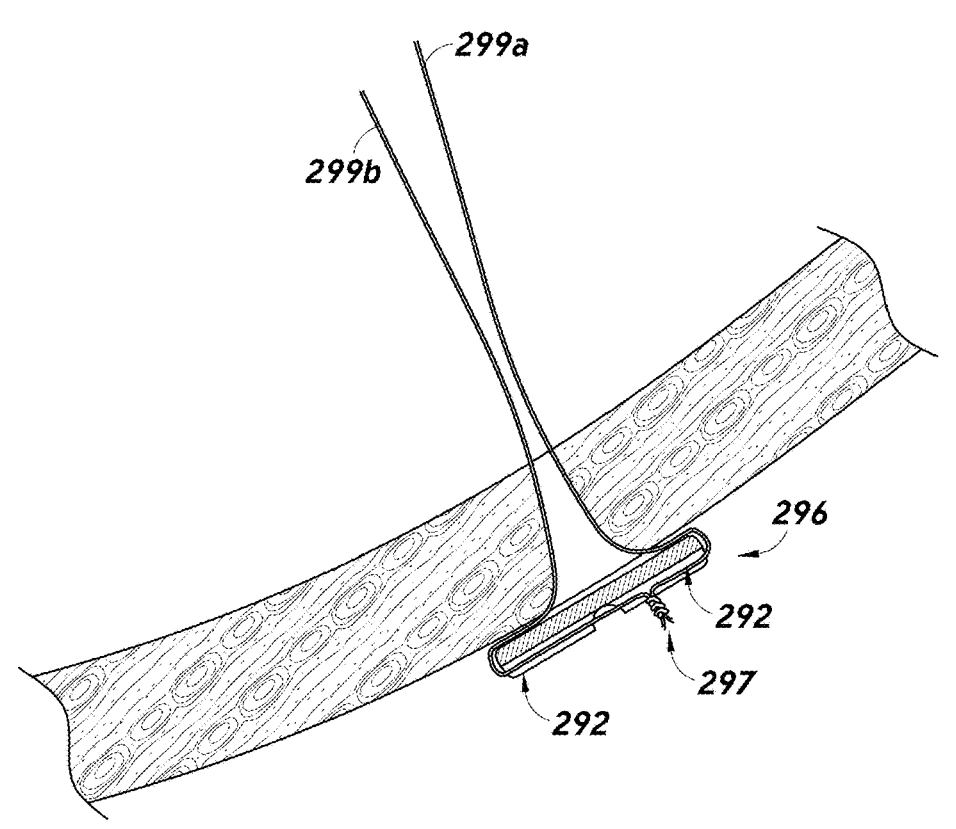

FIG. 29 shows a side view of a tension-distribution device having one or more proximal suture channels with one or more suture portions engaged therewith in accordance with one or more examples.

Figure 30:
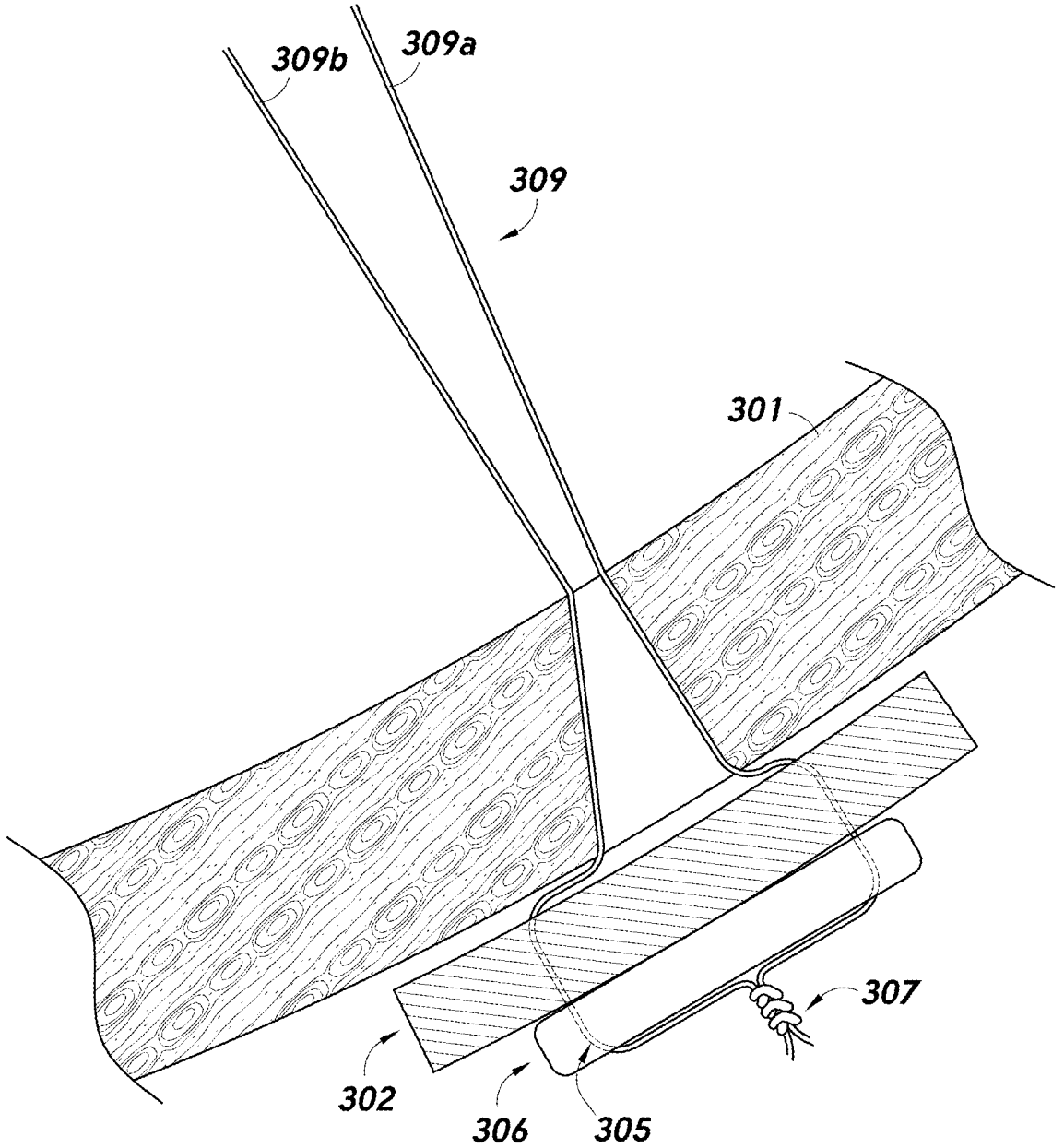

FIG. 30 shows a side view of a tension-distribution device disposed on a pledget in accordance with one or more examples.

Figure 31:
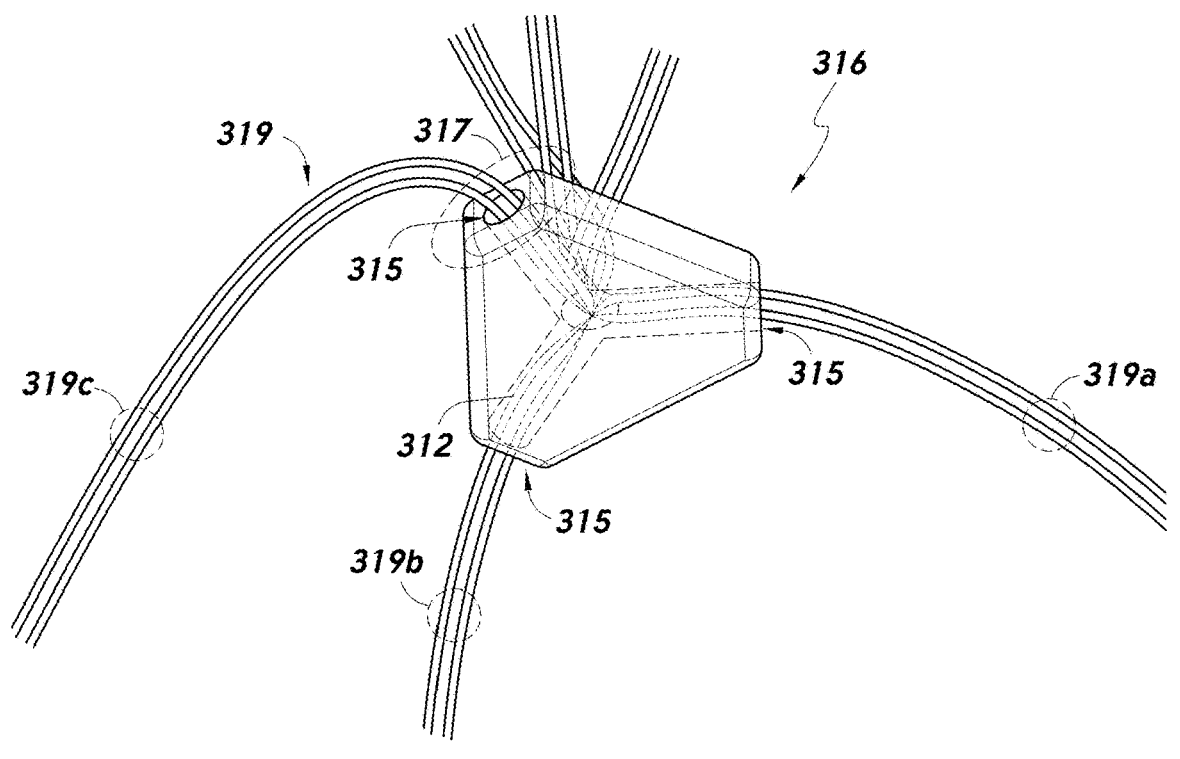

FIG. 31 shows a bottom and side perspective view of a tension-distribution device in accordance with one or more examples.

Figure 32:
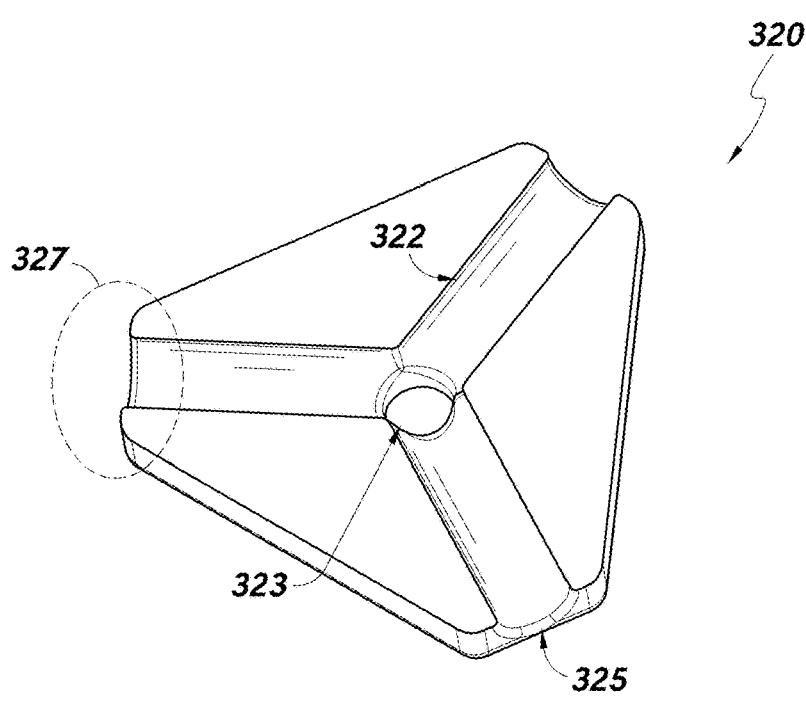

FIG. 32 shows a perspective view of a base of a tension-distribution device in accordance with one or more examples.

Figure 33:
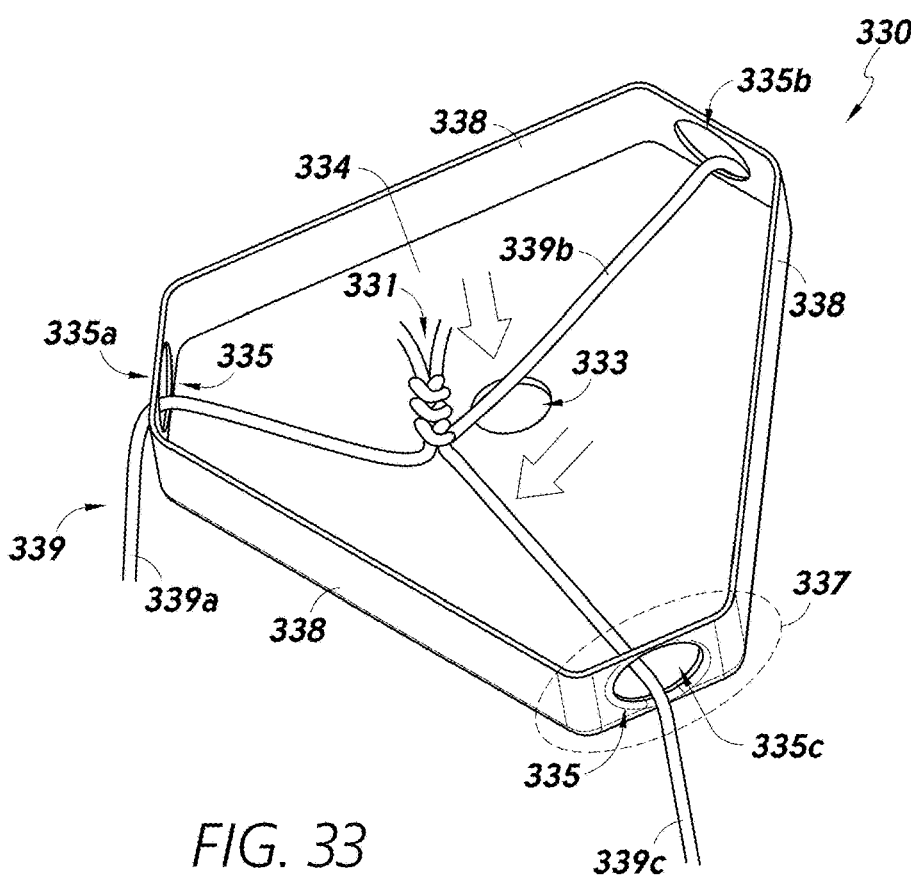

FIG. 33 shows a perspective view of at least a portion of a tension-distribution device in accordance with one or more examples.

Figure 34:
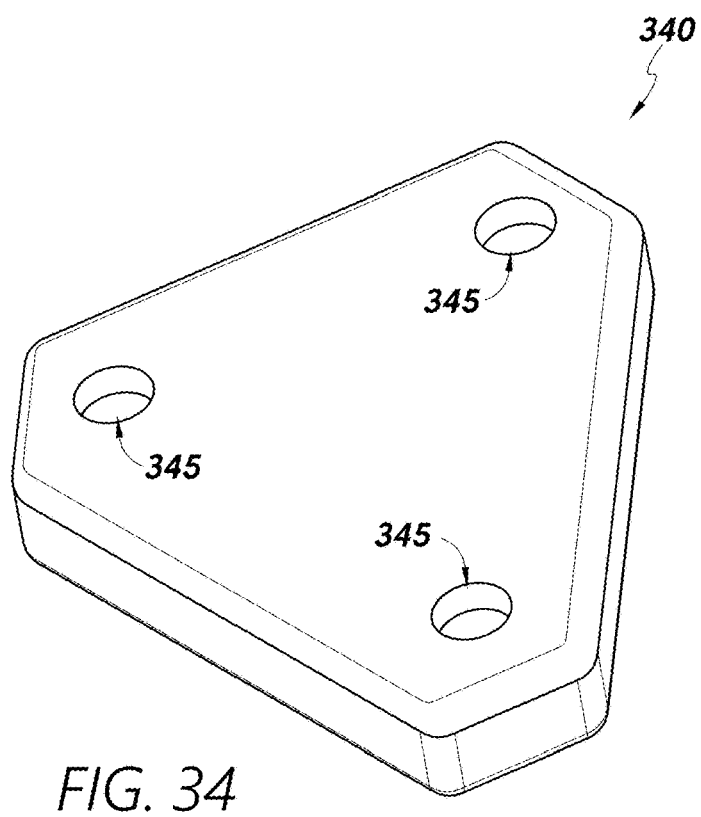

FIG. 34 shows a bottom and side perspective view of at least a portion of a tension-distribution device in accordance with one or more examples.

Figure 35:
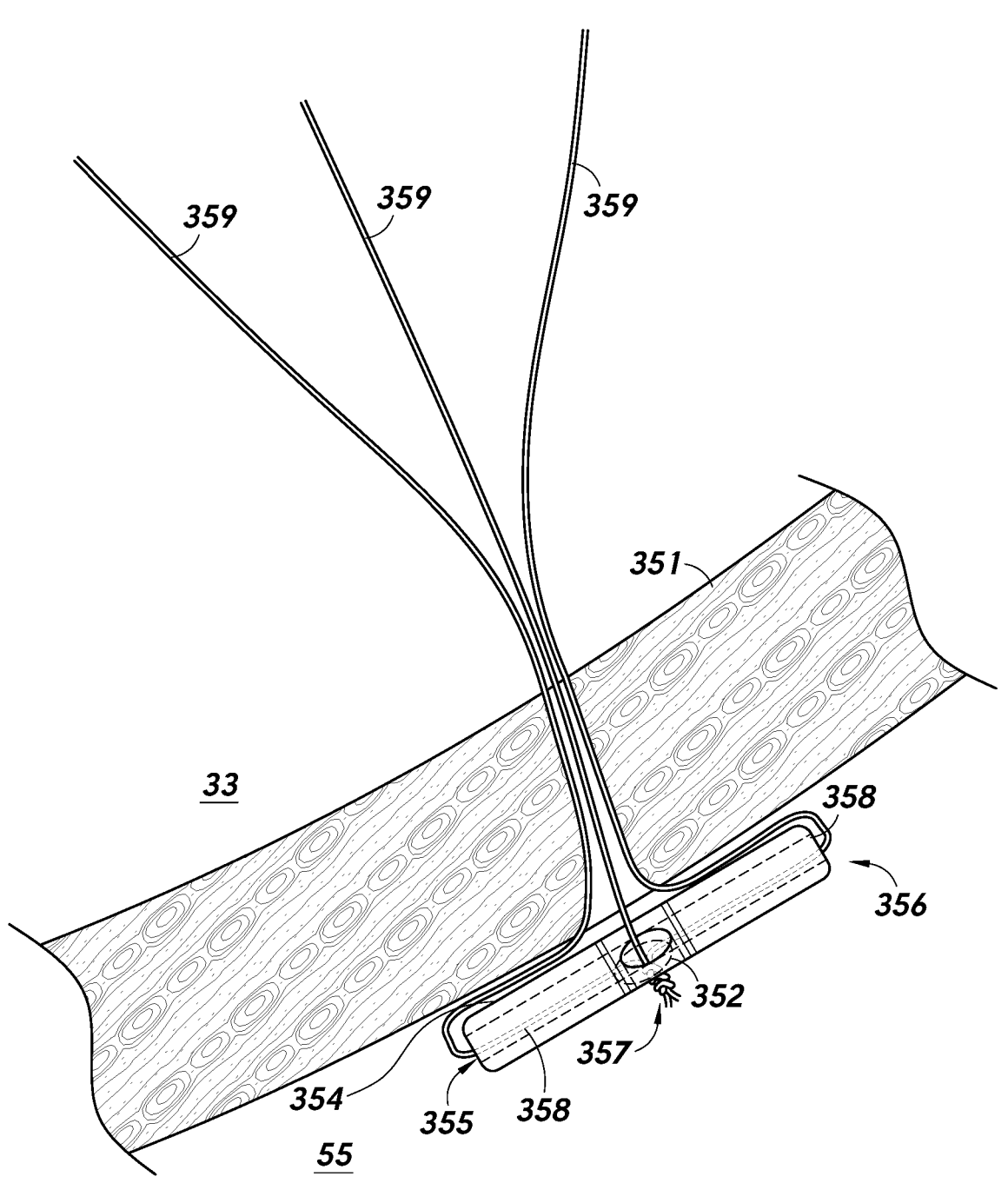

FIG. 35 shows a side view of a tension-distribution device having a plurality of suture portions engaged therewith accordance with one or more examples.

Figure 36:
Figure 36:
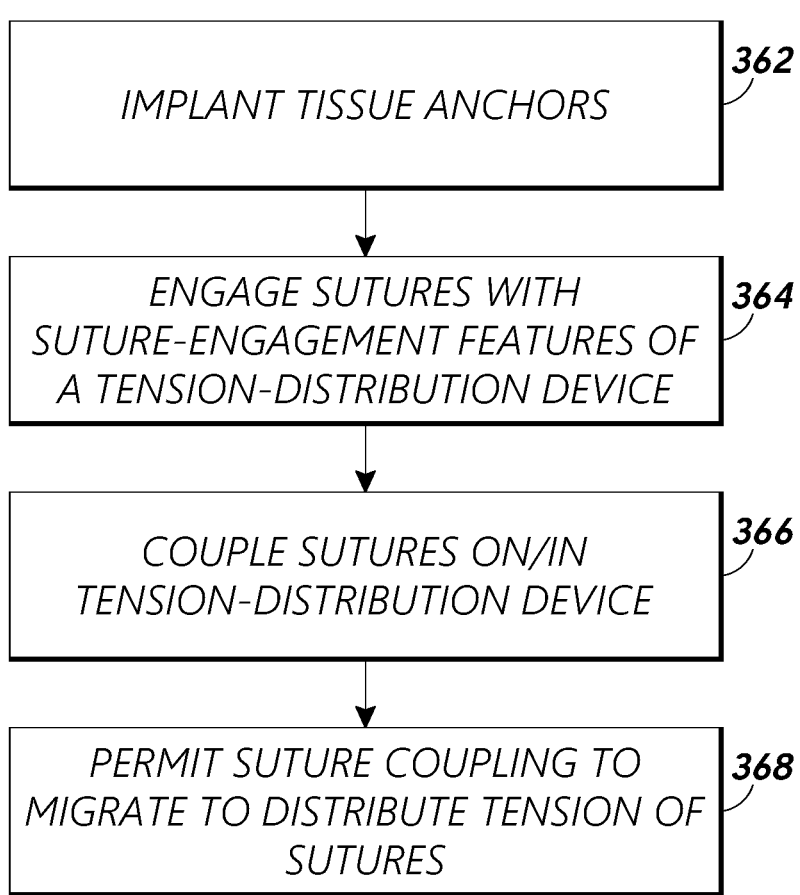
Figure 37:
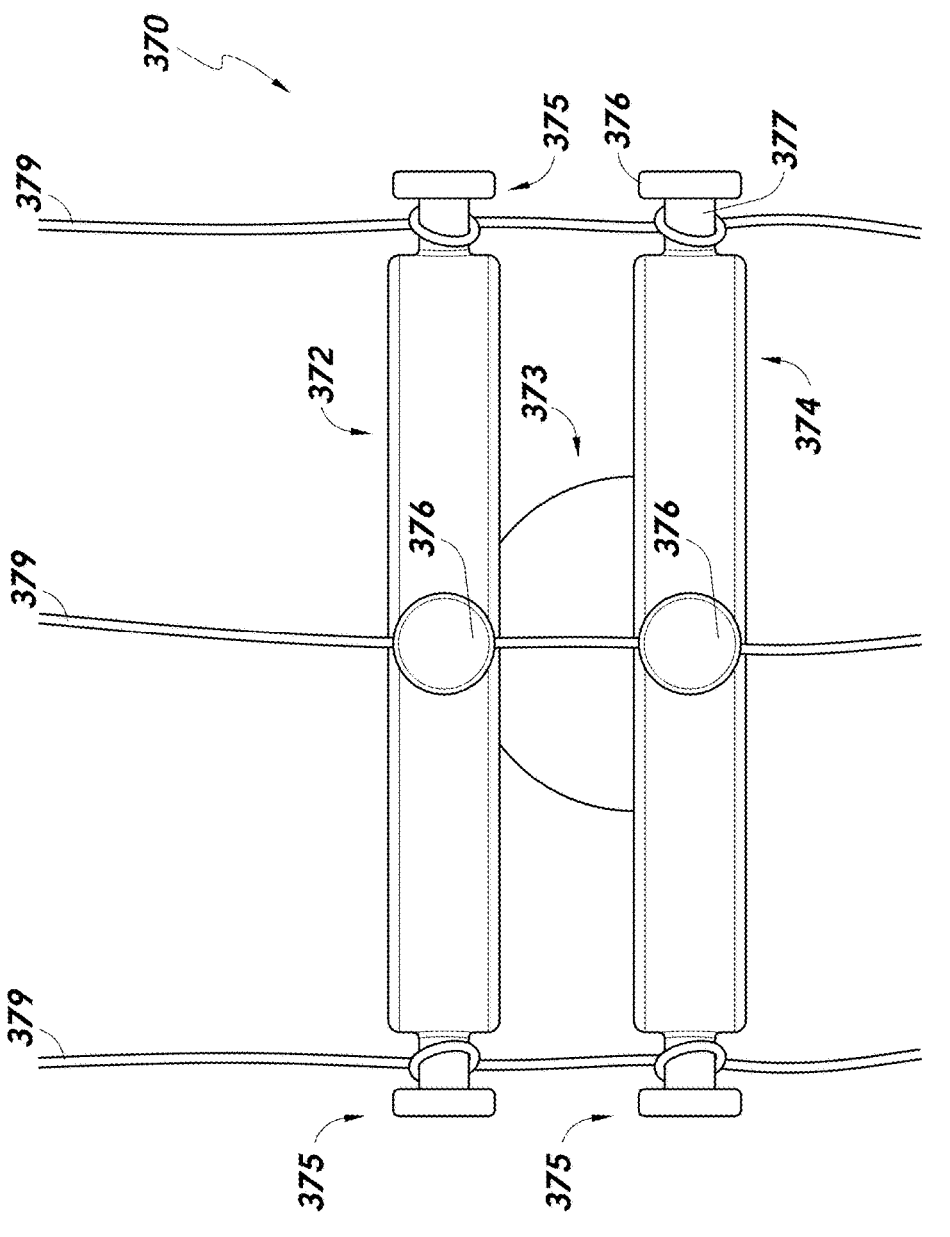

FIG. 36 is a flow diagram illustrating a process for distributing or balancing tension among a plurality of suture portions and/or groupings of suture portions in accordance with one or more examples FIG. 37 shows a side view of a tension-balancing device in accordance with one or more examples.

Figure 38:
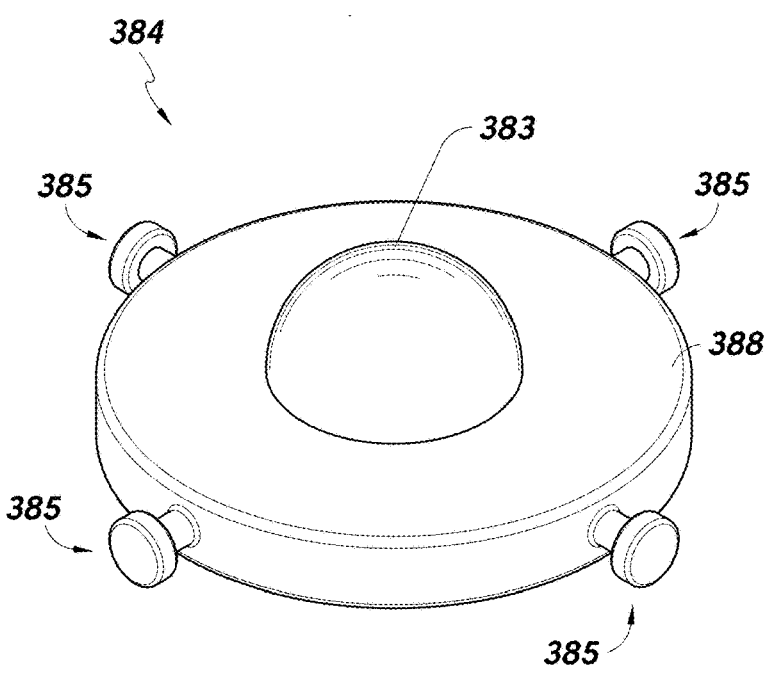

FIG. 38 shows a base portion of a tension-balancing device in accordance with one or more examples.

Figure 39:
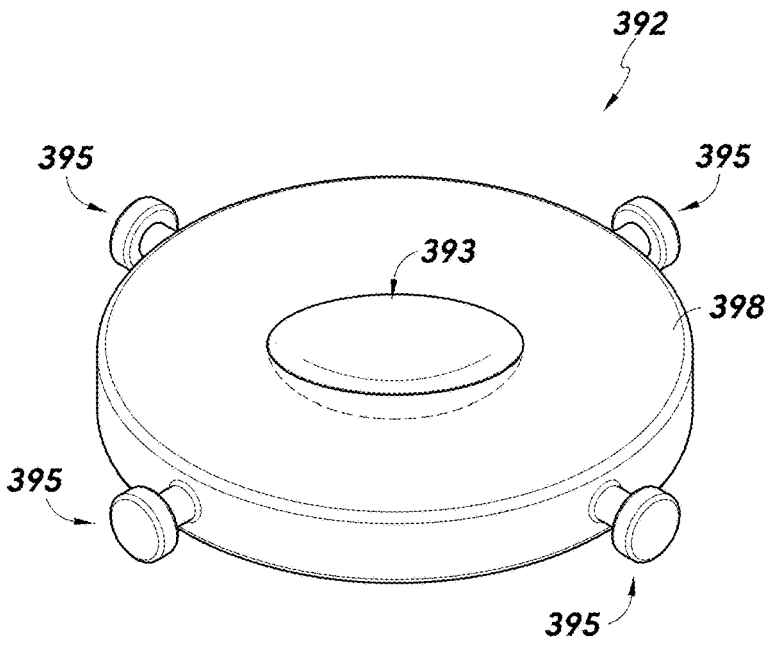

FIG. 39 shows a perspective view of a balancer portion of a tension-balancing device in accordance with one or more examples.

Figures 40, 41, 42:
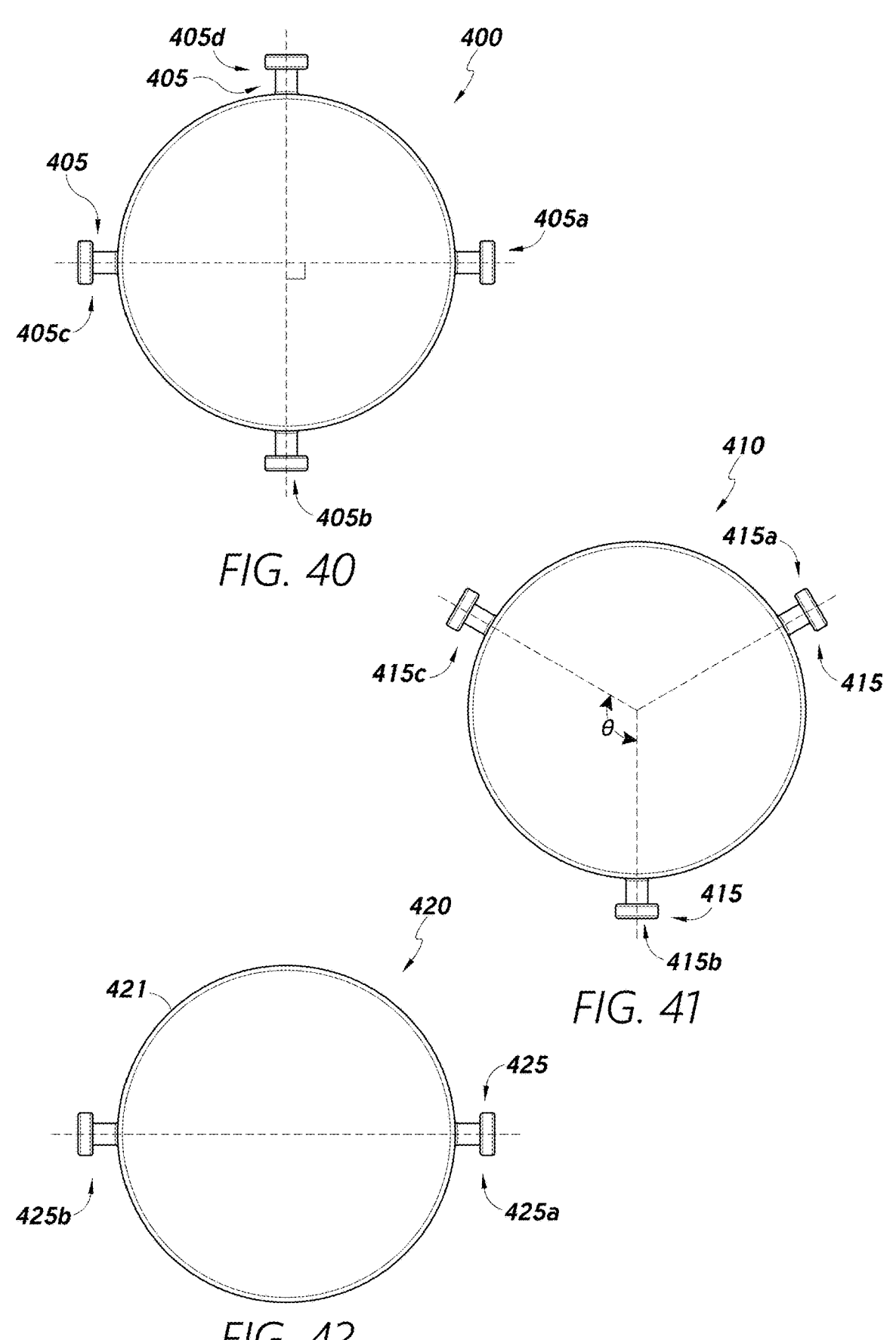

FIG. 40 shows a component of a tension-balancing device including four suture-fixation features in accordance with one or more examples.

FIG. 41 shows a component of a tension-balancing device including three suture-fixation features in accordance with one or more examples.

FIG. 42 shows a component of a tension-balancing device including two suture-fixation features in accordance with one or more examples.

Figure 43:
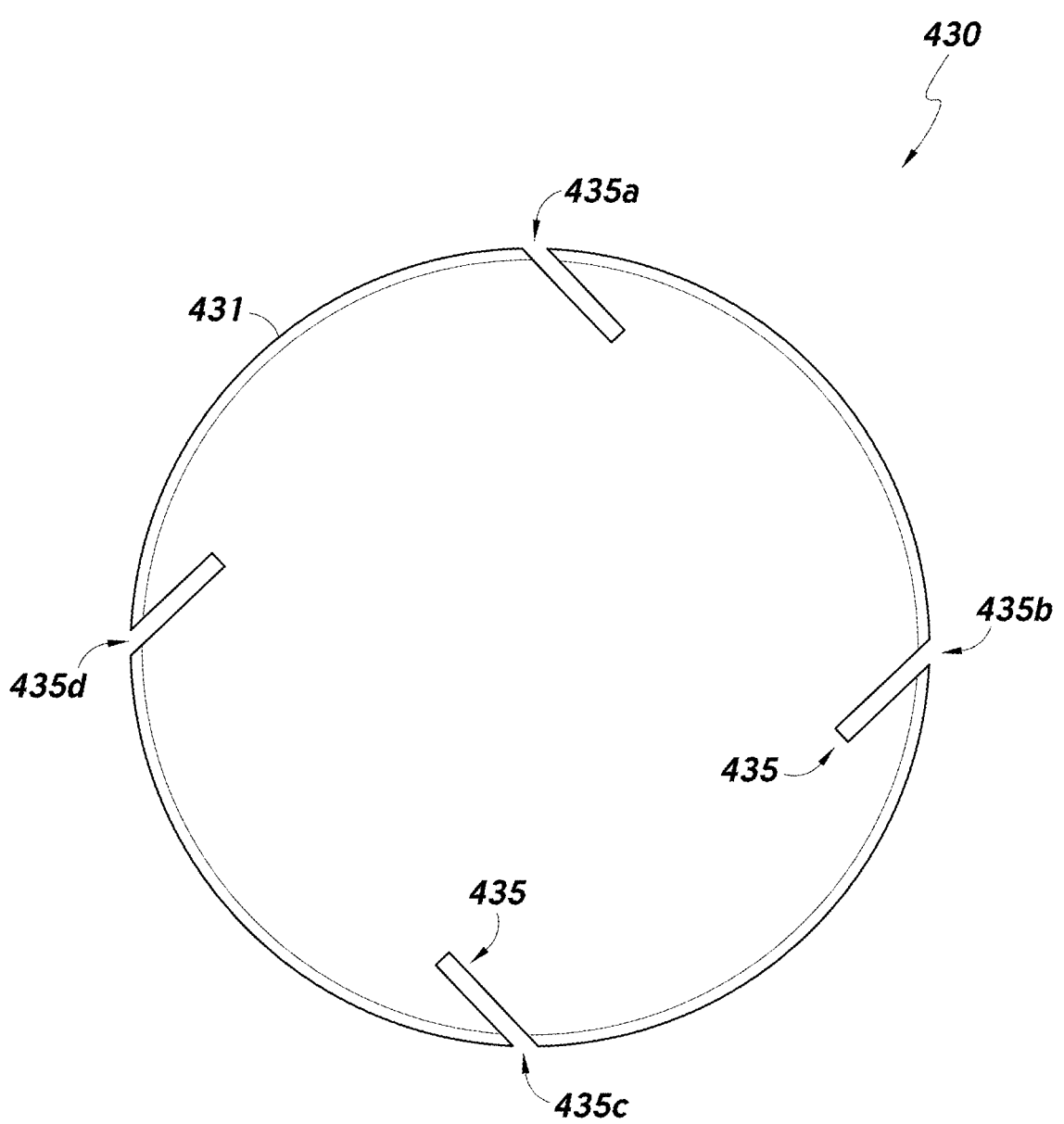

FIG. 43 shows a component of a tension-balancing device including slit-type suture-fixation features in accordance with one or more examples.

FIGS. 44-48 show side and perspective views, respectively, of aspects of a tension-balancing device subject to various suture tension conditions in accordance with one or more examples.

Figures 2, 49, 50:
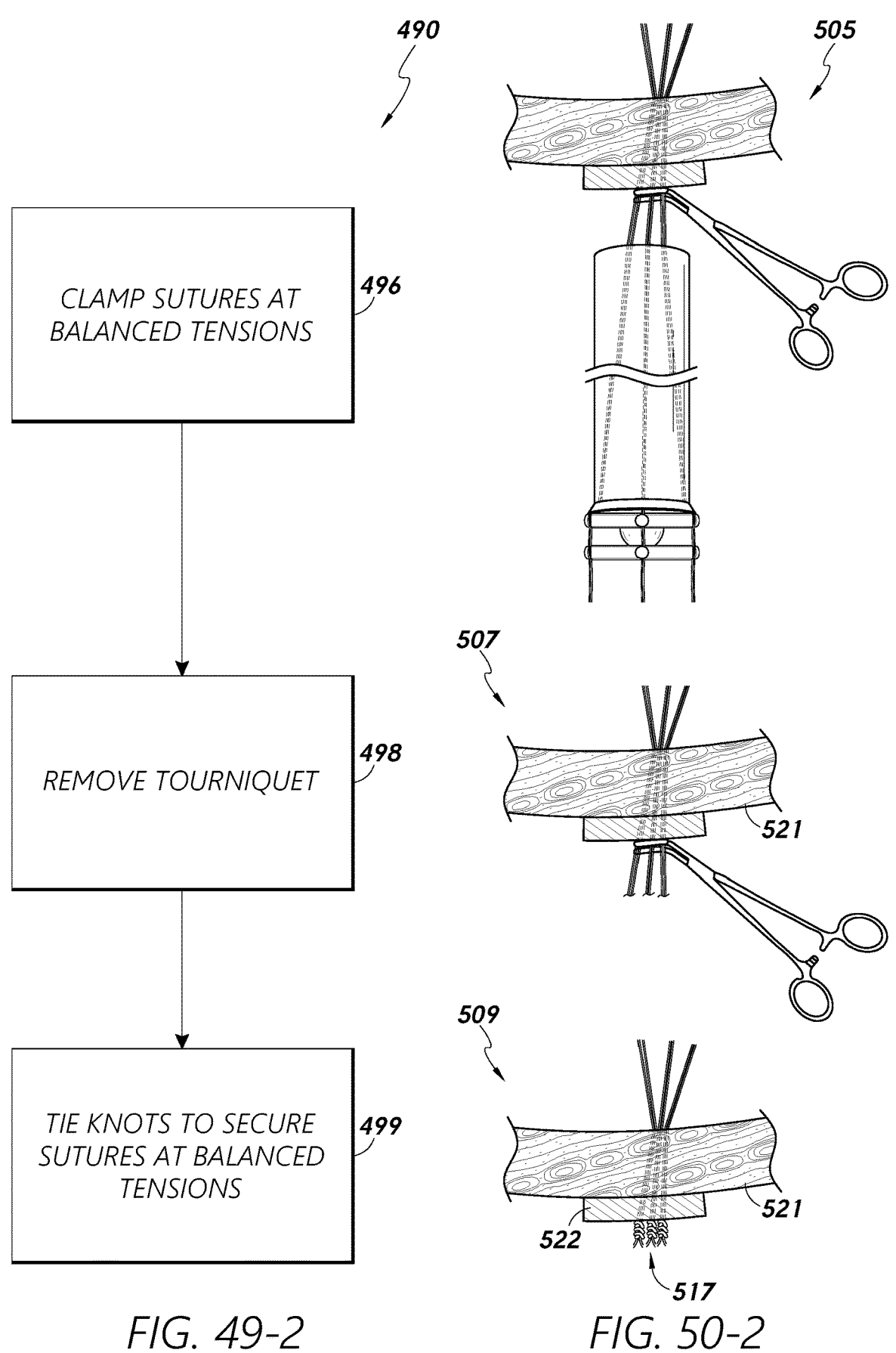

FIGS. 49-1 and 49-2 show a flow diagram illustrating a process for tensioning sutures in accordance with one or more examples.

FIGS. 50-1 and 50-2 show certain images corresponding to respective blocks, states, and/or operations associated with the process of FIGS. 49-1 and 49-2 in accordance with one or more examples.

To further clarify various aspects of examples of the present disclosure, a more particular description of certain examples will be made by reference to various aspects of the appended drawings. It is appreciated that these drawings depict only typical examples of the present disclosure and are therefore not to be considered limiting of the scope of the disclosure. Moreover, while the figures can be drawn to scale for some instances, the figures are not necessarily drawn to scale for all examples. Examples of the present disclosure will be described and explained with additional specificity and detail through the use of the accompanying drawings.

DETAILED DESCRIPTION

The following description refers to the accompanying drawings, which illustrate specific examples. Other examples having different structures and operation do not depart from the scope of the disclosure. Examples of the present disclosure relate to devices and methods for distributing and/or balancing pensions of sutures or suture portions. For example, some instances of the present disclosure relate to distribution/balancing of suture portions associated with tissue anchors (e.g., suture knots) deployed in connection with, for example, a heart valve repair procedure, such as mitral valve repair, which may be performed on a beating heart according to some implementations. With respect to delivery devices and systems used to deliver such tissue anchors, such delivery devices/systems may be referred to herein as tissue anchor delivery devices/systems and/or valve repair devices/systems.

Disclosed herein are suture tension balancing/distribution devices, which can have a button-like shape or form. The devices can be used to ensure or promote the even distribution of tension across sutures (e.g., suture portions) implanted in biological tissue, such as one or more valve leaflets (e.g., mitral or tricuspid valve leaflets). Proper suture tension balancing can advantageously reduce the risk of postoperative suture rupture under tension. In some instances, suture-tension balancing/distribution devices can facilitate the further self-balancing of implanted sutures post-procedure, which may be helpful in the event that patient heart conditions change or when residual tension differences exist on sutures after implantation thereof.

In some instances, suture tension-distribution devices can comprise a plurality of suture-engagement features (e.g., portals) configured to allow opposing sutures to be connected/coupled to each other. In the event that one suture gains higher tension over time, devices can be configured to pull on the opposing suture to re-distribute the tension load to the less-tensioned suture(s), thereby potentially prolonging the effectiveness of the relevant procedure.

The suture-engagement features can be embedded in the suture tension-distribution device and configured to allow sutures to be fished therethrough. For example, a pair of sutures, or other grouping of sutures, can be connected/coupled together through the suture-engagement features to allow one suture (or group of sutures) to pull on one or more opposing sutures (or groups of sutures) when gaining tension. Such pulling action can allow for gained tension to be distributed by the coupled sutures evenly.

The following includes a general description of human cardiac anatomy that is relevant to certain inventive features and examples disclosed herein and is included to provide context for certain aspects of the present disclosure. In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

FIG. 1 illustrates an example representation of a heart 1 having various features relevant to certain aspects of the present inventive disclosure. The heart 1 includes four chambers, namely the left ventricle 3, the left atrium 2, the right ventricle 4, and the right atrium 5. A wall of muscle 17, referred to as the septum, separates the left 2 and right 5 atria and the left 3 and right 4 ventricles. The inferior tip 19 of the heart 1 is referred to as the apex and is generally located on the midclavicular line, in the fifth intercostal space. The apex 19 can be considered part of the greater apical region 39.

The left ventricle 3 is the primary pumping chamber of the heart 1. A healthy left ventricle is generally conical or apical in shape in that it is longer (along a longitudinal axis extending in a direction from the aortic valve 7 to the apex 19) than it is wide (along a transverse axis extending between opposing walls 25, 26 at the widest point of the left ventricle) and descends from a base 15 with a decreasing cross-sectional circumference to the point or apex 19. Generally, the apical region 39 of the heart is a bottom region of the heart that is within the left or right ventricular region but is distal to the mitral 6 and tricuspid 8 valves and toward the tip of the heart. More specifically, the apical region 39 may be considered to be within about 20 cm to the right or to the left of the median axis 27 of the heart 1.

The pumping of blood from the left ventricle is accomplished by a squeezing motion and a twisting or torsional motion. The squeezing motion occurs between the lateral wall 18 of the left ventricle and the septum 17. The twisting motion is a result of heart muscle fibers that extend in a circular or spiral direction around the heart. When these fibers contract, they produce a gradient of angular displacements of the myocardium from the apex 19 to the base 15 about the longitudinal axis of the heart. The resultant force vectors extend at angles from about 30-60 degrees to the flow of blood through the aortic valve 7. The contraction of the heart is manifested as a counterclockwise rotation of the apex 19 relative to the base 15, when viewed from the apex 19. A healthy heart can pump blood from the left ventricle in a very efficient manner due to the spiral contractility of the heart.

The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (e.g., systole) and open during ventricular expansion (e.g., diastole). The valves of the heart 1 further include the pulmonary valve 9, which separates the right ventricle 4 from the pulmonary artery 101 and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The atrioventricular (e.g., mitral and tricuspid) heart valves may comprise a collection of chordae tendineae (13, 16) and papillary muscles (10, 15) for securing the leaflets of the respective valves to promote and/or facilitate proper coaptation of the valve leaflets and prevent prolapse thereof. The papillary muscles, for example, may generally comprise finger-like projections from the ventricle wall. With respect to the tricuspid valve 8, the normal tricuspid valve may comprise three leaflets and three corresponding papillary muscles 10 (two shown in FIG. 1). The leaflets of the tricuspid valve may be referred to as the anterior, posterior and septal leaflets, respectively. The valve leaflets are connected to the papillary muscles 10 by the chordae tendineae 13, which are disposed in the right ventricle 4 along with the papillary muscles 10.

Surrounding the ventricles (3, 4) are a number of arteries (not shown) that supply oxygenated blood to the heart muscle and a number of veins that return the blood from the heart muscle. The coronary sinus (not shown) is a relatively large vein that extends generally around the upper portion of the left ventricle 3 and provides a return conduit for blood returning to the right atrium 5. The coronary sinus terminates at the coronary ostium (not shown) through which the blood enters the right atrium.

With respect to the mitral valve 6, a normal mitral valve may comprise two leaflets (anterior and posterior) and two corresponding papillary muscles 15. The papillary muscles 15 originate in the left ventricle wall and project into the left ventricle 3. Generally, the anterior leaflet may cover approximately two-thirds of the valve annulus. Although the anterior leaflet covers a greater portion of the annulus, the posterior leaflet may comprise a larger surface area in certain anatomies.

Various disease processes can impair the proper functioning of one or more of the valves of the heart. These disease processes include degenerative processes (e.g., Barlow's Disease, fibroelastic deficiency), inflammatory processes (e.g., Rheumatic Heart Disease) and infectious processes (e.g., endocarditis). Additionally, damage to the ventricle from prior heart attacks (e.g., myocardial infarction secondary to coronary artery disease) or other heart diseases (e.g., cardiomyopathy) can distort the valve's geometry causing it to dysfunction. However, the vast majority of patients undergoing valve surgery, such as mitral valve surgery, suffer from a degenerative disease that causes a malfunction in one or more leaflets of the valve which results in prolapse and regurgitation.

The mitral valve 6 and tricuspid valve 8 can be divided into three parts: an annulus, leaflets, and a sub-valvular apparatus. The sub-valvular apparatus can be considered to include the papillary muscles 10, 15 and the chordae tendineae 13, 16, which can elongate and/or rupture. If a valve is functioning properly, when closed, the free margins or edges of the leaflets come together and form a tight junction, the arc of which, in the mitral valve, is known as the line, plane or area of coaptation. Normal mitral and tricuspid valves open when the ventricles relax allowing blood from the atrium to fill the decompressed ventricle. When the ventricle contracts, the chordae tendineae advantageously properly tether or position the valve leaflets such that the increase in pressure within the ventricle causes the valve to close, thereby preventing blood from leaking into the atrium and assuring that substantially all of the blood leaving the ventricle is ejected through the aortic valve 7 or pulmonic valve 9 and into the arteries of the body. Accordingly, proper function of the valves depends on a complex interplay between the annulus, leaflets, and sub-valvular apparatus. Lesions in any of these components can cause the valve to dysfunction and thereby lead to valve regurgitation.

Generally, there are three mechanisms by which a heart valve becomes regurgitant or incompetent; they include Carpentier's type I, type II and type III malfunctions. A Carpentier type I malfunction involves the dilation of the annulus such that normally functioning leaflets are distracted from each other and fail to form a tight seal (e.g., do not coapt properly). Included in a type I mechanism malfunction are perforations of the valve leaflets, as in endocarditis. A Carpentier's type II malfunction involves prolapse of one or both leaflets above the plane of coaptation. This is the most common cause of mitral regurgitation and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic disease (IIIa) or dilation of the ventricle (IIIb).

One or more chambers in the heart 1 may be accessed in accordance with certain heart valve-repair procedures and/or other interventions. Access into a chamber in the heart may be made at any suitable site of entry. In some implementations, access is made to a chamber of the heart, such as a target ventricle (e.g., left ventricle) associated with a diseased heart valve, through the apical region 39. For example, access into the left ventricle 3 (e.g., to perform a mitral valve repair) may be gained by making a relatively small incision at the apical region 39, close to (or slightly skewed toward the left of) the median axis 27 of the heart. Access into the right ventricle 4 (e.g., to perform a tricuspid valve repair) may be gained by making a small incision into the apical region 39, close to or slightly skewed toward the right of the median axis 27 of the heart. Accordingly, the ventricle can be accessed directly via the apex, or via an off-apex location that is in the apical region 39 but slightly removed from the tip/apex, such as via lateral ventricular wall, a region between the apex and the base of a papillary muscle, or even directly at the base of a papillary muscle. In some implementations, the incision made to access the appropriate ventricle of the heart is no longer than about 1 mm to about 5 cm, from 2.5 mm to about 2.5 cm, or from about 5 mm to about 1 cm in length. When a percutaneous approach is sought, no incision into the apex region of the heart may be made, but rather access into the apical region 39 may be gained by direct needle puncture, for instance by an 18-gauge needle, through which an appropriate repair instrument can be advanced.

Certain inventive features disclosed herein relate to the tensioning of sutures and/or suture portions associated with certain heart valve repair systems and devices, and/or systems, process, and devices for repairing any other type of target organ tissue. The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, or otherwise physically related to the second feature, element, component, device, or member.

In some implementations, a tissue anchor delivery device associated with one or more suture tails/portions that require tension balancing in accordance with aspects of the present disclosure may be employed in repairing a mitral valve in a patient suffering from degenerative mitral regurgitation or other condition. In some implementations, a transapical off-pump echo-guided repair procedure is implemented in which at least part (e.g., a shaft portion/assembly) of a valve repair system is inserted in the left ventricle and steered to the surface of the diseased portion of a target mitral valve leaflet and used to deploy/implant a tissue anchor in the target leaflet.

The tissue anchor (e.g., sutureform formed into a bulky knot) may advantageously be integrated or coupled with one or more artificial/synthetic cords serving a function similar to that of chordae tendineae. Such artificial cord(s) may comprise suture(s) and/or suture tail portions associated with a knot-type tissue anchor and may comprise any suitable or desirable material, such as expanded polytetrafluoroethylene (ePTFE) or the like. The term "suture" is used herein according to its broad and ordinary meaning and may refer to any elongate cord, strip, strand, line, tie, string, ribbon, strap, or portion thereof, or other type of material used in medical procedures (e.g., ePTFE suture, for example, GORE-TEX® sutures, W. L. Gore, Newark, Delaware). One having ordinary skill in the art will understand that a wire or other similar material may be used in place of a suture. Furthermore, in some contexts herein, the terms "cord," "chordae," "suture portion," and "suture" may be used substantially interchangeably. In addition, use of the singular form of any of the suture-related terms listed above, including the terms "suture" and "cord," may be used to refer to a single suture/cord, or to a portion thereof. For example, where a suture knot or anchor is deployed and where two suture portions/tails extend from the knot/anchor, either of the suture portions may be referred to as a "suture" or a "cord," regardless of whether both portions are part of a unitary suture or cord. Furthermore, references herein to a portion of a single length of suture can be referred to as a "suture portion," or simply a "suture."

Processes for repairing a target organ tissue, such as repair of mitral valve leaflets to address mitral valve regurgitation, can include inserting a tissue anchor delivery device, such as a delivery device as described in PCT Application No. PCT/US2012/043761, (published as WO 2013/003228, and referred to herein as "the '761 PCT Application") and/or in PCT Application No. PCT/US2016/055170 (published as WO 2017/059426 and referred to herein as "the '170 PCT Application"), the entire disclosures of which are incorporated herein by reference, into a body and extending a distal end of the delivery device to a proximal side of the target tissue (e.g., leaflet).

The '761 PCT Application and the '170 PCT Application describe in detail methods and devices for performing non-invasive procedures to repair a cardiac valve, such as a mitral valve. Such procedures include procedures to repair regurgitation that occurs when the leaflets of the mitral valve do not coapt properly at peak contraction pressures, resulting in an undesired backflow of blood from the ventricle into the atrium. As described in the '761 PCT Application and the'170 PCT Application, after the malfunctioning cardiac valve has been assessed and the source of the malfunction verified, a corrective procedure can be performed. Various procedures can be performed in accordance with the methods described therein to effectuate a cardiac valve repair, which may depend on the specific abnormality and the tissues involved.

FIG. 2 is a perspective view of a tissue anchor delivery system 100 in accordance with one or more examples. The tissue anchor delivery system 100 may be used to repair a heart valve, such as a mitral valve, and improve functionality thereof. For example, the tissue anchor delivery system 100 may be used to reduce the degree of mitral regurgitation in patients suffering from mitral regurgitation caused by, for example, midsegment prolapse of valve leaflets as a result of degenerative mitral valve disease. In order to repair such a valve, the tissue anchor delivery system 100 may be utilized to deliver and anchor tissue anchors, such as suture-knot-type tissue anchors, in a prolapsed valve leaflet. As described in detail below, such procedure may be implemented on a beating heart.

The delivery system 100 includes a rigid elongate tube 110 forming at least one internal working lumen. Although described in certain examples and/or contexts as comprising a rigid elongate tube, it should be understood that tubes, shafts, lumens, conduits, and the like disclosed herein may be either rigid, at least partially rigid, at least flexible, and/or at least partially flexible. Therefore, any such component described herein, whether or not referred to as rigid herein should be interpreted as possibly being at least partially flexible. In accordance with the present disclosure, the rigid elongate tube 110 may be referred to as a shaft for simplicity. Implementation of a valve-repair procedure utilizing the delivery system 100 can be performed in conjunction with certain imaging technology designed to provide visibility of the shaft 110 of the delivery system 100 according to a certain imaging modality, such as echo imaging. Generally, when performing a valve-repair procedure utilizing the tissue anchor delivery system 100, the operating physician may advantageously work in concert with an imaging technician, who may coordinate with the physician to facilitate successful execution of the valve-repair procedure.

In addition to the delivery shaft 110, the delivery system 100 may include a plunger feature 140, which may be used or actuated to manually deploy a pre-formed knot, such as a bulky knot as described in detail below. The tissue anchor delivery system 100 may further include a plunger lock mechanism 141, which may serve as a safety lock that locks the valve delivery system until ready for use or deployment of a leaflet anchor as described herein. The plunger 140 may have associated therewith a suture-release mechanism, which may be configured to lock in relative position a pair of suture tails 195 associated with a pre-formed knot anchor (not shown) to be deployed. For example, the suture portions 195 may be ePTFE sutures. The system 100 may further comprise a flush port 150, which may be used to de-air the lumen of the shaft 110. For example, heparinized saline flush, or the like, may be connected to the flush port 150 using a female Luer fitting to de-air the valve repair system 100. The term "lumen" is used herein according to its broad and ordinary meaning, and may refer to a physical structure forming a cavity, void, pathway, or other channel, such as an at least partially rigid elongate tubular structure, or may refer to a cavity, void, pathway, or other channel, itself, that occupies a space within an elongate structure (e.g., a tubular structure). Therefore, with respect to an elongate tubular structure, such as a shaft, tube, or the like, the term "lumen" may refer to the elongate tubular structure and/or to the channel or space within the elongate tubular structure.

The lumen of the shaft 110 may house a needle (not shown) that is wrapped at least in part with a pre-formed knot sutureform anchor, as described in detail herein. In some instances, the shaft 110 presents a relatively low profile. For example, the shaft 110 may have a diameter of approximately 3 mm or less (e.g., 9 Fr). The shaft 110 is associated with an atraumatic tip 114 feature. The atraumatic tip 114 can be an echogenic leaflet-positioner component, which may be used for deployment and/or positioning of the suture-type tissue anchor. The atraumatic tip 114, disposed at the distal end of the shaft 110, may be configured to have deployed therefrom a wrapped pre-formed suture knot (e.g., sutureform), as described herein.

The atraumatic tip 114 may be referred to as an "end effector." In addition to a pre-formed knot sutureform and associated needle, the shaft 110 may house an elongated knot pusher tube (not shown; also referred to herein as a "pusher"), which may be actuated using the plunger 140 in some instances. As described in further detail below, the tip 114 provides a surface against which the target valve leaflet may be held in connection with deployment of a leaflet anchor.

The delivery device 100 may be used to deliver a "bulky knot" type tissue anchor, as described in greater detail below. For example, the delivery device 100 may be utilized to deliver a tissue anchor (e.g., bulky knot) on a distal side of a mitral valve leaflet. The tip 114 (e.g., end effector), can be placed in contact with the ventricular side of a leaflet of a mitral valve. The tip 114 can be coupled to the distal end portion of the shaft 110, wherein the proximal end portion of the shaft 110 may be coupled to a handle portion 120 of the delivery device 100, as shown. Generally, the elongate pusher (not shown) may be movably disposed within a lumen of the shaft 110 and coupled to a pusher hub (not shown) that is movably disposed within the handle 120 and releasably coupled to the plunger 140. A needle (not shown) carrying a pre-formed tissue anchor sutureform can be movably disposed within a lumen of the pusher and coupled to a needle hub (not shown) that is also coupled to the plunger 140. The plunger 140 can be used to actuate or move the needle and the pusher during deployment of a distal anchor (see, e.g., FIGS. 8 and 9) and is movably disposed at least partially within the handle 120. For example, the handle 120 may define a lumen in which the plunger 140 can be moved. During operation, the pusher may also move within the lumen of the handle 120. The plunger lock 141 can be used to prevent the plunger 140 from moving within the handle 120 during storage and prior to performing a procedure to deploy a tissue anchor.

The needle may have the pre-formed knot disposed about a distal portion thereof while maintained in the shaft 110. For example, the pre-formed knot may be formed of one or more sutures configured in a coiled sutureform (see FIG. 7) having a plurality of winds/turns around the needle over a portion of the needle that is associated with a longitudinal slot in the needle that runs from the distal end thereof. Although the term "sutureform" is used herein, it should be understood that such components/forms may comprise suture, wire, or any other elongate material wrapped or formed in a desired configuration. The coiled sutureform can be provided or shipped disposed around the needle. In some instances, two suture tails extend from the coiled sutureform. The suture tails 195 may extend through the lumen of the needle and/or through a passageway of the plunger 140 and may exit the plunger 140 at a proximal end portion thereof. The coiled sutureform may advantageously be configured to be formed into a suture-type tissue anchor (referred to herein as a "bulky knot") in connection with an anchor-deployment procedure, as described in more detail below. The coiled sutureform can be configurable to a knot/deployed configuration by approximating opposite ends of the coiled portion thereof towards each other to form one or more loops.

The delivery device can further include a suture/tether catch mechanism (not shown) coupled to the plunger 140 at a proximal end of the delivery device 100, which may be configured to releasably hold or secure a suture 195 extending through the delivery device 100 during delivery of a tissue anchor as described herein. The suture catch can be used to hold the suture 195 with a friction fit or with a clamping force and can have a lock that can be released after the tissue anchor has been deployed/formed into a bulky knot, as described herein.

As described herein, the anchor delivery device 100 can be used in beating heart mitral valve repair procedures. In some instances, the shaft 110 of the delivery device 100 can be configured to extend and contract with the beating of the heart. During systolic contraction, the median axis of the heart generally shortens. For example, the distance from the apex 19 of the heart to the valve leaflets 52, 54 can vary by about 1 centimeter (cm) to about 2 centimeters (cm) with each heartbeat in some patients. In some instances, the length of the shaft 110 that protrudes from the handle 120 can change with the length of the median axis of the heart. That is, distal end of the shaft 110 can be configured to be floating such that the shaft can extend and retract with the beat of the heart so as to maintain contact with the target mitral valve leaflet.

Advancement of the delivery device 100 may be performed in conjunction with echo imaging, direct visualization (e.g., direct transblood visualization), and/or any other suitable remote visualization technique/modality. With respect to cardiac procedures, for example, the delivery device 100 may be advanced in conjunction with transesophageal (TEE) guidance and/or intracardiac echocardiography (ICE) guidance to facilitate and to direct the movement and proper positioning of the device for contacting the appropriate target cardiac region and/or target cardiac tissue (e.g., a valve leaflet, a valve annulus, or any other suitable cardiac tissue). Typical procedures that can be implemented using echo guidance are set forth in Suematsu, Y., J. Thorac. Cardiovasc. Surg. 2005; 130:1348-56 ("Suematsu"), the entire disclosure of which is incorporated herein by reference.

Figure 3:
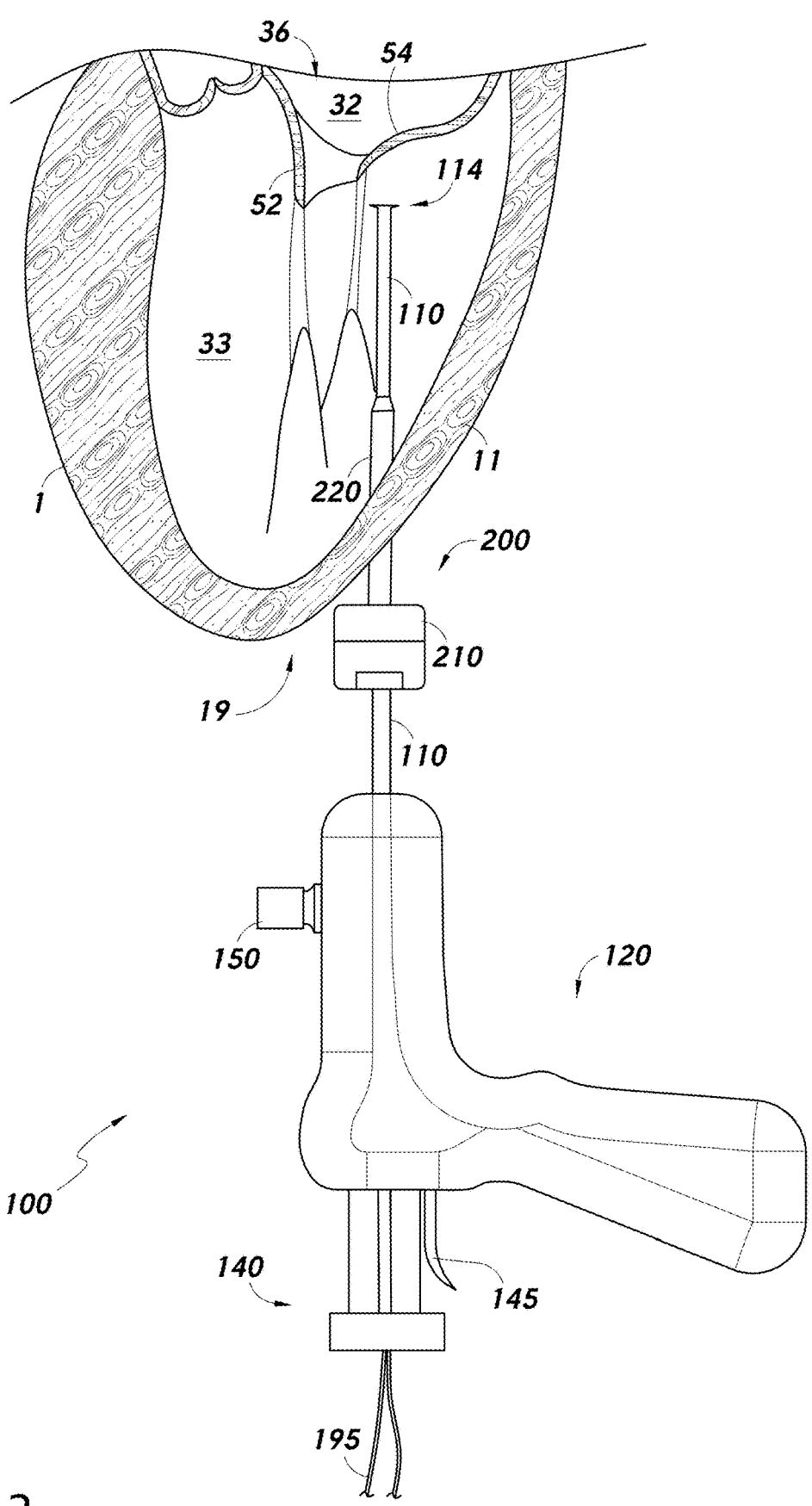
FIG. 3 is a cutaway view of a tissue anchor delivery device disposed at least partially within a chamber of a heart in accordance with one or more examples.

FIG. 3 is a cutaway view of a tissue anchor delivery device 100 disposed at least partially within a chamber of a heart in accordance with one or more examples. According to some implementations of valve-repair procedures, an incision into the apical region 39 of the appropriate ventricle 33 of the heart is made. For instance, an introducer port device 200 containing a one or more fluid-retention valves to prevent blood loss and/or air entry into the ventricle 33, may be inserted into the site of entry. Once inside the chamber, the shaft 110 of the delivery device 100 may be advanced through the lumen 220 of the introducer 200. In some instances, a sheath may be inserted through the introducer 200, through which one or more other instruments are advanced. For instance, an endoscope may first be advanced into the chamber to visualize the ventricle, the valve 36, and/or the sub-valvular apparatus. By use of an appropriate endoscope, a careful analysis of the malfunctioning valve 36 may be performed. Each segment of each leaflet may be carefully assessed to determine its pliability, integrity, and motion. Based on this assessment, the practitioner can determine whether the valve can indeed be repaired or must be replaced. The motion of the leaflets 52, 54 can be classified as slightly dysfunctional, prolapsed, or restricted and based on this classification, the necessary steps of the repair can be determined.

Mitral valve regurgitation generally increases the workload on the heart and may lead to very serious conditions if left untreated, such as decreased ventricular function, pulmonary hypertension, congestive heart failure, permanent heart damage, cardiac arrest, and ultimately death. Since the left heart is primarily responsible for circulating the flow of blood throughout the body, malfunction of the mitral valve 36 is particularly problematic and often life threatening. Methods and devices are provided herein, as well as in the '761 PCT Application and the '170 PCT Application, for performing non-invasive procedures to repair a cardiac valve, such as a mitral valve. Such procedures include procedures to repair regurgitation that occurs when the leaflets of the mitral valve do not coapt properly at peak contraction pressures, resulting in an undesired backflow of blood from the ventricle into the atrium. As described in the '761 PCT Application and the '170 PCT Application, after the malfunctioning cardiac valve has been assessed and the source of the malfunction verified, a corrective procedure can be performed. Various procedures can be performed in accordance with the methods described therein to effectuate a cardiac valve repair, which will depend on the specific abnormality and the tissues involved.

After a minimally invasive approach is determined to be advisable, one or more incisions may be made proximate to the thoracic cavity to provide a surgical field of access. The total number and length of the incisions to be made depend on the number and types of the instruments to be used as well as the procedure(s) to be performed. The incision(s) may advantageously be made in such a manner as to be minimally invasive. As referred to herein, the term "minimally invasive" means in a manner by which an interior organ or tissue may be accessed with relatively little damage being done to the anatomical structure through which entry is sought. For example, a minimally invasive procedure may involve accessing a body cavity by a small incision of, for example, approximately 5 cm or less made in the skin of the body. The incision may be vertical, horizontal, or slightly curved. If the incision is located along one or more ribs, it may advantageously follow the outline of the rib. The opening may advantageously extend deep enough to allow access to the thoracic cavity between the ribs or under the sternum and is preferably set close to the rib cage and/or diaphragm, dependent on the entry point chosen.

In one example method, the heart may be accessed through one or more openings made by one or more small incision in a portion of the body proximal to the thoracic cavity, such as between one or more of the ribs of the rib cage of a patient, proximate to the xyphoid appendage, or via the abdomen and diaphragm. Access to the thoracic cavity may be sought to allow the insertion and use of one or more thorascopic instruments, while access to the abdomen may be sought to allow the insertion and use of one or more laparoscopic instruments. Insertion of one or more visualizing instruments may then be followed by transdiaphragmatic access to the heart. Additionally, access to the heart may be gained by direct puncture (e.g., via an appropriately sized needle, for instance an 18-gauge needle) of the heart from the xyphoid region. Accordingly, the one or more incisions should be made in such a manner as to provide an appropriate surgical field and access site to the heart in the least invasive manner possible. Access may also be achieved using percutaneous methods, further reducing the invasiveness of the procedure. See, e.g., "Full-Spectrum Cardiac Surgery Through a Minimal Incision Mini-Sternotomy (Lower Half) Technique," Doty et al., *Annals of Thoracic Surgery* 1998; 65 (2): 573-7 and "Transxiphoid Approach Without Median Sternotomy for the Repair of Atrial Septal Defects," Barbero-Marcial et al., *Annals of Thoracic Surgery* 1998; 65 (3): 771-4, the entire disclosures of each of which are incorporated herein by reference.

Generally, the shaft 110 of the tissue anchor delivery device 100 may be slowly advanced into the introducer 200 until the tip 114 has flushed the introducer 200 and entered the ventricle 33. In so doing, it may be desirable to advance the shaft 110 within the ventricle 33 in such a way as to avoid traversing areas populated by papillary muscles and/or associated chordae tendineae to avoid entanglement therewith. In order to facilitate or ensure avoidance of such anatomy, imaging technology may advantageously be implemented to provide at least partial visibility of the shaft 110 within the ventricle 33, as well as certain anatomical features within the ventricle. In some implementations, hybrid imaging technologies may be used, wherein echo imaging is used in combination with a different imaging modality. Multi-imaging modalities may provide improved visibility of anatomical and/or delivery system components.

Although the procedures described herein are with reference to repairing a cardiac mitral valve or tricuspid valve by the implantation of one or more leaflet anchors and associated suture(s)/cord(s), the methods presented are readily adaptable for various types of tissue, leaflet, and annular repair procedures. The methods described herein, for example, can be performed to selectively approximate two or more portions of tissue to limit a gap between the portions. That is, in general, the methods herein are described with reference to a mitral valve but should not be understood to be limited to procedures involving a mitral valve. Furthermore, aspects of the present disclosure applicable to non-biological structures and devices. For example, other cord or suture tensioning applications not involving biological tissue may incorporate aspects of the pension balancing and/or distribution devices, systems, and processes disclosed herein.

Figure 4:
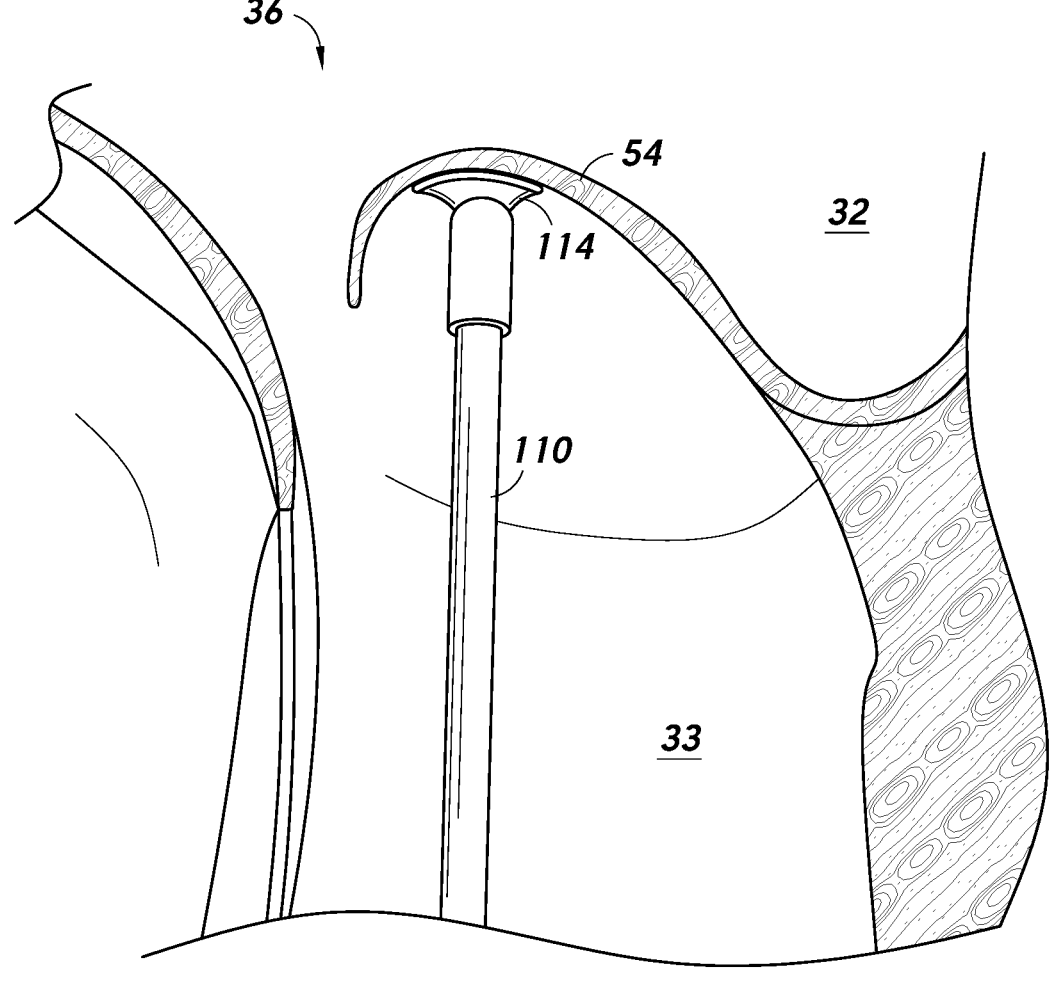
FIG. 4 is a close-up view of a distal portion of a tissue anchor delivery device shaft assembly positioned against a target heart valve leaflet in accordance with one or more examples.

FIG. 4 shows a close-up view of a shaft 110 of a tissue anchor delivery device 100 inserted into a ventricle 33 (e.g., left ventricle) and approximated to a target valve leaflet 54 in connection with a valve-repair procedure in accordance with one or more examples of the present disclosure. For example, the valve 36 may be a mitral valve. The anchor delivery device shaft 110 can be configured to deliver a tissue anchor (not shown; see, e.g., FIGS. 5-7), such as a bulky knot, to the valve leaflet 54. As an example, FIG. 4 shows a valve leaflet 54, which may represent a posterolateral leaflet of a mitral valve. It will be understood that the anchor delivery device shaft 110 can also deliver a tissue anchor to the anteromedial mitral valve leaflet. Although the description of FIGS. 4-7 below is presented in the context of a mitral valve, it should be understood that the principles disclosed herein are applicable to other valves or biological tissues, such as a tricuspid valve.

With reference to FIGS. 4-7, the anchor delivery device shaft 110 can comprise one or more elongate lumens configured to allow delivery of the anchor 190 to the valve leaflet 54. The shaft 110 can be configured to facilitate performance of one or more functions, such as grasping, suctioning, irrigating, cutting, suturing, or otherwise engaging a valve leaflet. The distal end, or tip, 114 of the shaft 110 can be configured to contact the mitral valve leaflet 54 without substantially damaging the leaflet to facilitate repair of the valve 36. For example, during a valve-repair procedure, a handle (e.g., handle 120) coupled to the shaft 110 can be manipulated in such a manner so that the leaflet 54 is contacted with the functional distal portion of the shaft 110 and a repair effectuated.

Echo imaging guidance, such as transesophageal echocardiogram (TEE) (2D and/or 3D), transthoracic echocardiogram (TTE), and/or intracardiac echo (ICE), may be used to assist in the advancement and desired positioning of the anchor delivery device shaft 110 within the ventricle 33. The distal end 114 of the shaft 110 can contact a proximal surface (e.g., underside surface with respect to the illustrated orientation of FIGS. 4-7) of the mitral valve leaflet 54, without or substantially without damaging the leaflet 54. For example, the end/tip portion or component 114 can have a relatively blunt form or configuration. The end/tip portion or component 114 can be configured to maintain contact with the proximal side of the valve leaflet 54 as the heart beats to facilitate reliable delivery of the anchor 191/190 to the target site on the leaflet 54.

Figure 5:
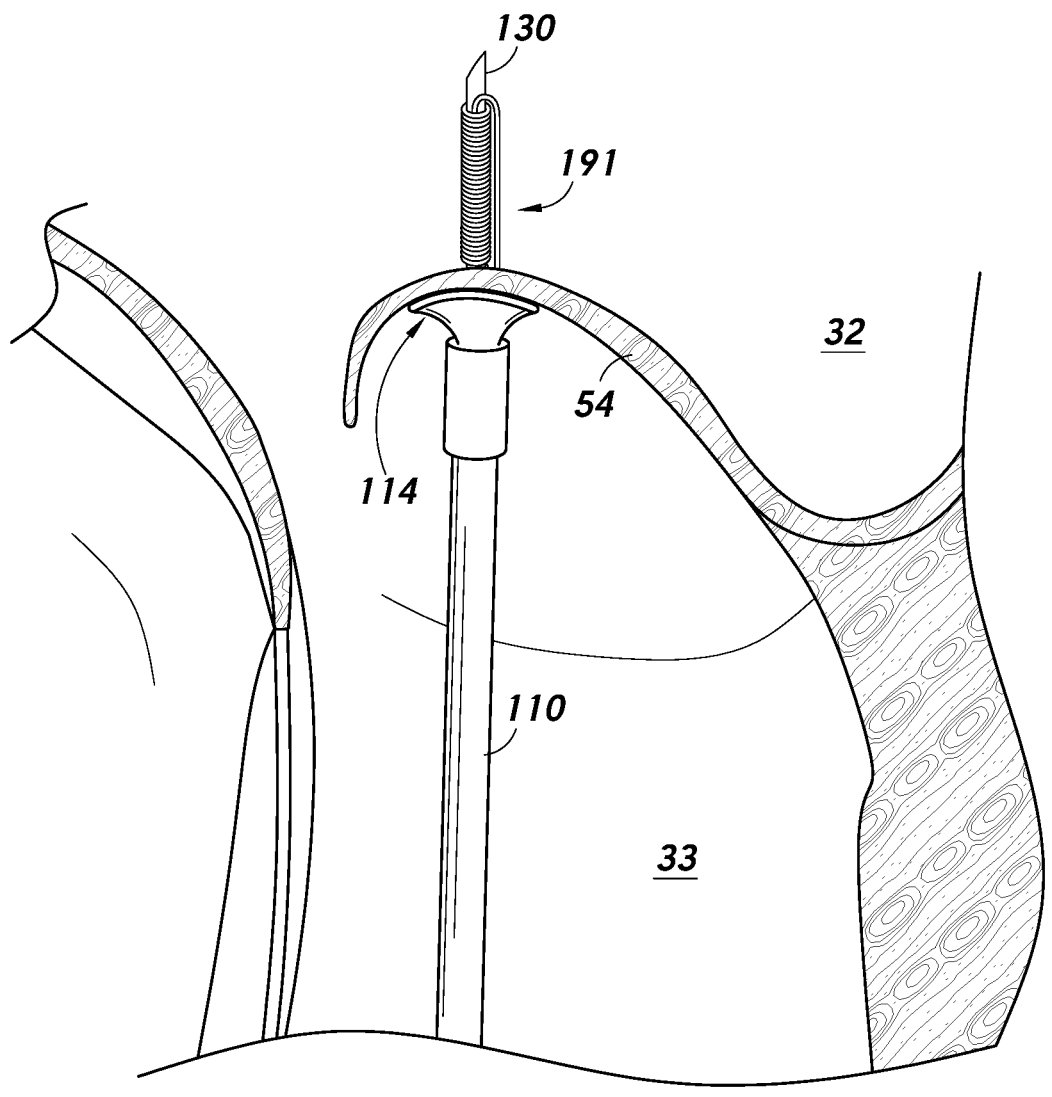
FIG. 5 is a close-up view of a distal portion of a tissue anchor delivery device shaft having a needle and tissue

In some instances, one or more perforation devices 130 (e.g., needle(s)) can be delivered through a working lumen (not shown) of the shaft 110 to the valve leaflet 54 to puncture the valve leaflet 54 and project a sutureform 191 including a plurality of winds of suture about a distal portion of a needle 130 into the atrium 32 (see FIG. 5), wherein the sutureform is deployed to form the bulky knot tissue anchor 190 shown in FIGS. 6 and 7. For example, as shown in FIG. 5, a slotted needle 130 can be deployed from the distal end of the shaft 110, thereby puncturing the leaflet 54 and projecting into the atrium 32, wherein the slotted needle 130 is wrapped with a sutureform 191 (e.g., PTFE suture) in a particular configuration (see the '761 PCT Application for further detail regarding example suture wrapping configurations and needles for use in suture anchor deployment devices and methods). In some instances, a pusher or hollow guide wire (not shown) is provided on or at least partially around the needle 130 within the shaft 110, such that the needle may be withdrawn, leaving the pusher and wound sutureform 191. When a withdrawal force is applied to the sutureform 191 using the pusher, the sutureform 191 may form a bulky-knot-type anchor (e.g., the anchor 190), after which the pusher may be withdrawn, leaving the permanent knot 190 to anchor the suture(s) 195 to the leaflet 54.

FIG. 4 shows the shaft 110 of the tissue anchor delivery device 100 positioned on the target valve leaflet 54 (e.g., mitral valve leaflet). For example, the target site of the valve 54 may be slowly approached from the ventricle side thereof by advancing the distal end of the shaft 110 along or near to the posterior wall of the ventricle 33 (e.g., left ventricle) without contacting the ventricle wall. Successful targeting and contacting of the target location on the leaflet 54 can depend at least in part on accurate visualization of the shaft 110 and/or tip/end effector 114 throughout the process of advancing the tip 114 to the target site. Generally, echocardiographic equipment may be used to provide the necessary or desired intra-operative visualization of the shaft 110 and/or tip 114.

Once the tip 114 is positioned in the desired position, the distal end of the shaft 110 and the tip 114 may be used to drape, or "tent," the leaflet 54 to better secure the tip 114 in the desired position, as shown in FIG. 4. Draping/tenting may advantageously facilitate contact of the tip 114 with the leaflet 54 throughout one or more cardiac cycles, to thereby provide more secure or proper deployment of leaflet anchor(s). The target location may advantageously be located relatively close to the free edge of the target leaflet 54 to minimize the likelihood of undesirable intra-atrial wall deployment of the anchor. Navigation of the tip 114 to the desired location on the underside of the target valve leaflet 54 may be assisted using echo imaging, which may be relied upon to confirm correct positioning of the tip 114 prior to anchor/knot deployment.

With the shaft 110 positioned against the target leaflet 54, the plunger 140 of the tissue anchor delivery device 100 can be actuated to move the needle 130 and a pusher disposed within the shaft 110, such that the coiled sutureform portion 191 of the suture anchor slides off the needle 130. As the plunger 140 is actuated, a distal piercing portion of the needle 130 punctures the leaflet 54 and forms an opening in the leaflet. FIG. 5 shows a close-up view of the distal portion of the delivery device shaft 110 showing the needle 130 and tissue anchor sutureform 191 projected therefrom through the target leaflet 54 in accordance with one or more examples. In some instances, the needle 130 is projected a distance of between about 5-8 mm, or less, distally beyond the distal end of the shaft 130 (e.g., beyond the tip 114). In some instances, the needle 130 is projected a distance of between about 3-11 mm. In some instances, the needle 130 is projected a distance of about 2.5 cm, or greater. In some instances, the needle 130 extends until the distal tip of the needle and the entire coiled sutureform 191 extend through the leaflet 54. While the needle 130 and sutureform 191 are projected into the atrial side 32 of the leaflet 54, the shaft 110 and tip 114 advantageously remain entirely on the ventricular side 33 of the leaflet 54.

As the pusher (not shown) within the tissue anchor delivery device shaft 110 is moved distally, a distal end of the pusher advantageously moves or pushes the distal coiled sutureform 191 (e.g., pre-deployment coiled portion of the suture anchor) over the distal end of the needle 130 and further within the atrium 32 of the heart on a distal side of the leaflet 54, such that the sutureform extends distally beyond a distal end of the needle 130. For example, in some instances, at least half a length of the sutureform 191 extends beyond the distal end of the needle 130. In some instances, at least three quarters of the length of the sutureform 191 extends beyond the distal end of the needle 130. In some instances, the entire coiled sutureform 191 extends beyond the distal end of the needle 130.

After the sutureform 191 has been pushed off the needle 130, pulling one or more of the suture tail(s) 195 (e.g., suture strands extending from the coiled portion of the suture) associated with the tissue anchor 190 proximally can cause the sutureform 191 to form a bulky knot anchor 190, as shown in FIG. 6, which provides a close-up view of the formed suture anchor 190 on the atrial side 32 of the leaflet 54. For example, the bulky knot suture anchor 190 may be formed by approximating opposite ends of the coils of the sutureform 191 (see FIG. 6) towards each other to form one or more loops. After the sutureform 191 has been formed into the bulky knot 190, the delivery device 100 can be withdrawn proximally, leaving the tissue anchor 190 disposed on the distal atrial side of the leaflet 54, as shown in FIG. 7. In some instances, two suture tails 195 may extend from the proximal/ventricle side 33 of the leaflet 54 and out of the heart 1. For example, the delivery device shaft 110 can be slid/withdrawn over the suture tail(s) 195. The suture tails can be advantageously be tensioned in a balanced manner according to aspects of the present disclosure.

FIG. 7 shows a cutaway view of the deployed leaflet anchor 190 in accordance with one or more examples of the present disclosure. The suture tails 195*a*, 195*b* coupled to the anchor 190 may be secured at the desired tension using a pledget 71 or other suture-fixing/locking device or mechanism on the outside of the heart through which the suture tails 195 may pass. For example, a suture tension distribution and/or balancing device in accordance with examples of the present disclosure may be utilized in addition to, or instead of, the pledget 71 for securing and/or tensioning the suture tails 195. Furthermore, one or more knots 75 (e.g., a knot stack) or other suture fixation mechanism(s) or device (s) may be implemented to hold the sutures at the desired tension and to the pledget/device 71. With the suture tail(s) 195 fixed to the ventricle wall 11, a ventricular portion of the suture tail(s) 195 may advantageously function as replacement leaflet cords (e.g., chordae tendineae) that are configured to tether the target leaflet 54 in a desired manner and at a desired tension.

FIG. 8 shows a top view of a heart valve 860 with leaflets 803, 804 having a plurality of tissue anchors 892, 893 implanted therein in accordance with one or more examples. For example, the heart valve 860 may be a mitral valve, tricuspid valve, or other type of valve or tissue. That is, although certain description is presented below describing a mitral valve, it should be understood that such description is for simplicity and clarity only, and the principles disclosed herein are applicable to other types of tissue or anatomy.

With respect to mitral valve repair procedures, the heart valve 860 may be considered to include an anterior leaflet 804 and a posterior leaflet 803. The leaflets 803, 804 may be joined at anterior 895 and posterior 897 commissure regions, respectively. In some implementations, one or more tissue anchors 892, 893 may be deployed in one or both of the leaflets 803, 804. For example, one or more tissue anchors 892*a-c* may be implanted in one or more of the A1, A2, and/or A3 regions (not labeled in FIG. 8 for clarity; generally numbered from lateral to medial) of the anterior leaflet 804. Additionally or alternatively, one or more tissue anchors 893*a-c* may be implanted in one or more of the P1, P2, and/or P3 regions (not labeled in FIG. 8 for clarity; generally numbered from lateral to medial) of the posterior leaflet 803. The deployed leaflet anchors may generally be below the surface of coaptation. With respect to posterior mitral valve leaflet repair, the anterior leaflet may advantageously touch the posterior leaflet basal to the leaflet anchor (s).

Each of the various tissue anchors shown in FIG. 8 may be associated with one or more suture tails, which may be referred to a suture portions in certain contexts herein. For example, in some implementations, the tissue anchors 892, 893 comprise suture forms in the form of a knot, or the like. For example, single unitary sutures may be respectively formed into the illustrated tissue anchor knots, wherein tail portions associated with the sutures/knots run from the knots to another anchor point, such as an anchor point on an outside ventricle wall or surface as shown in FIG. 7. Although certain examples are described herein in connection with pairs of suture tails associated with a respective tissue anchor, in some instances a single suture tail/portion may be associated with a single tissue anchor. Furthermore, it should be understood that suture tensioning devices and methods disclosed herein, regardless of whether such description references single suture portions or pairs of suture portions or any other number of suture portions/tails, are applicable to tension balancing and/or distribution of any number of suture portions, including single suture tails and pairs of suture tails associated with a single tissue anchor.

Suture Tensioning

Examples of the present disclosure provide solutions for achieving matched/balanced and/or desired tension levels across a plurality of suture tails and/or pairs of suture tails. FIG. 9 shows a plurality of suture pairs 995 passing through a cardiac tissue wall 911 and through a tourniquet 930 in accordance with one or more examples. In some implementations, one or more leaflet anchors is deployed in each of the mitral valve leaflets, wherein sutures/cords coupled to separate leaflets are secured together in the heart by tying them together with knots or by another suitable attachment device, creating an edge-to-edge repair to decrease the septal-lateral distance of the mitral valve orifice.

According to some processes, tensioning of the suture portions 995 is performed after the placement of the associated tissue anchors in respective target tissue. With the sutures 995 pulled/passed through the ventricle wall 911, the ends of the sutures may be pulled manually to remove slack in the sutures 995. Generally, tensioning of the sutures 95 may not be performed prior to such slack-removal. Once some or all of the slack is taken out of the individual sutures and/or suture pairs, the sutures 995 can be pulled simultaneously to further increase the tension thereon (or let tension out). The sutures 995 can be pulled together through the tourniquet 930. For example, the sutures 995 can be pulled from proximal end portions thereof to achieve the determined/desired tension.

In some implementations, suture tensioning and/or fixing can be performed using the pledget 960 or other type of device through which the suture portions 995 may be passed and/or to which the suture portions can be secured, such as by tying one or more knots, or the like (see FIG. 10). For example, as shown in FIG. 9, the suture pairs 995a, 995b, 995c, each of which may be associated with a separate tissue anchor (e.g., heart valve leaflet tissue anchor), can pass through the tissue wall 911, which may be, for example, a ventricle wall associated a ventricle 33 or other area/chamber of a patient. The suture portions 995 may further be passed through a pledget device 960, which may serve at least in part to provide a buffer between the proximal suture portions/knots and the tissue wall 911.

Knots can be tied on the long free ends of the sutures 995 outside of the heart prior to placement of the pledget 960. The suture portions 995 can be identified as pairs (995a, 995b, 995c) by their respective associated knots. In some implementations, the pairs of sutures can be separated out into the two strands of the pair and put through a pledget 960. A French-eye needle may be used to pull the sutures through the pledget 960. The pairs of sutures can be identified on the proximal side of the pledget 960 based on the locations through which they exit the pledget 960. The tourniquet 930 may interface against the ventricle wall 911, with the pledget 960 positioned between the tourniquet 930 and the tissue wall 911.

The pledget 960 can be, for example, a low-porosity and relatively stiff pledget. Such a pledget may advantageously allow for the desired tension of the suture tails 995 to be sustained over an extended postoperative period of time. In some instances, suture tying or fixation may be implemented using one or more soft tissue retractors and/or right-angle clamps (not shown), which be rubber shod to reduce the risk of damage to the suture portions 995.

In certain implementations, testing of location and/or tension of the tissue anchors and/or associated suture tail(s) 995 may be performed by gently tensioning the suture tails until leaflet motion is felt and/or observed. Echo imaging technology may be used to view and verify the anchor placement and resulting leaflet function. The steps and processes outlined above for placing a suture-knot-type tissue anchors may be repeated as necessary until the desired number of anchors have been implanted on the target valve leaflet.

In some implementations, tension adjustment in the pairs of suture tails 995 associated with multiple tissue (e.g., leaflet) anchors may be performed simultaneously. The appropriate number of leaflet anchors may advantageously be determined to produce the desired coaptation of the target valve leaflets. The pledget 960 may be drawn against the surface (e.g., epicardial surface) of the tissue wall 911, and all the suture tails 995 may be inserted through a common tourniquet 930 or like structure so that all suture portions/tails can be tensioned together.

FIG. 10 shows a plurality of suture pairs 109 (identified individually as suture pairs 109a-c) passing through a cardiac tissue wall 111 and knotted on a pledget 106 in accordance with one or more examples. As shown, in some implementations, suture tails may be knotted together on a proximal side of the tissue wall 111. For example, two suture tails emanating from a common tissue anchor may be knotted together against the pledget 106. Knotting together of suture portions in accordance with aspects of the present disclosure may involve forming one or more knot stacks 107a-c, wherein multiple knots are tied in succession using a single pair of suture tails, or pairs of pairs the suture tails, in order to provide improved fixation and/or reduce the likelihood of the not becoming undone postoperatively.

In some implementations, the present disclosure relates to devices and methods used to balance the load distribution on sutures. In accordance with some solutions, sutures can be hand-gripped, wherein the movements of the mitral leaflets are allowed to tug on the sutures to balance the load. However, such tensioning solutions may not sufficiently account for postoperative tension changes over time. For example, after a suturing procedure, the patient's heart and leaflet conditions may change at least in part, thereby causing previously evenly-loaded sutures to become unevenly loaded. This may cause tension overload on one of the sutures or suture pairs. In some implementations, the present disclosure provides solutions for distributing and/or balancing of suture tension loads postoperatively and automatically through the beating motion of the leaflet(s), thereby achieving relatively long-term effectiveness with respect to the suturing procedure.

FIG. 11 shows a cutaway view of a heart including a plurality of leaflet anchors 112, 113 implanted in respective leaflets or leaflet portions therein in accordance with one or more examples of the present disclosure. As demonstrated by the image of FIG. 11, suture tails from a single tissue anchor (e.g., knot) can be secured to a tissue wall 11 and/or pledget 116 disposed thereon or in proximity thereto, wherein one of the suture tails (e.g., 118b, 119a) is tighter and/or has a greater amount of tension thereon compared to another of the suture tails (e.g., 118a, 119b) associated with the specific tissue anchor. For example, the tissue anchor 112 is shown deployed against a first valve leaflet or leaflet portion 52, wherein a first suture tail 118a emanating therefrom is looser and/or has more slack than another suture tail 118b associated with the tissue anchor 112, whereas the tissue anchor 113 is associated with a plurality of suture tails 119a, 119b, wherein the suture tail 119a is tighter than the suture tail 118b.

Differences in tension between suture tails associated with a single tissue anchor may be caused by various factors. For example, the anatomy in which the particular tissue anchor and/or associated suture tails is/are implanted may be such that distances between distal and proximal tissue-fixation points is different with respect to the different suture tails. Furthermore, execution of suture tensioning by the relevant technician may result in one suture tails being tensioned to a greater degree than another suture tail, whether due to operator execution/error or other contributing factors. With suture tails unevenly tensioned as in FIG. 11, uneven stress may be imposed on certain biological tissue and/or suture/anchor portions, resulting in uneven wear, damage, functionality, or the like. For example, where a disproportionate amount of tension is imposed on one suture tail, which is deployed through a particular area or portion of biological tissue, such tissue may become damaged and/or the suture associated therewith may disproportionately be drawn through such tissue and/or cause damage thereto, which may ultimately result in physiological damage and/or other performance failure with respect to the implant device. Therefore, it may be desirable to facilitate and/or ensure that tension levels associated with separate suture tails of a single tissue anchor device are balanced to some degree and/or are tensioned such that differences in tension between such suture portions is reduced or minimized.

FIG. 12 shows a cutaway view of a heart including a plurality of leaflet anchors 122, 123 implanted in respective leaflets or leaflet/tissue portions 52, 54 therein in accordance with one or more examples of the present disclosure. As demonstrated by the image of FIG. 12, suture tails/portions from a separate tissue anchors (e.g., knots) can be secured to a tissue wall 11 and/or pledget 126 disposed thereon or in proximity thereto, wherein the suture portions 128 associated with a first tissue anchor 122 are tighter and/or have a greater amount of tension thereon compared to suture portions 129 associated with a second tissue anchor 123. For example, the first tissue anchor 122 is shown deployed against a first valve leaflet or leaflet portion 52 and is associated with relatively tight suture portions/tails 128, whereas the second tissue anchor 123 is shown deployed against a second valve leaflet or leaflet portion 54 and is associated with relatively loose suture portions/tails 129.

Differences in tension between suture tails associated with a different tissue anchors may be caused by various factors. For example, the anatomy in which the particular tissue anchors and/or associated suture tails is/are implanted may be such that distances between distal and proximal tissue-fixation points is different with respect to the different tissue anchors. Furthermore, execution of suture tensioning by the relevant technician may result in suture tails/portions (e.g., suture pair) associated with one tissue anchor being tensioned to a greater degree than suture tails/portions associated with another tissue anchor, whether due to operator error or other contributing factors. With suture pairs unevenly tensioned as in FIG. 12, uneven stress may be imposed on certain biological tissue and/or suture/anchor portions, resulting in uneven wear, damage, functionality, or the like. For example, where a disproportionate amount of tension is imposed on one leaflet portion, valve regurgitation or other functional defects may result. Furthermore, the tissue to which such anchor/suture(s) is/are anchored may become damaged and/or the suture(s) associated therewith may disproportionately be drawn through such tissue and/or cause damage therein, which may ultimately result in physiological damage and/or other performance failure with respect to the implant device. Therefore, it may be desirable to facilitate and/or ensure that tension levels associated with suture tails/portions of different tissue anchor devices are balanced to some degree and/or are tensioned such that differences in tension between such suture portions is reduced or minimized.

Tension Distribution Devices

In some implementations, the present disclosure relates to suture tension-balancing/distributing devices configured to facilitate the balancing/distribution of tension across a plurality of sutures or suture portions associated with one or more tissue anchors implanted on, for example, a mitral valve leaflet to help achieve proper coaptation and reduce regurgitation. Such tension re-distribution can help prevent any one suture or grouping of sutures from inheriting a majority of the tension load, which can cause the suture(s) to be over-tensioned and/or cause premature suture rupturing, triggering re-operation in some cases.

FIG. 13 shows a cutaway side view of a tension-distribution device 136 having sutures 138, 139 engaged therewith in accordance with one or more examples of the present disclosure. FIG. 13 shows a plurality of suture pairs 138, 139, each comprising one or more suture portions, as shown. For example, such suture portions may be associated with respective tissue anchors, such as heart valve leaflet anchors, as described in detail herein. In some implementations, the suture tails 138, 139 may traverse the tissue wall 131 and may be anchored on a proximal side 55 of the tissue wall 131 to thereby secure the respective suture pairs and/or suture portions in a tensioned configuration between the tension-distribution device 136 on a proximal end and a distal target tissue fixation location on a distal end (not shown).

In some instances, the tension-distribution device 136 includes certain suture-engagement features configured to allow for suture portions and/or pairs of suture portions to be engaged therewith in a manner to allow for longitudinal sliding of the suture portion(s) through the suture-engagement features. In some instances, the suture-engagement features 135 comprise apertures through which suture portions and/or suture portion pairs may be threaded or passed in some manner. However, it should be understood that suture-engagement features described and/or implemented in connection with any of the tension-distribution device examples disclosed herein and/or associated processes may include one or more apertures, holes, hooks, slits, channels, paths, eyelets, wedges, or other feature(s) configured to allow for engagement of a suture portion or plurality of suture portions therewith to thereby at least partially secure or contain the suture portions and/or restrict the lateral, radial, and/or circumferential movement thereof with respect to one or more portions of the tension-distribution device in some manner or to some degree.

In an implanted/deployed configuration, the suture portions 138, 139 may be engaged with respective suture-engagement features 135 in any suitable or desirable manner. For example, in some implementations, the suture-engagement features 135 may be circumferentially distributed with respect to any suitable or desirable radius of the tension-distribution device with respect to a center point thereof. For example, tension-distribution devices in accordance with examples of the present disclosure may have a generally circular, rectangular, triangular, pentagonal, hexagonal, or other axial cross-sectional shape with respect to a central axis 501 thereof. The suture-engagement features of such devices may advantageously be evenly and/or opposingly distributed about the axis 501 such that equal weight application at such suture-engagement features results in a balanced disposition of the device. That is, the suture-engagement features can advantageously be positioned in a balanced configuration/disposition about the axial center point of the device. For example, each of the suture-engagement features may be positioned or disposed at the same radius from the center point (not shown; see FIG. 15). Furthermore, the suture-engagement features may advantageously be rotationally offset from one another with respect to the axial center point by the same amounts/angle.

In order to allow for balancing of the suture-engagement features 135 of the central axis 501, examples of tension-distribution devices in accordance with aspects of the present disclosure can advantageously have rotational/radial symmetry with respect to a central axis thereof. That is, one or more rotational cutting planes about the central axis produce similar or identical pieces; such similar/identical pieces are regularly arranged around the central axis. The rotational symmetry of tension-distribution and-balancing devices in accordance with the present disclosure can be of any suitable or desirable degree with respect to the number of distinct orientations in which the shape of the device is similar. Example shapes include circles, triangles, squares, pentagons, hexagons, heptagons, octagons, and so on.

In an implanted or deployed configuration, suture portions or pairs of suture portions may be passed through respective ones of the suture-engagement features 135. For example, as shown in the example implementation of FIG. 13, individual suture portions 138*a*, 138*b*, 139*a*, 139*b* may be individually engaged with respective ones of the suture-engagement features 135. Therefore, processes of balancing and/or distributing suture tension in accordance with examples of the present disclosure can involve passing or otherwise engaging suture portions and/or pairs or other groupings of suture portions through respective suture-engagement features of a tension-distribution device. Once the suture portions have been engaged with their respective suture-engagement features, processes of balancing and/or distributing suture tension among the respective suture portions and/or groupings of suture portions may involve tying or otherwise securing or fixing different suture portions or groupings of suture portions together on a proximal side of the tension-distribution device 136, as shown in FIG. 13. For example, in some patients, suture portions associated with opposite sides of the tension-distribution device 136 may be tied or otherwise secured/fixed together. Alternatively, adjacent suture portions or groupings of suture portions may be tied or otherwise secured/fixed together on the distal side of the tension-distribution device.

With respect to certain examples of tension-distribution devices described herein, the terms "distal side" (or "distal face") and "proximal side" (or "proximal face") are used for convenience. However, it should be understood that such designations may be considered arbitrary with respect to some implementations. For example, it should be understood that references to a distal side of a tension-distribution device may refer to any axial side of a tension-distribution device, wherein the proximal side thereof refers to the opposite axial side with respect to the referenced distal side of the tension-distribution device. For convenience, the proximal side PS of the tension-distribution device 136 is shown and described as being a side of the device 136 generally facing a physician/surgeon with respect to certain relevant valve repair operations, whereas the distal side DS may generally face the heart and/or heart valve being repaired. The distal side DS may be considered the tissue-contact side or face in some contexts. In connection with some instances of the present disclosure, the distal side of a tension-distribution device may be referred to as a "top side" (or "topside surface" or "topside face") and the proximal side may be referred to as a "bottom side" (or "bottom-side surface" or "bottom-side face"). However, such terms are used for convenience, and may or may not indicate any relational orientation of such devices. Although certain examples are disclosed herein as comprising disc-shaped tension-distribution devices, and/or other devices having an axial thickness and multiple generally-flat faces separated by such axial thickness, it should be understood that references to "sides," or "faces," of a tension-distribution device in accordance with the present disclosure may refer to any axial areas of a tension-distribution device on opposite sides of an axial plane 502 associated with the tension-distribution device 136. It should be clear that any description or terminology relating to features associated with the tension-distribution device 136 and/or other aspects of the diagram of FIG. 13 are applicable to any of the other examples illustrated and described in connection with the present disclosure.

The suture-engagement features 135 can advantageously allow for sutures to slide therethrough. For example, such features 135 may be designed to reduce the amount of sliding friction that the relevant sutures are subjected to thereby allow for relatively free movement of the sutures along lengths thereof when such sutures are engaged with respective suture-engagement features. Therefore, when separate suture portions and/or groupings of suture portions have been tied or otherwise fixed/secured to one another on the distal side DS of the tension-distribution device 136, the fixation point(s) 137*a*, 137*b* through which the suture portions are fixed to one another may be allowed/permitted to slide or otherwise migrate towards one or more of the suture-engagement features after tying/fixing the relevant suture portions and/or groupings of suture portions to one another. For example, as shown in FIG. 13, the knot stack coupling the suture portion 139*a* to the suture portion 138*b* can migrate over time to a position that is closer to one of the suture-engagement features through which one of the suture portions or groups of suture portions is passed or otherwise engaged than to another of the suture-engagement features 135 through which another of the suture portions or groupings of suture portions is passed or otherwise engaged. Such migration of the knots or other couplings or fixation mechanism(s)/device(s) may be caused at least in part by a tension differential between the respective suture portions. For example, tighter suture portions and/or groupings of suture portions may pull with greater force distally than looser suture portions and/or groupings of suture portions that are tied or otherwise fixed thereto, thereby pulling the coupling (e.g., knot or other fixation point) between the disparately-tensioned suture portions towards the suture-engagement feature through which the tighter suture portion(s) and/or grouping(s) of suture portions are passed or otherwise engaged.

Migration (e.g., postoperative migration) of the suture portions and/or knot(s)/coupling(s) may serve to balance/distribute the tension between the knotted/coupled suture portions and/or groupings of suture portions. The terms "coupled" and "coupling" are used herein according to their broad and ordinary meanings. For example, where a first feature, element, component, device, or member, is described as being "coupled" with or to a second feature, element, component, device, or member, such description may be understood as indicating that the first feature, element, component, device, or member, or portion thereof, is physically/mechanically attached, fixed, fastened, connected, linked, or joined to, or united, associated together, or integrated with, or embedded at least partially within, or otherwise physically related to, the second feature, element, component, device, or member, or portion thereof, whether directly or indirectly. A "coupling" can refer to any device, structure, form, tool, mechanism, means, position, apparatus, or portion, component, or position thereof that at least partially facilitates and/or effects/achieves the coupling of two or more features, elements, components, devices, or members, and/or portions thereof. In some instances and implementations, such rebalancing of tension may serve to produce substantially equal tension between the originally-differently-tension suture portions and/or groups of suture portions, thereby improving performance/functionality of the suture implant device(s) and/or reducing the risk of injury and/or other health complications that may result from uneven suture tension, as described in detail above. Furthermore, suture tension distribution facilitated by tension-distribution devices as disclosed herein can ensure that no single suture portion or grouping of suture portions bears more than fifty percent of the overall tension load on the sutures engaged with the device.

With respect to the illustrated implementation of FIG. 13, each of the illustrated suture portions 138a, 138b, 139a, 139b may represent single suture strands, suture pairs, or any other grouping of suture portions or strands. Furthermore, each of the illustrated suture portions may be associated with a separate tissue anchor or one or more of the illustrated suture portions may be associated with a common tissue anchor. For example, the suture pair 138 may comprise first and second suture tails 138a, 138b that are associated with a single tissue anchor, which may be implanted in a heart valve leaflet or other biological tissue, whereas the suture pair 139 may comprise first and second suture tails 139a, 139b that are associated with a separate tissue anchor, which likewise may be implanted in a heart valve leaflet (e.g., the same leaflet or another leaflet of the same heart valve) or other biological tissue. That is, as with other examples disclosed herein, the illustrated suture portions may represent any arrangement, configuration, and/or combination of suture portions associated with any grouping, configuration, arrangement, or number of tissue anchor devices (e.g., bulky knots).

Whereas some suture-tensioning solutions do not provide balancing of tension load distribution on sutures since all sutures are simultaneously pulled by hand to achieve the desired tissue anchor position and sufficient reduction of mitral regurgitation. Examples of the present disclosure advantageously allow surgeons to tension the suture tails of tissue anchors to achieved proper coaptation as well as balancing of tension across all sutures so that no one chord carries the bulk of the load.

FIG. 14 shows a cutaway side view of a tension-distribution device 146 having sutures 149 engaged therewith in accordance with one or more examples. Unlike the illustrated example of FIG. 13, which shows a tension-distribution device having at least four suture-engagement features 135 with suture portion(s) engaged therewith, the tension-distribution device 146 shown in FIG. 14 is shown as including two suture-engagement features 145 with which suture portions 149 are respectively engaged. The suture portions or groupings of suture portions 149 are tied or otherwise coupled at a fixation point 148 using one or more knots or other coupling/fixation mechanisms. In particular, the illustration of FIG. 14 shows a knot stack 147, which may comprise a plurality of knots tied in series in a stack (e.g., on top of each other). Differential tension between the suture portion 149a and the suture portion 149b may result in migration of the coupling 148 towards one of the suture-engagement features 145 and away from the other, as shown.

FIG. 15 shows a top and side perspective view of a tension-distribution device 150 in accordance with one or more examples. The example of FIG. 15 includes four suture-engagement features 155 (identified individually as 155a-d) evenly distributed rotationally about an axial center point CP of the device 150. The suture-engagement features 155 may comprise apertures or holes through which sutures can be passed or threaded. The suture-engagement features 155 can be positioned any desirable radial distance r from the center point CP. In some instances, the suture-engagement features 155 are advantageously relatively close to the outer edge 158 of the device 150 in order to provide a desirable and/or maximized distance d between opposite engagement features (e.g., 155c, 155b).

In some instances, the tension-distribution device 150 comprises a solid form, which may have a button-like shape, as shown. In some instances, the tension-distribution device 150 comprises an at least partially hollow form. The tension-distribution device 150 may have any suitable or desirable axial shape, such as a circular shape as shown in FIG. 15. In some instances, the device 150 has a square or rectangular shape, wherein the suture-engagement features 155 may be at or associated with corner or side-midpoint regions of the device. Any other suitable or desirable shape may also be implemented, such as star-type, oblong, triangular, or any other type of shape. As shown, the device 150 advantageously has rotational symmetry about the center axis CP.

The outer edge 158 of the device 150 can be at least partially rounded, such as at axial edges or corners thereof. In some instances, the sides 158 of the device 150 present a substantially flat and/or rounded surface at least over a certain thickness dimension thereof. The top face 152 of the device 150 may be substantially flat. In some instances, the face 152 is at least partially rounded or has certain topological features (not shown in the example of FIG. 15), which may assist in suture management and/or for other purposes or functionality.

FIG. 16 shows a bottom and side perspective view of the tension-distribution device 150 shown in FIG. 15 in accordance with one or more examples of the present disclosure. In some instances, the bottom side of the tension-distribution device 150 represents a substantially mirror image of the topside 152 of the device 150. For example, the device 150 may be axially symmetrical with respect to a center axial plane thereof.

The bottom face 154 of the device 150 may be substantially flat. In some instances, the face 154 is at least partially rounded or has certain topological features (not shown in the example of FIG. 15), which may assist in tissue- or pledget-interfacing, or other purposes or functionality. In some instances, the bottom surface 154 is convex in one or more portions or areas thereof to facilitate tilting or rotational contact with tissue or pledget or other surface with which it is in contact in its implanted configuration. In some instances, the bottom surface 154 is concave in one or more portions or areas thereof to facilitate fit with the tissue or other surface against which it is placed.

FIG. 17 shows a top or bottom view of a tension-distribution device 170 including four suture-engagement features in accordance with one or more examples. As described above, the various tension-distribution devices disclosed herein may have any suitable or desirable number of suture-engagement features. FIGS. 17 through 19 show different examples of suture-tension devices having different numbers of suture-engagement features. Although the illustrated suture-engagement features of FIGS. 17 through 19 are shown as apertures/holes, it should be understood that such examples may comprise or implement any suitable or desirable type of suture-engagement features, as described in detail herein.

The suture-engagement features 175 (identified individually as 175a-d) may be disposed/positioned at any suitable or desirable radius r, as described herein. With respect to four-feature implementations, the suture-engagement features 175 may be positioned at 90° of separation from adjacent features, as shown. The distance $d_i$ between opposing suture-engagement features (e.g., 175*b*, 175*d*) may generally be greater than the distance de between adjacent engagement features (e.g., 175*c*, 175*d*). As with all examples of tension-distribution devices in the present disclosure, the suture-engagement features 135 may be positioned at any suitable or desirable distance d3 from the outer edge 178 of the device 170. The illustrated example of FIG. 17 has fourth-degree rotational symmetry with four similar quadrant pieces/regions.

FIG. 18 shows a top or bottom view of a tension-distribution device 180 including three suture-engagement features 185 (identified individually as 185*a-c*) in accordance with one or more examples of the present disclosure. The suture-engagement features 185 may be disposed of any suitable or desirable radius r, as described herein. With respect to three-feature implementations, the suture-engagement features 185 may be positioned at 120° of separation from adjacent features, as shown. Implementation of examples like that shown in FIG. 18 may involve tying or otherwise fixing suture portions or groups of suture portions engaged with the respective engagement features 185 altogether in a central area of the device 180. The illustrated example of FIG. 18 has third-degree rotational symmetry.

FIG. 19 shows a top or bottom view of a tension-distribution device 190 including two suture-engagement features 195 (identified individually as 195*a*, 195*b*) in accordance with one or more examples of the present disclosure. The suture-engagement features 195 may be disposed of any suitable or desirable radius r, as described herein. With respect to two-feature implementations, the suture-engagement features 195 may be positioned at 180° of separation from adjacent features, as shown. The illustrated example of FIG. 19 has second-degree rotational symmetry.

FIG. 20 shows a bottom and side perspective view of a tension-distribution device 200 including a convex projection 203 in accordance with one or more examples of the present disclosure. The projection 203 may serve to provide a desirable tissue interface for the tension-distribution device 200 in order to allow for the device 200 to tilt to some degree more readily than examples comprising a substantially flat bottom or distal surface. The projection 203 may cover any suitable or desirable area of the bottom/distal surface 204 of the device 200. In some instances, the projection 203 covers an area that is radially within the area of the suture-engagement features 205 (identified individually as 205*a-d*). The convex projection 203 may have a curvature to facilitate rocking of the device 200. In some instances, the convex surface 203 may cover substantially the entire bottom surface 204 of the device 200. In such examples, the suture-engagement features 205 may be integrated at least in part with the convex surface 203. In some instances, the suture-engagement features 205 may comprise hook, loop, or other wire- or radial-projection-type features that project radially outward from the outer edge 208 of the device 200.

FIGS. 21-1 and 21-2 show side views of a tension-distribution device 210 having a convex projection 213 as implanted in accordance with one or more examples of the present disclosure. According to the implementation of FIG. 21-1, suture portions 219 may be passed through or otherwise engaged with suture-engagement features 215 (identified individually as 215*a*, 215*b*) of a tension-distribution device 210, wherein the suture portions are tied or otherwise fixed to the tension-distribution device 210, such as at areas associated with the respective suture-engagement features 215. That is, according to the implementation of FIG. 21-1, the suture portions and/or groups of suture portions 219 may not be tied together from opposing or separate suture-engagement features 215 on the proximal or top side 202 of the device 210. For example, suture pairs or individuals suture portions may be knotted to prevent withdrawal of the sutures distally back through the suture-engagement features 215. That is, a diameter of the knots in the knot stacks (or other type of suture coupling) 217 may be greater than that of the relevant portions of suture-engagement features 215.

Unlike certain other examples disclosed herein, suture balancing/distribution may be achieved using the device 210 through tilting and/or rotating of the device 210 using the convex projection 213 rather than through migration of proximal suture knots across a surface or other area of a top or proximal side of the device 210. Greater tension in one suture portion or group of suture portions 219*b* compared to other suture portion group of suture portions 219*a* may cause the tilting of the device 210 as shown in FIG. 21-1. As shown in FIG. 21-1, tilting of the device 210 can shorten the distance between the fixation point of the knot 217*b* and the distal target anchoring point (not shown) associated with the suture portion(s) 219*b*, thereby reducing the tension thereof. Conversely the distance between the suture fixation point of the knot 217*a* and the distal target anchoring point (not shown) associated with the suture portion(s) 219*a* may be increased by the tilting of the device 210, thereby increasing the tension of the suture portion(s) 219*a*.

According to the implementation of FIG. 21-2, balancing/distribution of tension between the suture portions 219*a* and 219*b* may be achieved both through tilting of the tension-distribution device 210 and through migration of the suture fixation point associated with the knots or other suture-coupling mechanism 217. That is, the suture portions may be brought through the respective suture-engagement features 215 and tied on the top/proximal side 202 of the device 210. For example, greater tension in the suture portion(s) 219*b* may cause tilting of the device 210 in the direction of the suture-engagement feature 215*b* through which such suture portions are passed or otherwise engaged. Such differential tension in favor of the suture portion(s) 219*b* may further cause migration of the suture coupling 217 toward the suture-engagement feature 215*b*. With the combined effect of both the tilting of the device 210 enabled by the convex projection 213 and the migration of the knots 217, substantial tension rebalancing may be achieved.

FIG. 22 shows a side view of a tension-distribution device 226 having sideways suture-engagement features 225 in accordance with one or more examples of the present disclosure. Unlike certain other examples of the present disclosure in which suture-engagement features are oriented to provide for the passing of suture portions through a bottom or distal face of the tension-distribution device, the device 226 includes suture-engagement features 225 that allow for the passage, threading, and/or other type of engagement of suture portions therewith through a side surface or portion 228 of the device 226. For example, as shown in FIG. 22, suture portions 229*a*, 229*b* may pass through a tissue wall 221 and under and/or around a base 224 of the device 226, or under/distal side thereof.

With suture portions and/or groupings of suture portions 229 engaged with the sideways suture-engagement features 225, such suture portions may be coupled to one another at a coupling point 222, such as through the tying of one or more knots 227 (e.g., a not stack). The coupling 227 may be inclined to migrate to some degree between the sideways suture-engagement features 225a, 225b, thereby at least partially balancing and/or distributing tension between the suture portion(s) 229a and 229b. For example, the coupling 227 (e.g., a knot stack) may be permitted to slide or move on or above the base 224. The suture portions 229a, 229b may be tied together from opposite/opposing and/or adjacent suture-engagement features.

FIG. 23 shows a top and side perspective view of a tension-distribution device 236 having sideways suture-engagement features 235 (identified individually as 235a-d) in accordance with one or more examples of the present disclosure. In some instances, the device 236 includes a base 234 and one or more circumferential/peripheral side portions 238. Although the side portion 238 is shown as continuous around a circumference/periphery of the device 236, in some instances, the side portion(s) may be associated only with one or more arc lengths of the circumference/periphery of the device 236. For example, side portions may be present in the areas of the suture-engagement features 235 with circumferential interruptions therebetween. Furthermore, although the device 236 is illustrated in FIGS. 23 and 24 as including a base portion 234, in some instances, the device 236 does not include a base. For example, the device 236 may comprise a ring form having one or more sideways/radial suture-engagement features without a base associated therewith.

Although the tension-distribution device 236 of FIGS. 23 and 24 is shown as having a generally circular axial shape, as with other examples of the present disclosure, the device 236 may have any suitable or desirable shape. As implemented to distribute tension among suture portions and/or groupings of suture portions (e.g., suture pairs), suture portions may be coupled/tied from opposing suture-engagement features (e.g., 235b, 235d) or may be coupled, joined, or tied from adjacent suture-engagement features as with the joined/coupled suture portions 239b of the joined/coupled suture portions 239a, 239b between the suture-engagement features 235a and 235b.

FIG. 24 shows a bottom and side perspective view of the tension-distribution device 236 of FIG. 23 in accordance with one or more examples of the present disclosure. In the illustration of FIG. 24, the base portion 234 is shown as being substantially flat over an area thereof. However, in some instances, the tension-distribution device 236 includes a base having a convex surface or area configured to facilitate or promote tilting or rocking of the device when disposed against tissue, pledget, or other surface. Such exterior topology of the base 234 may provide increased tension-distribution functionality in some cases. As with other examples of the present disclosure, the tension-distribution device 236 may have any number and/or arrangement of suture-engagement features.

FIG. 25 shows a side view of a tension-distribution device 256 having a cover feature 253 in accordance with one or more examples of the present disclosure. Although the tension-distribution device 256 is shown as having sideways suture-engagement features 255, as described in detail herein, it should be understood that the suture-engagement features 255 may be through the base portion 254 of the device rather than the sides 258. Furthermore, any other suitable or desirable configuration of suture-engagement features may be utilized and/or incorporated with the tension-distribution device 256.

The tension-distribution device 256 includes a cover portion 253, which may be disposed and/or positioned at or near a proximal side or end of the device 256, as shown in FIG. 25. The cover portion 253 may serve to house at least parts of the suture portions 259 (identified individually as 259a, 259b) that are engaged with the suture-engagement features 255. For example, one or more knots and/or other fixation mechanisms or points implemented to join/couple respective suture portions may be housed within a chamber formed within the base 254, sides 258, and cover portion 253, as shown in FIG. 25. The cover portion 253 may serve to protect the sutures and/or coupling 257 from certain environmental parameters/conditions and/or may help prevent embolism formation and/or other undesirable interactions of the sutures and/or coupling 257 with the physiology of patient. In some instances, the cover portion 253 includes an aperture or other feature 252 through which suture tails may pass. Although the coupling 257 is shown within the chamber of the device 256, in some instances, such coupling may be implemented external to the device 256, such as on the cover portion 253. For example, the coupling/knots 257 may have a diameter greater than that of the opening 252, thereby preventing the coupling 257 from being drawn back through the opening 252.

FIG. 26 shows a top and side perspective view of a tension-distribution device 266 having a cover feature 263 in accordance with one or more examples of the present disclosure. Similarly to the device 256 disclosed in connection with FIG. 25 above, the tension-distribution device 266 shown in FIGS. 26 and 27 includes a cover feature 263. It should be understood that cover features of tension-distribution devices disclosed herein may comprise a removable cover separate from the base and/or side portions of the tension-distribution device, or may be integrated with the base and/or side portions, such as in a unitary form therewith. In some instances, a tension-distribution device in accordance with aspects of the present disclosure includes a proximal/upper cover portion having an aperture associated therewith and one or more side portions coupled and/or configured to be coupled to the cover portion without a base being associated therewith. That is, certain tension-distribution devices may have an open-bottom shape or configuration.

FIG. 27 shows a top and side perspective view of the tension-distribution device 266 of FIG. 26 in accordance with one or more examples, wherein suture portions 269a, 269b are engaged with certain suture-engagement features 265 and coupled together in accordance with aspects of the present disclosure. The aperture 262 of the cover 263 may be configured to allow for suture portions and/or coupling/knots to be passed therethrough.

FIG. 28 shows a top and side perspective view of a tension-distribution device 286 having one or more proximal suture channels 282 (identified individually as 282a-d) in accordance with one or more examples of the present disclosure. In some instances, tension-distribution devices in accordance with aspects of the present disclosure include certain channels, grooves, paths, or the like that are configured to receive and/or guide/contain portions of sutures to thereby facilitate desired tension distribution/balancing. Although the channels 282 of the device 286 are shown and described as being on a proximal or upper side of the device 286, such channels may be associated with any suitable or desirable area or portion of the device 286. In some instances, the channels 282 are at least partially closed. For example, the channels may be closed over at least a portion of an area 281 of a channel between an outer perimeter of the device 286 and a central area 283. Therefore, the channels 282 may be considered part of the suture-engagement features 285 of the device 286.

The channels 282 may have any suitable or desirable dimension, shape, width, depth, curvature, direction, and/or the like. Furthermore, although channels are shown traversing a diameter of the device 286 from opposing portions or areas of the perimeter thereof, it should be understood that channels may follow any suitable or desirable path through and/or along the tension-distribution device. For example, although the channels 282 are shown as providing paths connecting opposing (e.g., diametrically opposite) suture-engagement features 285, in some instances channels are configured to connect between adjacent suture-engagement features in a direct manner, meaning that such connection path need not run through the central area 283. Suture-management channels in accordance with aspects of the present disclosure may comprise any suitable or desirable topographical shape and/or configuration. Channels as shown and/or described above may be incorporated and/or implemented in connection with any of the examples of tension-distribution devices and/or components disclosed herein.

The tension-distribution device 286 may comprise any suitable or desirable type of suture-engagement features 285. In some instances, as shown in FIG. 28, the device 286 may have no separate suture-engagement features other than the ingress portions of the channels 282 and the channels themselves. Alternatively, the device 286 may include sideways apertures or other suture-engagement features associated with the perimeter/side 288 of the device 286. Alternatively, the device 286 may include through-the-base apertures or other types of suture-engagement features associated with the base or bottom surface of the device 286.

With the suture portions 289 (identified individually as 289*a*, 289*b*) coupled and disposed in the channels 282, the coupling (e.g., knot stack) 287 may be permitted to slide within one or more regions of the channels 282, thereby distributing tension as described in detail herein. In some instances, the tension-distribution device 286 comprises a pledget having suture-management channels as described herein (e.g., formed in the pledget or attached thereto).

FIG. 29 shows a side view of a tension-distribution device 296 having one or more proximal suture channels 292 with one or more suture portions 299 engaged therewith in accordance with one or more examples of the present disclosure. As implanted in accordance with certain surgical procedures, the tension-distribution device 296 can have suture portions or groupings of suture portions 299 engaged therewith through or with any suitable or desirable suture-engagement features according to present disclosure. The suture portions 299 may be coupled in any suitable or desirable way, wherein such coupling 297 may be permitted to migrate within one or more channels to thereby distribute or balance the tension of the respective suture portions 299*a*, 299*b*.

FIG. 30 shows a side view of a tension-distribution device 306 disposed on a pledget 302 in accordance with one or more examples of the present disclosure. Although certain examples are disclosed herein in the context of a tension-distribution device being implanted with suture portions engaged therewith, wherein the tension-distribution device is disposed on or adjacent to a tissue wall or surface (e.g., external ventricular wall), in some implementations, a tension-distribution device in accordance with aspects of the present disclosure may be disposed on a pledget 302, which may generally be disposed between the tension-distribution device 306 and the relevant tissue wall 301. For example, suture portions 309 (identified individually as 309*a*, 309*b*) may be passed through the tissue wall 301, and further through one or more portions or areas of the pledget 302, and engaged with the tension-distribution device 306 on a proximal side of the pledget 302, as shown in FIG. 30. The tension-distribution device 306 may conform to any of the disclosed features or examples of the present disclosure with respect to suture-engagement features 305 and/or other features or configurations of the device 306. The suture portions 309 may be coupled in accordance with the present disclosure on the proximal side of the tension-distribution device 306, such as in connection with a knot or other coupling 307.

FIG. 31 shows a bottom and side perspective view of a tension-distribution device 316 in accordance with one or more examples. As illustrated and described above, certain examples of the present disclosure are presented in the context of circular tension-distribution devices. Furthermore, certain examples are disclosed herein in the context of tension-distribution devices that comprise even numbers of suture-engagement features, wherein such features facilitate the coupling of pairs of suture portions and/or pairs of groupings of suture portions. However, as referenced and described in detail herein, such devices may comprise any suitable or desirable shape, number, and/or arrangement of suture-engagement features. The example illustrated in FIG. 31 of the tension-distribution device 316 provides an example of a tension-distribution device having a non-circular shape and/or non-even number of suture-engagement features.

In the illustrated example of FIG. 31, the tension-distribution device 316 comprises a generally triangular shape having corner portions 317 that are associated with certain suture-engagement features 315. Although the corner portions 317 of the device 360 are shown as having a generally flat configuration, such features may be rounded, or have any other suitable or desirable shape or configuration.

Although illustrated as sideways suture-engagement features, the features 315 may be through-the-base axially-oriented suture-engagement features as described in detail herein. FIG. 31 shows certain suture portions engaged with the tension-distribution device 316 and coupled in accordance with aspects of the present disclosure. For convenience, the image of FIG. 31 shows suture pairs 319 (identified individually as 319*a-c*) respectively engaged with the suture-engagement features 315. However, it should be understood that each of the suture-engagement features 315 may have engaged therewith any number of suture portions. The three suture pairs 319 may be knotted or otherwise coupled together on an upper or proximal side of the tension-distribution device 316, such as through knotting or other coupling means/mechanism.

In some instances, the tension-distribution device 316 includes one or more channels or guidance paths 312 to facilitate managements and/or functionality of the device 316. The shape and/or configuration of the device 316 may allow for the coupling of the suture pairs 319 to migrate generally in the direction of one or more of the suture-engagement features 315, thereby at least partially balancing and/or distributing tension among the suture pairs.

FIG. 32 shows a perspective view of at least a base of a tension-distribution device 320 in accordance with one or more examples of the present disclosure. For example, the illustrate device 320 may be a base components of a multi-component tension-distribution device, or may be a tension-distribution device in and of itself. The tension-distribution device 320 is illustrated as a device comprising three suture-engagement features 325 associated with three triangle corner regions 327. However, as with other examples disclosed herein, tension-distribution devices and components like the device 320 shown in FIG. 32 may comprise any number of suture-engagement features and/or arrangement thereof.

The device 320 includes a plurality of suture channels 322, which may facilitate managements of suture portions engaged with the device 320. Although illustrated with suture channels 322, in some instances, the device 320 may not have channels. In some instances, the device 322 includes a central aperture 323, which may be utilized for retention and/or engagement of suture portions for various purposes. In some instances, the device 320 may serve as a top cover portion for a tension-distribution device. In the illustrated example, the suture-engagement features comprise peripheral recesses into which suture portions and/or groupings of suture portions may be placed. However, any suitable or desirable types of suture-engagement features may be implemented in connection with the device 320, including axial apertures that allow for threading of suture portions therethrough through the plane of the device 320.

FIG. 33 shows a perspective view of at least a portion of a tension-distribution device 330 including sideways suture-engagement features 335 in accordance with one or more examples of the present disclosure. In some instances, the device 336 includes a base 334 and one or more peripheral side portions 338. Although the side portion 338 is shown as continuous around a periphery of the device 336, in some instances, the side portion(s) may be associated only with one or more areas of the periphery of the device 336. For example, side portions may be present in the areas of the suture-engagement features 335 with peripheral gaps/interruptions therebetween. Furthermore, although the device 336 is illustrated in FIG. 33 as including a base portion 334, in some instances, the device 336 does not include a base. For example, the device 336 may comprise a band or ring form having one or more sideways/radial suture-engagement features without a base associated therewith.

Although the tension-distribution device 336 of FIG. 33 is shown as having a generally triangular axial shape with flattened corners 337, as with other examples of the present disclosure, the device 336 may have any suitable or desirable shape. As implemented to distribute tension among suture portions and/or groupings of suture portions (e.g., suture pairs), suture portions may be tied/coupled together from all of the suture-engagement features 335, as shown with the coupling 331 of the suture portions 339, or may be coupled from adjacent suture-engagement features (e.g., 335*a* and 335*b*).

When the various coupled suture portions 339 (identified as 339*a-c*) have uneven tension, at least initially, once coupled, the coupling 331 may migrate generally in the direction of the suture-engagement feature(s) with which the relatively more-tensioned suture portion(s) is/are engaged. For example, such migration may reflect vectors corresponding to the relative tension of the sutures. Therefore, if the suture portion(s) 339*c* initially have/has the highest tension and the suture portion(s) 339*b* have/has the relatively lowest tension, whereas the suture portion(s) 339*b* have/has a tension that is somewhere between the highest and the lowest, the coupling 331 may migrate to the greatest extent towards the suture-engagement feature 335*c*, and to a lesser extent towards the suture-engagement feature 335*a*. That is, the migration force (e.g., force vector(s)) experienced by the coupling 331 may be greatest in the direction of the feature 335*c* and to a lesser extent in the direction of the feature 335*a*.

FIG. 34 shows a in perspective view of at least a portion of a tension-distribution device 340 in accordance with one or more examples of the present disclosure. The example of FIG. 34 includes three suture-engagement features 345 that are positioned and/or oriented in an axial direction. That is, the position and/or orientation of the suture-engagement features 345 may be different than the features 335 of FIG. 33, which are generally oriented in a radial direction. Therefore, the suture-engagement features 345 may be considered through-the-base apertures or features. The illustrated device 340 may be a base component of a multi-component tension-distribution device or may be a tension-distribution device in and of itself. As implemented to distribute tension among suture portions and/or groupings of suture portions (e.g., suture pairs), suture portions may be coupled (e.g., tied) together from all of the suture-engagement features 345 or may be fixed, joined, tied, or otherwise coupled from adjacent suture-engagement features.

FIG. 35 shows a side view of a tension-distribution device 356 having a plurality of suture portions engaged therewith accordance with one or more examples of the present disclosure. FIG. 13 shows a plurality of suture portions (or pairs or other groupings of suture portions) 359 engaged with the device 356. For example, such suture portions 359 may be associated with respective tissue anchors, such as heart valve leaflet anchors, as described in detail herein. In some implementations, the suture portions 359 may traverse the tissue wall 351 and may be anchored on a proximal side 55 of the tissue wall 351 to thereby secure the respective suture pairs and/or suture portions in a tensioned configuration between the tension-distribution device 356 on a proximal end and a distal target tissue-anchoring location on a distal end (not shown).

The tension-distribution device 356 may be a generally-triangular device, as described above in connection with certain other examples of the present disclosure. The tension-distribution device 336 may or may not comprise a proximal/upper cover component or portion.

In some instances, the tension-distribution device 356 includes certain suture-engagement features 355 configured to allow for suture portions and/or pairs/groupings of suture portions to be engaged therewith in a manner to allow for longitudinal sliding of the suture portion(s) through the suture-engagement features. In the illustrated example, the suture-engagement features 355 comprise sideways apertures through which suture portions and/or suture portion pairs/groupings may be threaded or passed in some manner. Unlike certain other examples of the present disclosure in which suture-engagement features are oriented to provide for the passing of suture portions through a bottom or distal face of the tension-distribution device, the device 356 includes suture-engagement features 355 that allow for the passage, threading, and/or other type of engagement of suture portions therewith through a side surface or portion(s) 358 of the device 356. For example, as shown in FIG. 35, the suture portions 359 may pass through the tissue wall 351 and under and/or around a base 354 of the device 356, and/or an underside (e.g., bottom or distal side) thereof.

With suture portions and/or groupings of suture portions engaged with the sideways suture-engagement features 355, such suture portions may be coupled to one another at a coupling point 352, such as through the tying of one or more knots 357 (e.g., a knot stack). The coupling point 352 may be inclined to migrate to some degree on or within the device 356 between the sideways suture-engagement features 355, thereby at least partially balancing and/or distributing tension between the suture portion(s) 359. For example, the coupling 352 (e.g., a knot stack 357) may be permitted to slide or move on or above the base 354. The suture portions 359 may be all tied together or may be tied/coupled in pairs of suture portions or pairs of groupings of suture portions.

FIG. 36 is a flow diagram illustrating a process 360 for distributing or balancing tension among a plurality of suture portions and/or groupings of suture portions in accordance with one or more examples of the present disclosure. At block 362, the process 360 involves implanting one or more tissue anchors in biological tissue of a patient, wherein the tissue anchor(s) are each associated with one or more suture tails/portions. For example, the one or more tissue anchors may comprise knot-type heart valve leaflet anchors configured to be implanted in leaflet tissue and to be tethered to some degree by the respective suture portion(s) associated therewith.

At block 364, the process 360 involves engaging two or more suture portions and/or groupings of suture portions (e.g., suture pairs) with respective suture-engagement features of a tension-distribution device in accordance with aspects of the present disclosure. For example, with respect to heart valve repair procedures, the suture portions may be tethered at a distal end by respective tissue anchors, wherein the suture portion(s) tether the tissue anchor(s) through a tissue wall, such as a ventricular wall of a heart of the patient. Therefore, some portion of the various suture portion(s) may generally be disposed external/proximal to the tissue wall through which the suture portions pass.

Engaging the suture portions with the respective suture-engagement features of the tension-distribution device may involve threading the suture portions through aperture-type engagement features, or any other suitable or desirable type of engagement feature configured to physically contain and/or secure the suture portions, while allowing for relatively free longitudinal sliding of the suture portions through the engagement features. The engagement features may be sideways-oriented or may be oriented primarily in an axial direction, as described in detail herein.

At block 366, the process 360 involves coupling the suture portions and/or groupings of suture portions that are engaged with the respective suture-engagement features of the tension-distribution device in some manner. For example, the operation(s) associated with block 366 may involve tying one or more knots (e.g., a knot stack) to fix/couple separate suture portions and/or groupings of suture portions to one another across an area and/or path on or within the tension-distribution device 356.

At block 368, the process 360 involves permitting the coupling of the suture portions that are engaged with the tension-distribution device to migrate on and/or within the tension-distribution device to thereby balance and/or distribute the respective tension loads of the sutures, thereby producing more evenly distributed/balanced tensioning across the suture portions.

Parallel-Plate Tension-Balancing Devices and Processes

In some implementations, the present disclosure relates to systems, devices, and methods for balancing tension among a plurality of sutures and/or groupings of sutures. FIG. 37 shows a side view of a tension-balancing device 370 in accordance with one or more examples. The device 370 may be considered a parallel-plate tension-balancing device and includes first 372 and second 374 plate structures that may be used or implemented to determine and/or set balanced tension levels in suture portions engaged with the balancing device 370. The terms "plate" and "plate structure" are used herein according to their broad and ordinary meanings, and may refer to any structure in the form of a layer, slab, sheet, panel, or other generally or at least partially flat structure with respect to one or more portions thereof, such as one or more axial surfaces or faces thereof.

The tension-balancing device 270 includes a fulcrum component 373, which may have any suitable or desirable shape or form. In particular, the fulcrum 373 may advantageously be configured to facilitate the tilting and/or rocking of one of the plates 372, 374 with respect to the other of the plates. For example, in some instances, the fulcrum 373 is attached or otherwise integrated to/with one of the plate structures 372, 374. For example, as shown in FIG. 37, the fulcrum 373 may be attached to and/or integrated with the plate structure 374. Although the plate structure 374 is shown in FIG. 37 as a bottom plate structure, it should be understood that the plate structures 372, 374 may be relatively axially oriented in any suitable or desirable manner or order. Therefore, references to a bottom plate structure, a top plate structure, a proximal plate structure, and/or a distal plate structure are referred to as such for convenience only, and it should be understood that such references may refer to any plate structure of a parallel-plate tension-balancing device in accordance with examples of the disclosure.

In some instances, the fulcrum 373 is semi-spherical in shape. The fulcrum component 373 may be removable or detachable from the plate structure 374. However, in some instances, the fulcrum 373 may be fixed to and/or integrated with the plate structure 374 in some manner. For example, the fulcrum 373 may be fixed to the plate structure 374 in that plate structure 374 cannot tilt relative to the fulcrum 373. Rather, relational tilting between the plate structure 372 and the plate structure 374 may be achieved and/or facilitated by tilting of the plate structure 372 on and relative to the fulcrum 373. Generally, the plate structure associated with the fulcrum component can be referred to as the "base" plate structure, whereas the plate structure configured to balance on the fulcrum component can be referred to as the "balancing" plate structure.

One or both of the plate structures 372, 374 may have associated therewith certain suture-fixation features 375 configured to have sutures fixed thereto in such a manner as to at least partially restrict the sliding and/or other longitudinal movement of suture portions 373 engaged therewith relative to one or more components of the suture-fixation features 375. The suture-fixation features 375 may have any suitable or desirable form or configuration designed to have sutures engaged with the various component thereof. For example, in the illustrated example, the suture-fixation features 375 include a bar 377, or any other type of arbor, mandrel, spool center, reel, or like structure around which a suture may be at least partially wrapped or against which the suture can be secured or placed. The features 375 further include a flange component 376, which may be dimensioned and/or configured to restrict movement or sliding of suture portions engaged with the features 375 radially outward (e.g., in an axial direction with respect to the bar 377) from the associated plate structure to thereby maintain suture engagement with the respective suture-fixation feature. Therefore, sutures may be fixed at least in part to the suture-fixation component(s) 375 by wrapping the suture around the bar 377 one or more times to achieve sufficient frictional force thereon to prevent longitudinal sliding of the suture portion through/within the fixation feature.

It should be understood that any type of suture-fixation features may be implemented in connection with examples of the present disclosure. For example, in some instances, spring-type and/or other forces/components may be implemented to cause the flange 376 to press radially inward (e.g., axially inward with respect to the axis of the bar 377) to secure the suture. In some instances, the suture-engagement features 375 comprise spring-loaded clips, clamps, brackets, levers, straps, bands, or the like that are configured to secure in place suture portions engaged therewith between the flange 376 and the periphery of the plate structure. In some instances, the suture-fixation features 375 comprise certain tension-adjustment features, such as tuning pegs or pins, or the like. In some instances, tuning features comprise attached or detachable tuning levers configured to increase the tension of a suture by winding and/or unwinding suture around a peg, bar, or similar structure. Such features may provide for micro-adjustment of suture tension. In some instances, sutures may be released from fixation by actuation or engagement of a button, tab, lever, or the like, wherein release of such components may cause suture tension to be fixed/locked. Generally, examples of suture-fixation features in accordance with examples of the present disclosure advantageously allow for selective locking/fixing and unlocking/unfixing of sutures to the respective plate structure through any means or mechanism, including those described above.

In some instances, suture-fixation features are associated with only one of the two plate structures of the device 370. That is, peripheral suture-fixation features may be associated with either or both of the plate structures 372, 374. In some instances, both of the plate structures 372, 374 comprise and/or have associated therewith suture-fixation features, although the suture-fixation features associated with only one of the plate structures may be utilized to fix suture portions when balancing tension in the sutures, whereas the sutures may only contact the suture-fixation features associated with the other plate structure without being fixed thereto. In some instances, the sutures are fixed only to suture-fixation features associated with the balancing plate structure.

With the sutures 379 fixed to suture-fixation features 375 associated with at least one of the plate structures 372, 374, relative tilt between the plate structures may provide an indication of relative tension of the sutures fixed thereto. Therefore, by increasing and/or decreasing tension on sutures engaged with the device 370 in a manner as to bring the plate structure 372, 374 into approximate parallel arrangement with one another, suture tension across the sutures fixed to the device 370 may be approximately balanced.

The fulcrum 373 is shown as having a dome-like, semi-spherical form, which may be conducive to plate tilting in accordance with the functionality of the device 370. However, it should be understood that fulcrum components of tension-balancing devices in accordance with the present disclosure may have any suitable or desirable shape and/or form. For example, a fulcrum may have a conical shape/form, or any other form that includes a central apex. Furthermore, in some instances, the fulcrum may have an off-center apex, which may allow for designed un-even tension among sutures.

The balancing plate of parallel-plate tension-balancing devices of the present disclosure can advantageously inform the surgeon as to which sutures are tighter and which ones are looser. The surgeon may strive to tension all sutures evenly enough for the two plates to become substantially parallel with each other, or to a more parallel state. Furthermore, although four suture-fixation features are shown in FIG. 37 for a given plate structure, plate structures can have any number of suture-fixation fieatures, such as two, three, or four. Parallel-plate tension-balancing devices in accordance with the present disclosure can be configured to be attached to a tourniquet to provide a desired fixture for the device. For example, a plate structure secured to the tourniquet can serve as a relatively stationary plate, whereas the other/rotatable plate can interface with the stationary plate through a fulcrum associated with either the stationary plate or the rotatable plate. In some instances, sutures can be looped through suture-fixation features of both the stationary and rotatable plates and clamped thereto.

FIG. 38 shows a base/fulcrum portion 384 of a tension-balancing device in accordance with one or more examples of the present disclosure. Although referred to as a base component in some contexts herein, it should be understood that the plate structure of a tension-balancing device that is associated with a fulcrum component may be an upper, lower, top, bottom, or otherwise-oriented structure. The plate structure 384 can include an interior surface 388 that may be at least partially flat. Generally, the fulcrum component 383 may be positioned and/or disposed at an axial center of the plate structure 384. Such positioning may advantageously provide a central pivot point or apex for relative tilting of the plate structures. In some instances, the fulcrum component 383 may be offset from the axial center of the plate structure 384. For example, such offsetting may be implemented in order to account for desired tension differences for certain sutures, such that greater tension may be required for some sutures integrated with the device 384 to produce parallel plate structures.

The fulcrum component 383 may be a semi-spherical projection, or any other shape that approximates a sphere at least in part. Such shape of the fulcrum 383 can advantageously provide for 360° tilt and/or pivoting in all directions. In some instances, the fulcrum 383 is designed to allow for tilting in only certain directions. For example, the fulcrum 383 may comprise a semi-cylindrical shape configured to allow for pitching or banking, but not both. For example, in examples comprising only two suture-fixation features and configured to produce balancing for only 2 suture portions and/or groupings of suture portions, it may be desirable to restrict the tilting action associated with the device to tilting in the direction of such suture-fixation features and not allow for banking in directions orthogonal thereto. The fulcrum 383 may cover only a portion of the interior surface 388 of the plate structure 384 or may alternatively cover substantially all of the interior surface 388 of the structure 384.

Although illustrated as comprising a plurality of suture-fixation features 385, in some instances, the base plate structure 384 may not comprise suture-fixation features. Furthermore, although peg-type fixation features are shown in FIG. 38, it should be understood that the plate structure 384 may comprise other types of suture-fixation and/or suture-engagement features, such as apertures, hooks, or the like. For example, the base 384 may include suture-engagement features configured to contain sutures/suture portions without necessarily fixing such suture portions. That is, such features may allow for suture portions engaged therewith to slide/move longitudinally within such features when engaged therewith.

FIG. 39 shows a perspective view of a balancer portion 392 of a tension-balancing device in accordance with one or more examples of the present disclosure. The plate structure 392 can include an interior surface 398 that may be at least partially flat. In some instances, the balancer structure 392 includes a recess or concavity 393 that is configured to receive/hold at least a portion of a fulcrum component of a corresponding base plate structure. The recess 393 may serve to orient the opposing plate structures of the tension-balancing device in axial alignment with one another. The recess 393 may further serve to facilitate tilting/rotation of the balancer plate 392 about the fulcrum component of the base plate structure. In some instances, the balancer plate structure 392 does not include the illustrated recess/concavity feature 393. That is, in such examples, tilting of the balancer plate structure 392 on the fulcrum component of the base plate structure may occur at an interface between the fulcrum of the base structure and the flat interior surface 398 of the balancer structure.

Generally, the recess/concavity 393 may be positioned and/or disposed at an axial center of the plate structure 392 to align with the fulcrum component 384 of the base structure (see FIG. 38). Such positioning may advantageously provide a central pivot point or area for relative tilting of the plate structures. The recess/concavity 393 may have a semi-spherical shape, or any other shape that approximates a sphere at least in part. Such shape of the fulcrum 323 can advantageously provide for 360° tilt and/or pivoting in all directions. In some instances, the recess/concavity 393 is designed to allow for tilting in only certain directions. For example, the recess/concavity 393 may have a semi-cylindrical shape to allow for pitching or banking, but not both. For example, for examples comprising only two suture-fixation features and configured to produce balancing for only two suture portions and/or groupings of suture portions, it may be desirable to restrict the tilting action associated with the device to tilting in the direction of such suture-fixation features and not allow for banking in directions orthogonal thereto.

Although illustrated as comprising a plurality of suture-fixation features 395, in some instances, the balancer portion 392 may not comprise suture-fixation features. Furthermore, although peg-type fixation features are shown in FIG. 39, it should be understood that the balancer plate structure 392 may comprise other types of suture-fixation and/or suture-engagement features, such as apertures, hooks, or the like. For example, the balancer 392 may include suture-engagement features configured to contain sutures/suture portions without necessarily fixing such suture portions. That is, such features may allow for suture portions engaged therewith to slide/move longitudinally within such features when engaged therewith.

The respective plate structures of parallel-plate tension-balancing devices in accordance with aspects of the present disclosure may have any suitable or desirable number, arrangement, configuration, and/or type of suture-fixation features. FIG. 40 shows a component 400 (e.g., base or balancer plate structure) of a tension-balancing device including four suture-fixation features 405 (identified individually as 405a-d) in accordance with one or more examples of the present disclosure. In some instances comprising four suture-fixation features as in the example of FIG. 40, such features may be positioned at or near a periphery of the plate structure 400 and circumferentially evenly distributed, wherein adjacent suture-fixation features are offset by about 90°, as shown in FIG. 40. Plate structures of tension-balancing devices in accordance with examples of the present disclosure can advantageously have rotational symmetry, as illustrated in the accompanying figures.

FIG. 41 shows a component 410 (e.g., base or balancer plate structure) of a tension-balancing device including three suture-fixation features 415 (identified individually as 415a-c) in accordance with one or more examples of the present disclosure. In some instances comprising three suture-fixation features 415, as in the example of FIG. 41, such features 415 may be positioned at or near a periphery of the plate structure 410 and circumferentially evenly distributed, wherein adjacent suture-fixation features are offset by about 120°, as shown in FIG. 41. FIG. 42 shows a component 420 (e.g., base or balancer plate structure) of a tension-balancing device including two suture-fixation features in accordance with one or more examples of the present disclosure. In some instances comprising two suture-fixation features 425 (identified individually as 425a, 425b) as in the example of FIG. 42, such features 425 may be positioned at or near a periphery 421 of the plate structure 420 and circumferentially evenly distributed, wherein the suture-fixation features 425 are offset by about 180°, as shown in FIG. 42.

FIG. 43 shows a component 430 (e.g., base or balancer plate structure) of a tension-balancing device including slit-type suture-fixation features 435 (identified individually as 435a-d) in accordance with one or more examples. The plate structure 430 can include any number and/or configuration of suture-fixation/engagement features 435 configured to receive suture portions therein and hold the same at least in part in a fixed and/or secured position through a friction fit. For example, the sutures may be pulled into the recesses of the respective suture-fixation features 435, wherein the width of the slot/slit 435 is such that at a certain depth within the slot/slit, the walls thereof contact and hold the suture portions to some degree, thereby providing fixation functionality in accordance with aspects of the present disclosure.

Although slit-/slot-type suture-fixation features are shown in FIG. 43, it should be understood that other types of friction-fit features may be implemented in accordance with examples of the present disclosure. For example, such features may be cut into and/or otherwise integrated with the plate structure 430, and/or may be attached to a periphery 431 thereof. In some instances, the features 435 can be dimensioned and/or configured to have suture portions placed therein, while not necessarily fixing such portions. For example, the features 435 may rather serve to maintain the suture portions in a desired area, while still permitting longitudinal sliding of the suture portions.

FIGS. 44 through 48 show side and perspective views, respectively, of aspects of a tension-balancing device 440 subject to various suture tension conditions in accordance with one or more examples. The diagrams of FIGS. 44 through 48 relate to certain use cases for tension-balancing devices in accordance with aspects of the present disclosure and are provided to further clarify aspects of operation of certain parallel-plate tension-balancing devices.

Figure 44:
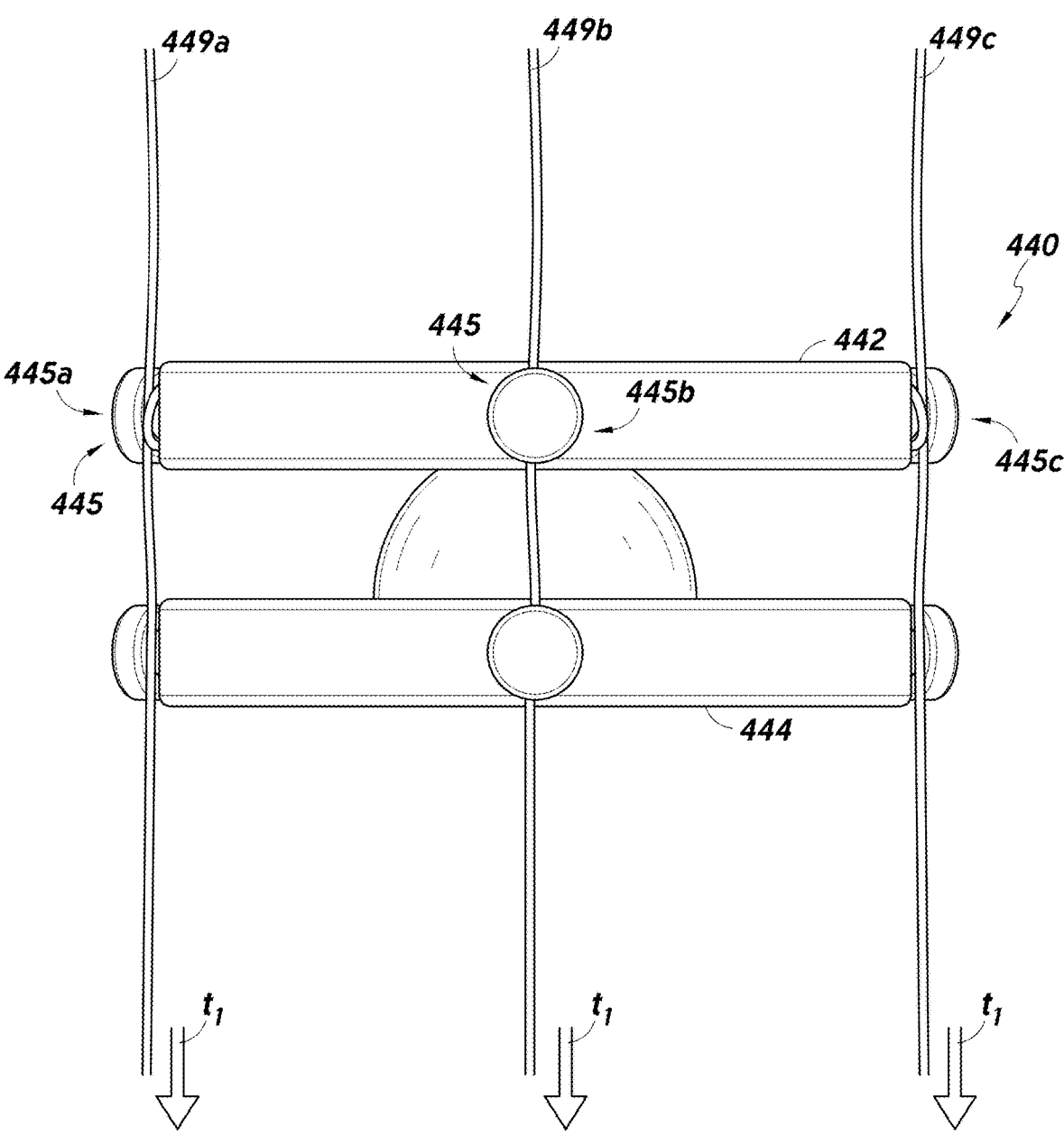

FIG. 44 shows a tension-balancing device 440 including first 442 and second 444 plate structures, as described in detail herein. The downward arrows shown at the bottom of the diagram of FIG. 44 represent the respective tension associated with the sutures positions adjacent to such arrows. For example, in the particular configuration of FIG. 44, the tensions $t_i$ associated with the sutures 449 are shown as being equal. Therefore, with the sutures fixed to suture-fixation features 445 (identified individually as 445a-c) associated with the balancer plate structure 442, the balancer plate structure 442 may be approximately parallel/balanced relative to the base/fulcrum plate structure 444. Although the sutures 449 are shown as fixed to suture-fixation features 445 associated with the balancer plate structure 442, it should be understood that in some implementations, sutures may be fixed instead to suture-fixation features associated with the base/fulcrum plate structure 444. That is, in order for relative tilting to be indicative of suture tension balance/distribution, sutures may advantageously be fixed to one of the plate structures, but not both. Furthermore, it may be advantageous for the plate structure to which the sutures are not fixed to have a stable/secure position. Therefore, in some instances, at least one of the plate structures is secured to a tourniquet or other relatively stable structure. Furthermore, in some implementations, it may be desirable for the stationary plate structure (e.g., the base/fulcrum plate structure 444 in FIG. 44) to be oriented approximately orthogonal to the orientation of the sutures emanating from their respective tissue anchors. With multiple sutures coming from multiple tissue anchors, it may not be possible to align the stationary plate 444 orthogonally to all sutures. In such cases, it may be desirable to orient the stationary plate structure 444 generally in the direction of orthogonality with the direction of the sutures (e.g., within 45° of orthogonality as each of the anchored sutures.

Figure 45:
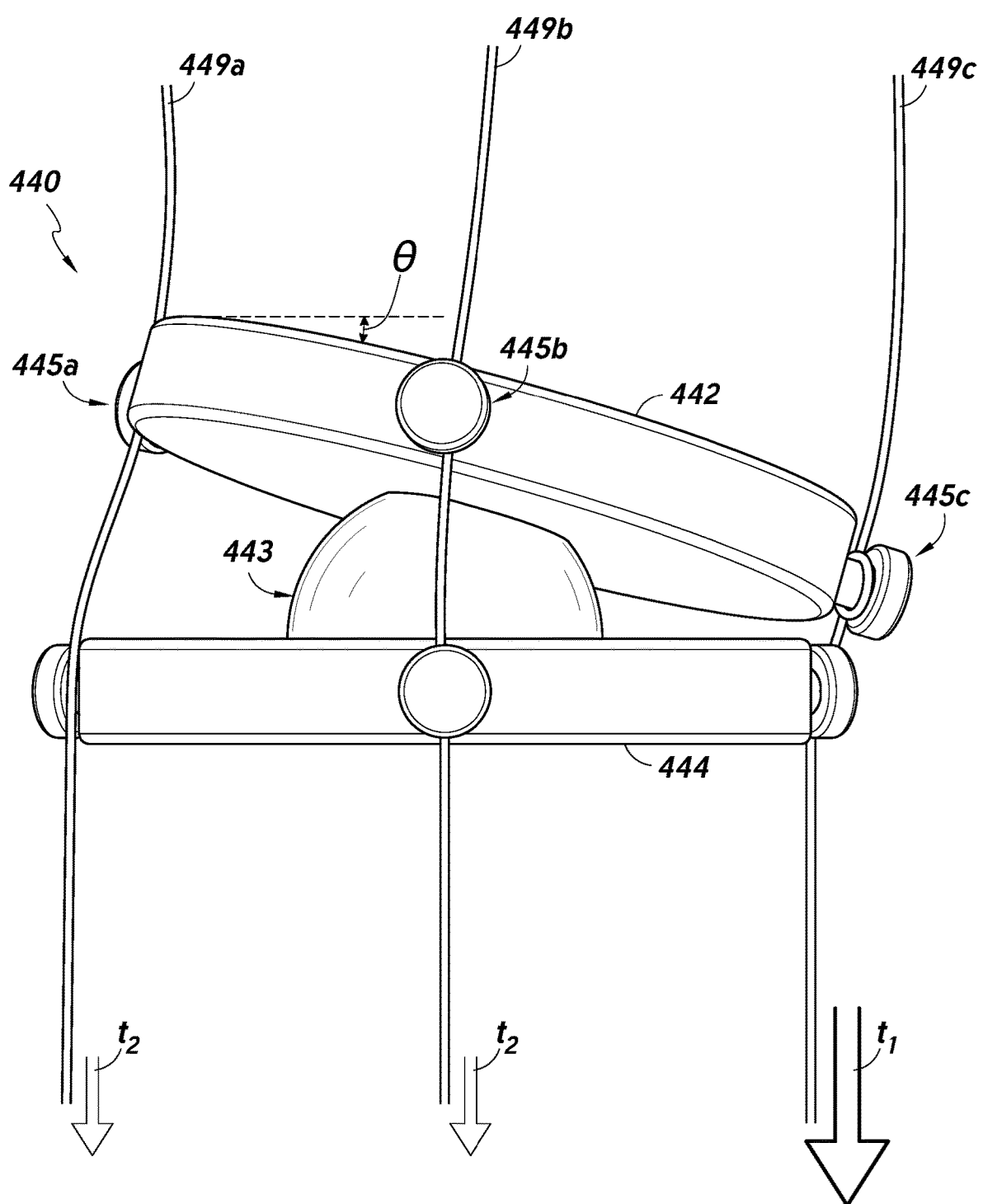

FIG. 45 shows the tension-balancing device 440, wherein the sutures 449 are at least partially unevenly tensioned. In the illustrated use case of FIG. 45, the suture 449$c$ is tensioned to a greater degree $t_i$ than the sutures 449$a$ and 449$b$. As shown in FIG. 45, the sutures 449$a$ and 449$b$ may have a similar tension the applied thereto, which is less than the tension $t_i$ on the suture 449$c$. The uneven tension $t_i$ on the suture 449$c$ can result in tilting of the balancer plate structure 442, which is fixed to the suture 4490 at the suture-fixation feature 445$c$. For example, relative to the plane of the base plate structure 444, the balancer plate structure 442 is shown as being tilted at an angle θ.

Figure 46:
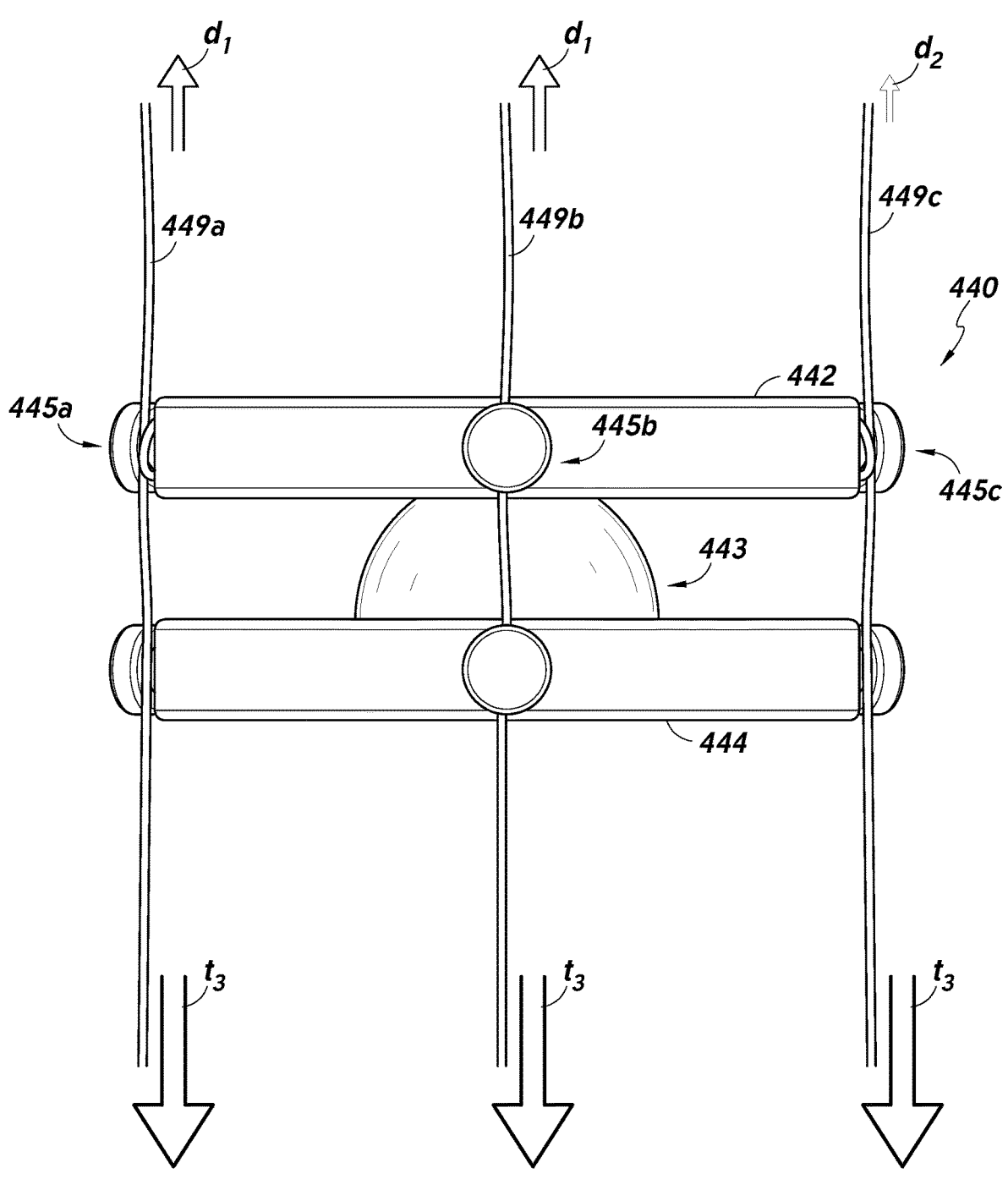

The image in FIG. 46 shows the tension-balancing device 440 with the balancer plate structure 442 drawn approximately parallel to the base structure 444. For example, such parallel orientation may be achieved by adjusting the sutures 449 in accordance with their respective initial tensions. For example, due to the greater initial tension $t_i$ on the suture 449$c$, the remaining sutures 449$a$, 449$b$ may be pulled/tightened by distance or amount $d_i$ that is greater than the amount of pulling/tightening d2 on the suture 449$c$. In some implementations, the suture 449$c$ that is initially tensioned to a higher degree may not be tightened at all, or may even be loosened by some amount. Therefore, it should be understood that the amounts of tightening/pulling illustrated in the respective figures and described herein may correspond to a negative amount or value in some instances, which may be interpreted as loosening or otherwise reducing the tension on the suture.

Figure 47:
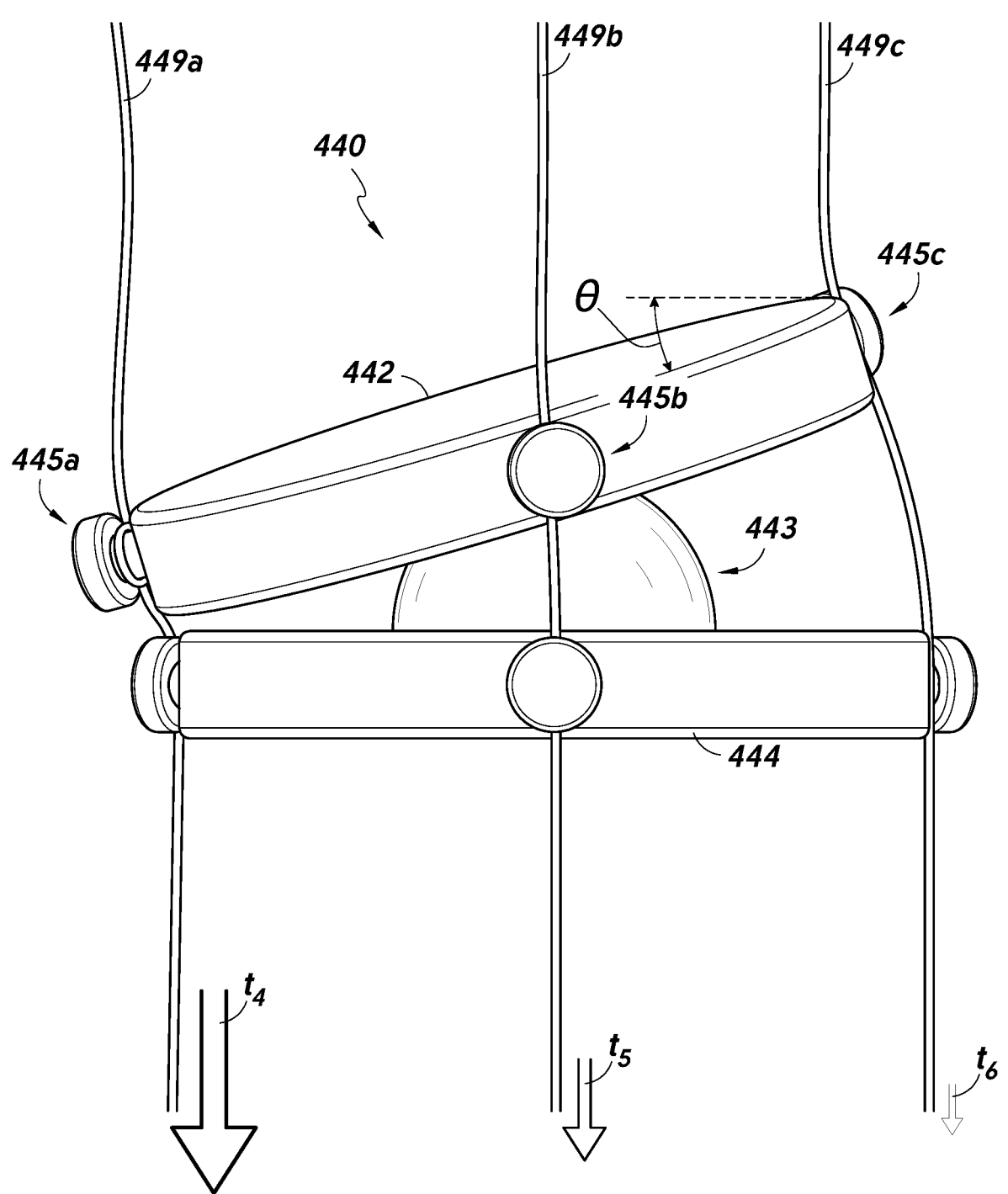

FIG. 47 shows the tension-balancing device 440, wherein the sutures 449 are unevenly tensioned. In the illustrated use case of FIG. 47, the suture 449$c$ is tensioned to a lesser amount to than the sutures 449$a$ and 449$b$, wherein the suture 449$a$ is tensioned to a greater amount $t_i$ than the suture 449$b$ (tensioned to an amount to). The uneven tensions $t_4$, $t_5$, and to on the sutures 449$a$, 449$b$, and 449$c$, respectively, can result in tilting of the balancer plate structure 442, which is fixed to the sutures 449 at respective ones of the suture-fixation features 445. For example, the balancer plate 442 may be tilted towards the suture 449$a$, and, to a lesser extent, towards the suture 449$b$, as shown.

Figure 48:
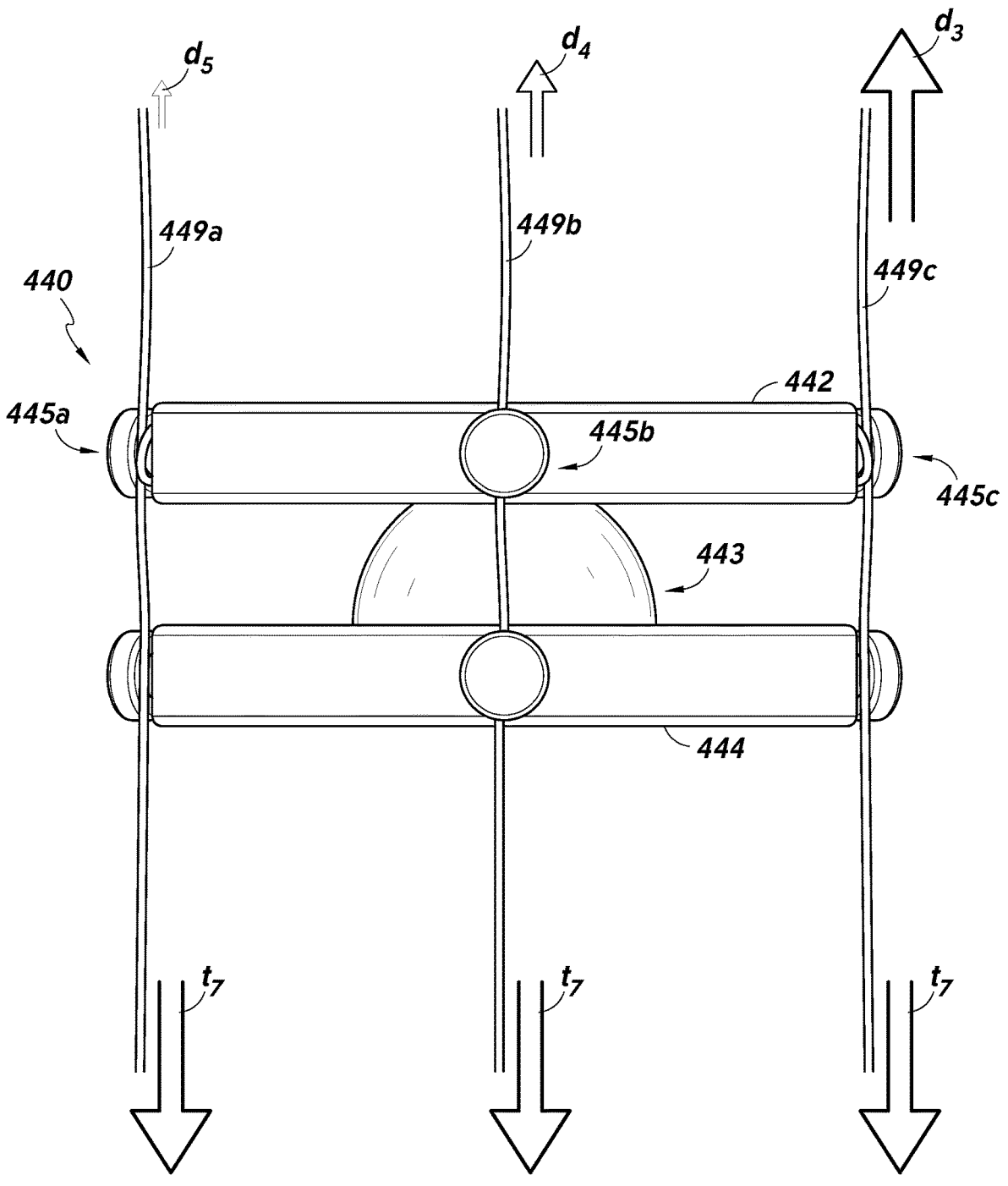

The image in FIG. 48 shows the tension-balancing device 440 with the balancer plate structure 442 drawn approximately parallel to the base structure 444. For example, such parallel orientation may be achieved by adjusting the sutures 449 in accordance with their respective initial tensions (see FIG. 47). For example, due to the greatest initial tension $t_4$ being on the suture 449$a$, such suture may be loosened, or tightened to a relatively lesser amount, indicated by the arrow $d_5$. The intermediately-tensioned suture 449$b$ may be loosened/tightened to an intermediate amount $d_4$, whereas the remaining suture 4490 may be pulled/tightened by distance or amount do that is greater than the amounts of pulling/tightening $d_4$, $d_5$ on the sutures 449$a$, 449$b$. In some implementations, the suture 449$a$ that is initially tensioned to the highest degree $t_4$ may not be tightened at all, or may be loosened by some amount. Furthermore, although tightening/pulling of sutures to balance tension-balancing devices is described in connection with certain examples and aspects of the present disclosure, it should be understood that loosening of sutures that are overtightened may be implemented to effect the desired balancing of the plate structure(s).

FIGS. 49-1 and 49-2 illustrate a flow diagram for a process 490 for tensioning sutures in accordance with one or more examples. FIGS. 50-1 and 50-2 shows certain images corresponding to respective blocks, states, and/or operations associated with the process of FIG. 49 in accordance with one or more examples. The process 490 may be performed at least in part using a parallel-plate tension-balancing device that is configured to be attached to a tourniquet to facilitate the even distribution of tension of sutures. For example, the process 490 may be implemented in connection with a mitral valve leaflet repair procedure. Therefore, the process 490 may be considered a heart valve repair procedure in some implementations.

At block 492, the process 490 involves fixing sutures to suture-fixation features of a tension-balancing device 510. For example, the tension-balancing device may include a stationary plate structure 514, which may be attached to a tourniquet 511 as in the image 501 of FIG. 50-1, and a rotational plate 512 with a half-dome fulcrum interfacing with the stationary plate. In some implementations, sutures may be looped through suture-fixation features associated with one or the both stationary and rotatable plate structures and/or clamped thereto. The operation(s) associated with block 492 may be performed following placement of multiple knot-type tissue anchors on (e.g., the P2 segment of the posterior mitral leaflet), which may be guided by transesophageal echocardiography (TEE).

At block 494, the process 490 involves adjusting the tension of the sutures fixed to the suture-fixation features to balance the base and balancer plate structures of the tension-balancing device to bring them into approximate parallel alignment. For example, the suture-fixation features may be engaged by the surgeon to release the sutures therefrom so that the tensions of the sutures can be adjusted, after which the sutures can be once again fixed to the device 510. Adjustment of suture tension may be performed until the desired coaptation is achieved to reduce regurgitation and/or until the plate structures of the tension-balancing device are approximately parallel.

At block 496, the process 490 involves clamping the sutures at the adjusted/balanced tensions in some manner. For example, forceps or other tool(s) may be used to hold/clamp the sutures at the desired tensions, as shown in image 505 of FIG. 50-2. At block 948, the process 490 involves removing the tourniquet from the sutures. At block 499, the process 490 involves anchoring the sutures to the tissue wall 521 (e.g., exterior wall of the left ventricle) and/or pledget 522 disposed thereon. For example, such anchoring can be accomplished by tying a plurality of knots 517 with the tensioned sutures.

Additional Examples

Depending on the example, certain acts, events, or functions of any of the processes or algorithms described herein can be performed in a different sequence, may be added, merged, or left out altogether. Thus, in certain examples, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain examples require at least one of X, at least one of Y and at least one of Z to each be present.

It should be appreciated that in the above description of examples, various features are sometimes grouped together in a single example, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular example herein can be applied to or used with any other example(s). Further, no component, feature, step, or group of components, features, or steps are necessary or indispensable for each example. Thus, it is intended that the scope of the disclosure and claims should not be limited by the particular examples described above but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which the examples belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method for tensioning sutures in a patient in need thereof, the method comprising:

providing a rotationally-symmetric tension-distribution device including:
a first plate, and
a dome-shaped fulcrum projecting from the first plate and configured to facilitate tilting of the first plate about a center of the fulcrum, the fulcrum having a lateral extent that is smaller than the first plate such that a rim of the first plate extends radially outward beyond the fulcrum;

engaging one or more first suture portions with a first suture-engagement feature associated with a first circumferential position of the rim of the first plate radially outside of the fulcrum;

engaging one or more second suture portions with a second suture-engagement feature associated with a second circumferential position of the rim of the first plate that is on an opposite side of the first plate from the first circumferential position; and adjusting tension of the one or more first suture portions and tension of the one or more second suture portions at least in part by permitting the first plate to tilt about the fulcrum of the tension-distribution device in response to greater tension in the one or more first suture portions compared to the one or more second suture portions.

2. The method of claim 1, wherein said engaging the one or more first suture portions with the first suture-engagement feature comprises fixing tension of the one or more first suture portions at the first suture-engagement feature.

3. The method of claim 1, wherein said engaging the one or more first suture portions with the first suture-engagement feature comprises looping the one or more first suture portions around the first suture-engagement feature, the first suture-engagement feature comprising a peg that projects radially from the rim of the first plate.

4. The method of claim 1, further comprising further adjusting the tension of the one or more first suture portions and the tension of the one or more second suture portions manually to tilt the first plate of the tension-distribution device to a balanced orientation.

5. The method of claim 4, further comprising clamping the tension of the one or more first suture portions and the tension of the one or more second suture portions after tilting the first plate of the tension-distribution device to the balanced orientation.

6. The method of claim 1, wherein said adjusting is performed postoperatively within a closed chest cavity of the patient.

7. The method of claim 1, further comprising pulling slack out of at least one of the one or more first suture portions or the one or more second suture portions prior to said engaging the one or more first suture portions.

8. The method of claim 1, wherein the first suture-engagement feature and the second suture-engagement feature are positioned:

on a common radial axis of the tension-distribution device; and on opposite sides of the tension-distribution device.

9. The method of claim 1, wherein:

the one or more first suture portions are associated with a first implanted tissue anchor; and the one or more second suture portions are associated with a second implanted tissue anchor.

* * * * *